(12) United States Patent
Rezania

(10) Patent No.: US 9,388,386 B2
(45) Date of Patent: Jul. 12, 2016

(54) DIFFERENTIATION OF HUMAN EMBRYONIC STEM CELLS INTO SINGLE HORMONAL INSULIN POSITIVE CELLS

(71) Applicant: Janssen Biotech, Inc., Horsham, PA (US)

(72) Inventor: Alireza Rezania, Skillman, NJ (US)

(73) Assignee: Janssen Biotech, Inc., Horsham, PA (US)

(*) Notice: Subject to any disclaimer, the term of this patent is extended or adjusted under 35 U.S.C. 154(b) by 95 days.

(21) Appl. No.: 13/708,369

(22) Filed: Dec. 7, 2012

(65) Prior Publication Data
US 2013/0189777 A1    Jul. 25, 2013

Related U.S. Application Data

(60) Provisional application No. 61/579,351, filed on Dec. 22, 2011.

(51) Int. Cl.
| | | |
|---|---|---|
| C12N 5/00 | (2006.01) | |
| C12N 5/02 | (2006.01) | |
| C12N 5/071 | (2010.01) | |

(52) U.S. Cl.
CPC .......... *C12N 5/0676* (2013.01); *C12N 2500/34* (2013.01); *C12N 2500/38* (2013.01); *C12N 2501/117* (2013.01); *C12N 2501/15* (2013.01); *C12N 2501/155* (2013.01); *C12N 2501/16* (2013.01); *C12N 2501/19* (2013.01); *C12N 2501/385* (2013.01); *C12N 2501/41* (2013.01); *C12N 2501/415* (2013.01); *C12N 2501/727* (2013.01); *C12N 2506/02* (2013.01)

(58) Field of Classification Search
CPC .......................... C12N 5/0676; C12N 2500/34
USPC ................................................. 435/325, 377
See application file for complete search history.

(56) References Cited

U.S. PATENT DOCUMENTS

| | | | |
|---|---|---|---|
| 5,843,780 | A | 12/1998 | Thomson |
| 5,942,435 | A * | 8/1999 | Wheeler ........................ 435/325 |
| 7,033,831 | B2 | 4/2006 | Fisk et al. |
| 7,326,572 | B2 | 2/2008 | Fisk et al. |
| 7,534,608 | B2 | 5/2009 | Martinson et al. |
| 7,704,738 | B2 | 4/2010 | D'Amour et al. |
| 7,993,920 | B2 | 8/2011 | Martinson et al. |
| 2005/0158852 | A1 | 7/2005 | Wang et al. |
| 2005/0266554 | A1 | 12/2005 | D'Amour |
| 2009/0093055 | A1 | 4/2009 | Fisk et al. |
| 2009/0170198 | A1 | 7/2009 | Rezania |
| 2010/0015100 | A1 | 1/2010 | Xu |
| 2010/0112693 | A1 | 5/2010 | Rezania et al. |

FOREIGN PATENT DOCUMENTS

| | | |
|---|---|---|
| WO | 2009018453 A1 | 2/2009 |
| WO | 2009070592 A1 | 6/2009 |

OTHER PUBLICATIONS

Brevini et al., 2010, Theriogenology, vol. 74, pp. 544-550.*
Paris et al. (2010, Theriogenology, vol. 74, pp. 516-524).*
Munoz et al. (2008, Theriogenology, vol. 69, pp. 1159-1164).*
Shim et al. (2007, Diabetologia, vol. 50, pp. 1228-1238).*
Hirsinger et al. (1997, Development, vol. 124, pp. 4605-4614).*
MacDonald et al. (2009, Dev. Cell, vol. 17(1), pp. 9-26).*
Pownall et al. (2010, FGF Signalling in Vertebrate Development, Morgan & Claypool Life Sciences, 1 pg. printout).*
Saad et al. (2011, World J. Gastrointest. Surg., vol. 3(11), pp. 159-166).*
D'Amour et al. (2006, Nature Biotechnology, vol. 24(11), pp. 1392-1401).*
Dominguez-Bendala J. teaches (2009, Pancreatic Stem Cells, Stem Cell Biology and Regenerative Medicine, Humana Press, pp. 11-33).*
Reijo et al. (2009, Differentiation, vol. 78, pp. 18-23).*
Reubinoff et al. (2000, Nature Biotechnology, vol. 18, pp. 399-404).*
2008, Ireland KA., Visualizing Human Biology, 3rd Ed., Wiley and Sons Inc., 3 pages total.*
International Search Report dated Mar. 19, 2013 for application No. PCT/US2012/068439.
Baetge, Production of B-Cells from Human Embryonic Stem Cells, Diabetes, Obesity, Metabolism, 2008, pp. 186-194, vol. 10, Supplement 4.
Bocian-Sobkowska, et al., Polyhormonal Aspect of the Endocrine Cells of the Human Fetal Pancreas, Histochem Cell Biol, 1999, pp. 147-153, vol. 112, Issue 2.
Borowiak, et al., How to Make AB Cells, Current Opinion Cell Biology, 2009, pp. 727-732, vol. 21, Issue 6.
Chen, et al., A Small Molecule that Directs Differentiation of Human ESCs into the Pancreatic Lineage, Nature Chemical Biology, Apr. 11, 2009, pp. 258-265, vol. 5, No. 4.
D'Amour et al., Efficient differentiation of human embryonic stem cells to definitive endoderm, Nature Biotechnology, Oct. 28, 2005, 1-8, :W.1038/nbt1163, Nature Publishing Group.
D'Amour et al., Production of pancreatic hormone-expressing endocrine cells from human embryonic stem cells, Nature Biotechnology, Oct. 19, 2006, 1392-1401, 24-11, Nature Publishing Group, US.
Jeon, et al., Endocrine Cell Clustering During Human Pancreas Development, J Histochem Cytochem, 2009, pp. 811-824, vol. 57, Issue 9.
Jiang, et al, Generation of Insulin-Producing Islet-Like Clusters from Human Embryonic Stem Cells, Stem Cells, 2007, pp. 1940-1953, vol. 25, Issue 8.

(Continued)

*Primary Examiner* — Anoop Singh
*Assistant Examiner* — David A Montanari
(74) *Attorney, Agent, or Firm* — Lois A. Gianneschi

(57) ABSTRACT

The present invention provides methods to promote the differentiation of pluripotent stem cells. In particular, the present invention provides methods to produce a population of cells, wherein greater than 10% of the cells in the population express markers characteristic of single hormonal pancreatic beta cells.

6 Claims, 79 Drawing Sheets

(56) References Cited

OTHER PUBLICATIONS

Kelly, et al., Cell-Surface Markers for the isolation of Pancreatic Cell Types Derived from Human Embryonic Stem Cells, Nature Biotechnology, 2011, pp. 750-756, vol. 29, Issue 8.

Kroon, et al., Pancreatic Endoderm Derived from Human Embryonic Stem Cells Generates Glucose-Responsive Insulin-Secreting Cells in vivo, Nature Biotechnology, Apr. 2008, pp. 443-452, vol. 26, No. 4.

Loh, et al., Genomic Approaches to Deconstruct Puripotency, Annu Rev Genomics Hum Genet, 2011, pp. 165-185, vol. 12.

McLin et al., Repression of WNT/(szligbeta)-6atenin Signaling in the Anterior Endoderm is Essential for Liver and Pancreas Development, Development, 2007, pp. 2207-2217, vol. 134, Issue 12.

Nostro, et al., Stage-Specific Signaling Through TGF Family Members and WNT Regulates Patterning and Pancreatic Specification of Human Pluripotent Stem Cells, Development, 2011, pp. 861-871, vol. 138, Issue 5.

Rezania, Production of Functional Glucagon-Secreting-Cells from Human Embryonic Stem Cells, Diabetes, 2011, pp. 239-247, vol. 60, Issue 1.

Sherwood, et al., Transcriptional Dynamics of Endodermal Organ Formation, Developmental Dynamics, 2009, pp 29-42, vol. 238, Issue 1.

Stafford, et al., Retinoic Acid Signaling is Required for a Critical Early Step in Zebrafish Pancreatic Development, Current Biology, 2002, pp. 1215-1220, vol. 12, Issue 14.

Thomson et al., Embryonic Stem Cell Lines Derived from Human Blastocysts, Science, Nov. 6, 1998, 1145-1147, 282, HighWire Press.

Thomson et al., Isolation of a primate embryonic stem cell line, Developmental Biology, Aug. 1995, 7844-7848, 92, Proc. Natl. Acad. Sci, US.

Thomson et al., Primate Embryonic Stem Cells, Currenl Topics in Developmental Biology, 1998, 133-154, 38, Academic Press, US.

Wells, et al., Early Mouse Endoderm is Patterned by Soluble Factors from Adjacent Germ Layers, Development, 2000, pp. 1563-1572, vol. 127, Issue 8.

Wilson, et al., The HMG Box Transcription Factor Sox4 Contributes to the Development of the Endocrine Pancreas, Diabetes, 2005, pp. 3402-4309, vol. 54, Issue 12.

Zhang_et_al., Highly Efficient Differentiation of Human ES Cells and iPS Cells into Mature Pancreatic Insulin-Producing Cells, Cell Research, 2009, pp. 429-438, vol. 19, Issue 14.

Zorn, et al., Vertebrate Endoderm Development and Organ Formation, Annual Review Cell Development Biology, 2009, pp. 221-251, vol. 25.

European Search Report dated Jun. 8, 2015 for application No. EP 12860751.

Cao, et al., High Glucose is Necssary for Complete Maturation of Pdx1-VP16-Expressing Hepatic Cells into Functional Insulin-Producing Cells, Diabetes, 2004, pp. 3168-3176, vol. 53.

Jiang, et al., In Vitro Derivation of Functional Insulin-Producing Cells from Human Embryonic Stem Cells, Cell Research, 2007, pp. 333-344, vol. 17.

Rezania, et al., Enrichman of Human Embryonic Stem Cell-Derived NKX6.1—Expressing Pancreatic Progenitor Cells Accelerates the Maturation of Insulin-Secreting Cells In Vivo, Stem Cells, 2013, pp. 2432-2442, vol. 31.

Shi et al., Inducing Embryonic Stem Cells to Differentiate into Pancreatic βCells by a Novel Three-Step Approach with Activin A and All-Trans Retinoic Acid, Stem Cells, 2005, 656-662, 23, AlphaMed Press.

Wang, et al., Three-Dimensional Differentiation of Embryonic Stem Cells into islet-Like Insulin-Producing Clusters, Tissue Engineering: Part A, 2009, pp. 1941-1952, vol. 15, No. 8.

* cited by examiner

Isotype

Chromogranin

KI-67

NKX6.1

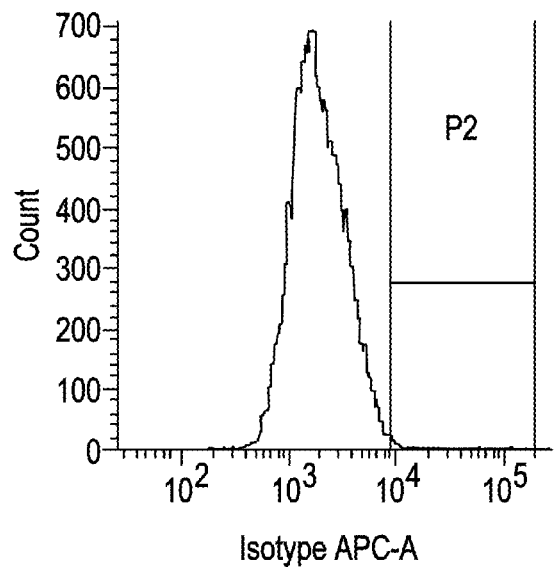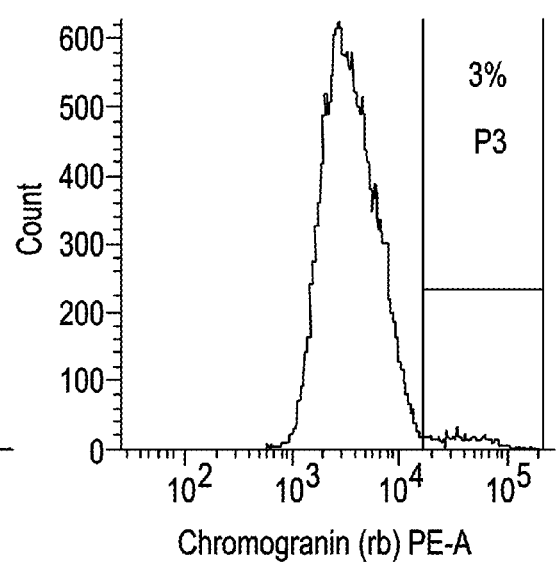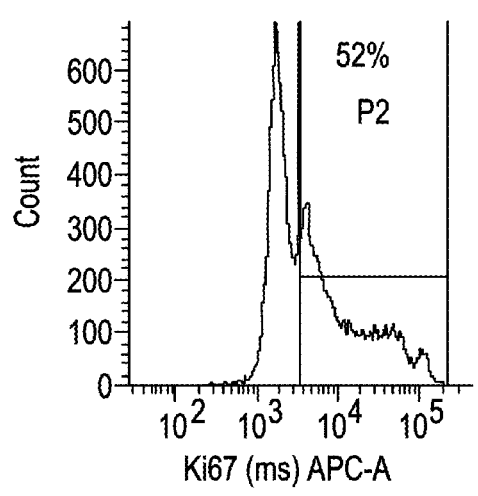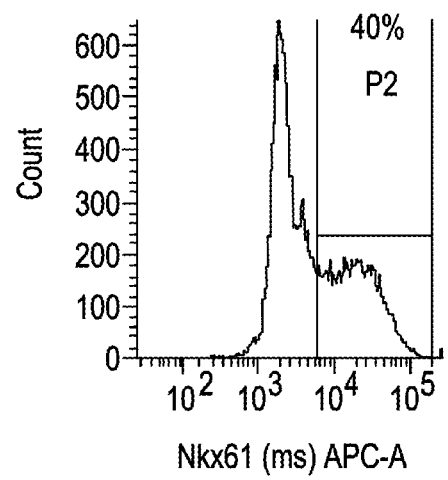

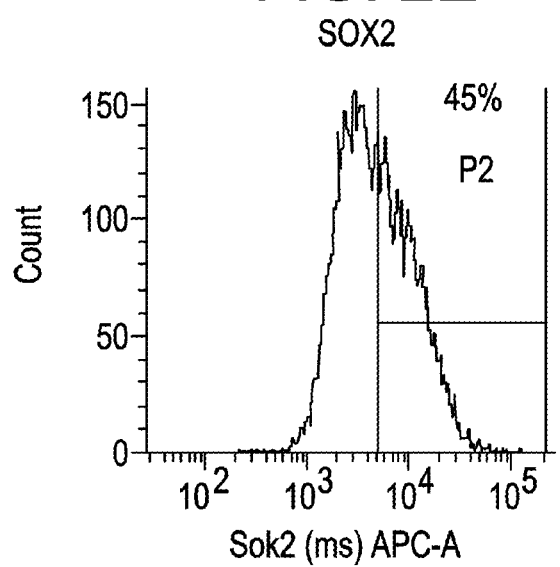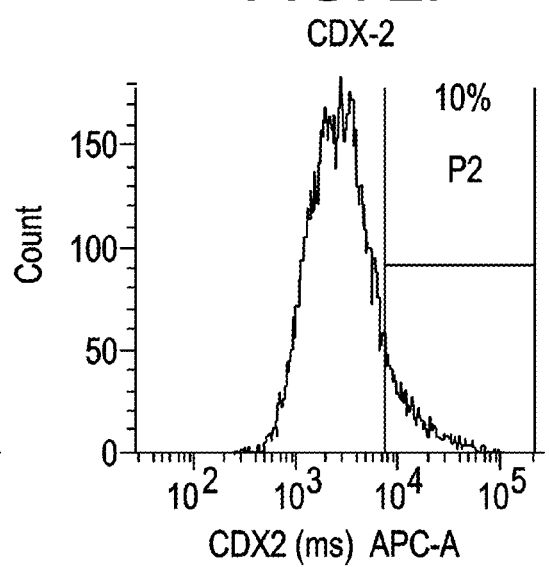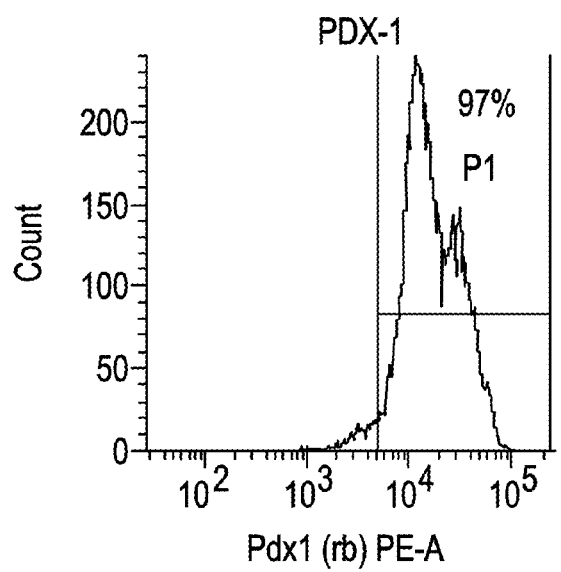

Isotype

Chromogranin

KI-67

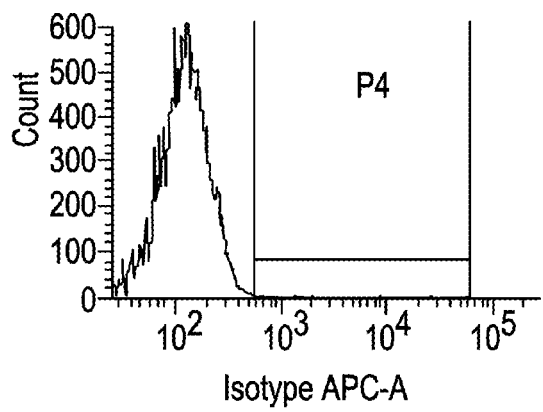
FIG. 4A Isotype
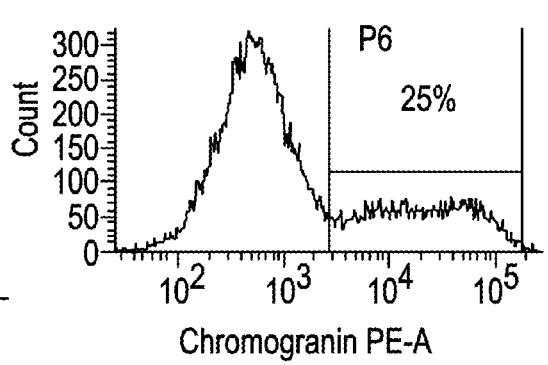
FIG. 4B Chromogranin
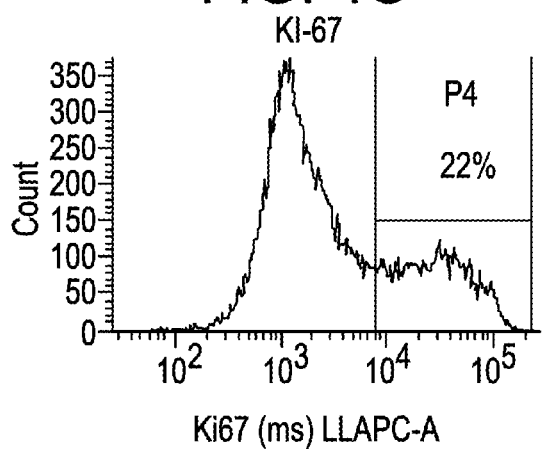
FIG. 4C KI-67
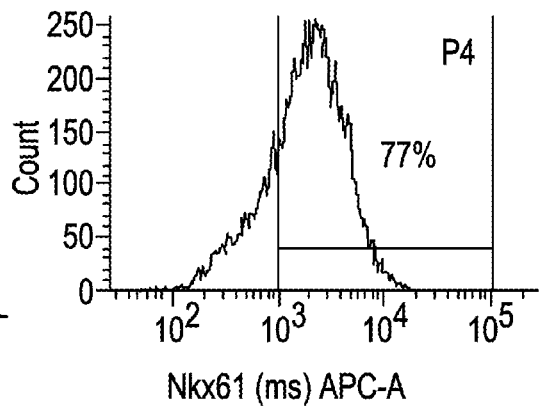
FIG. 4D NKX6.1
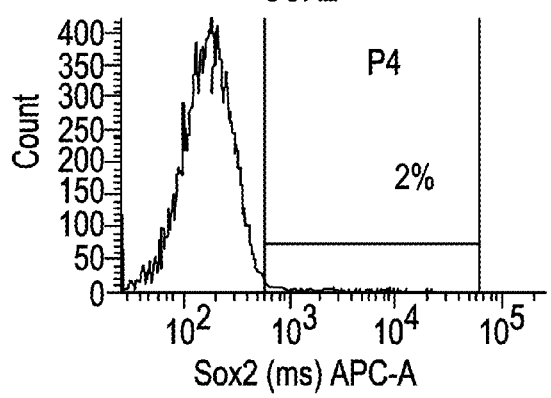
FIG. 4E SOX2

CDX2

PDX-1

HNF4a

NKX2.1

NKX2.2

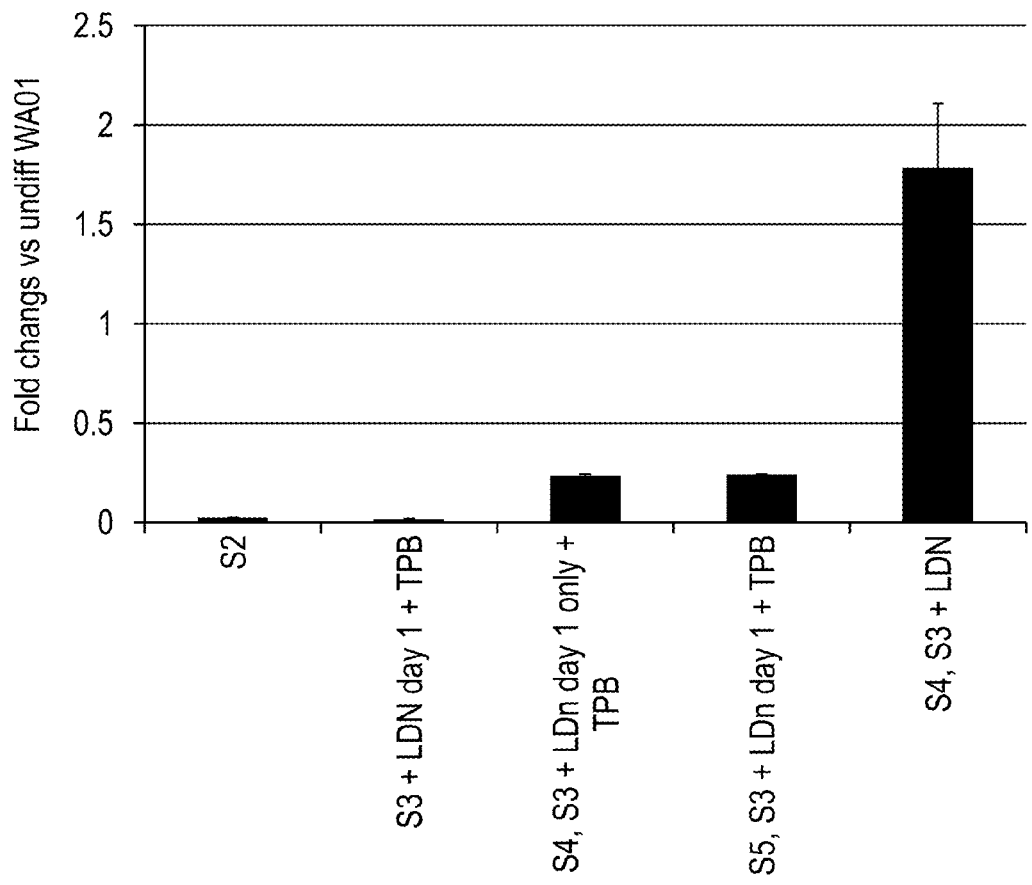

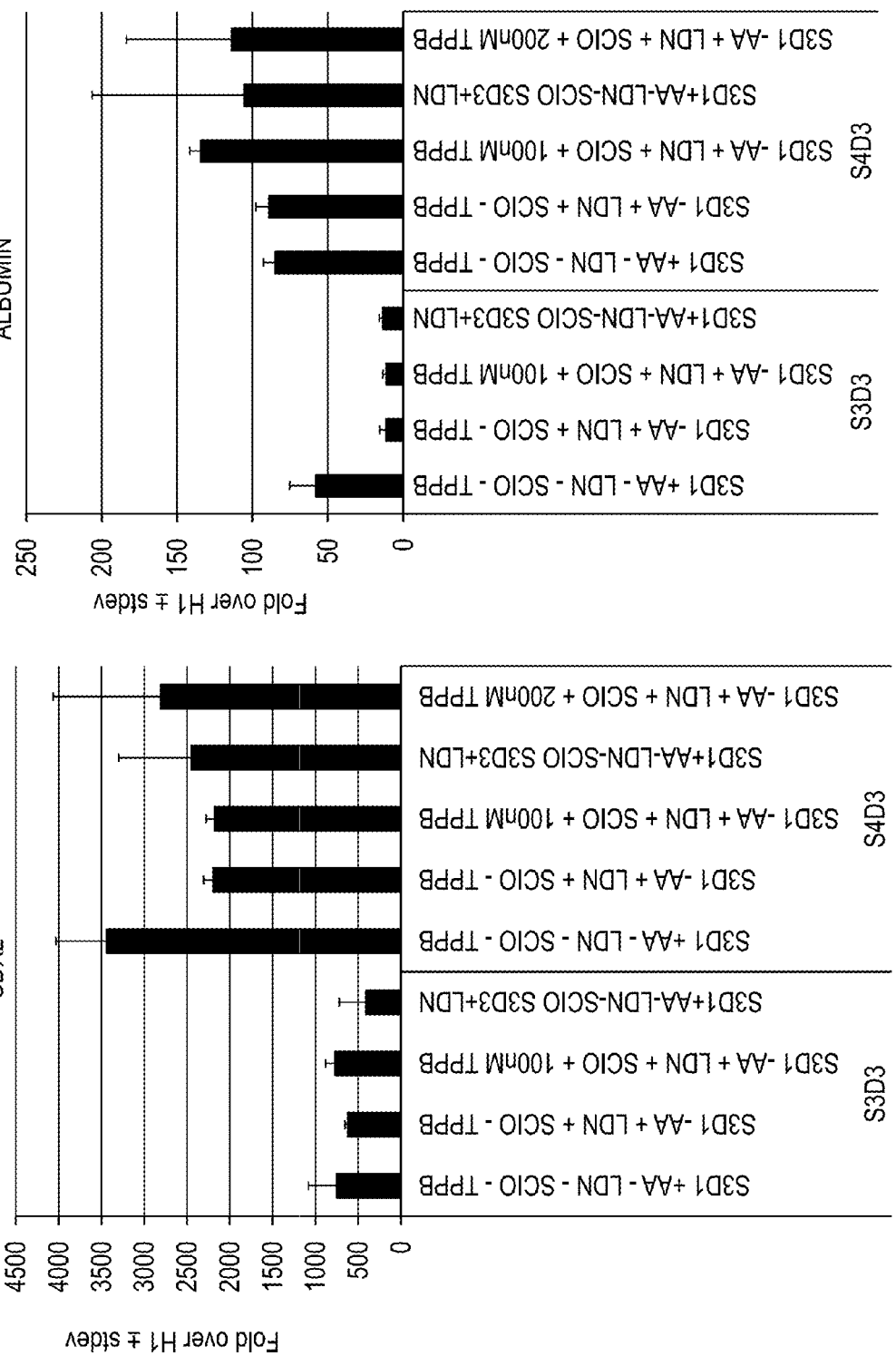

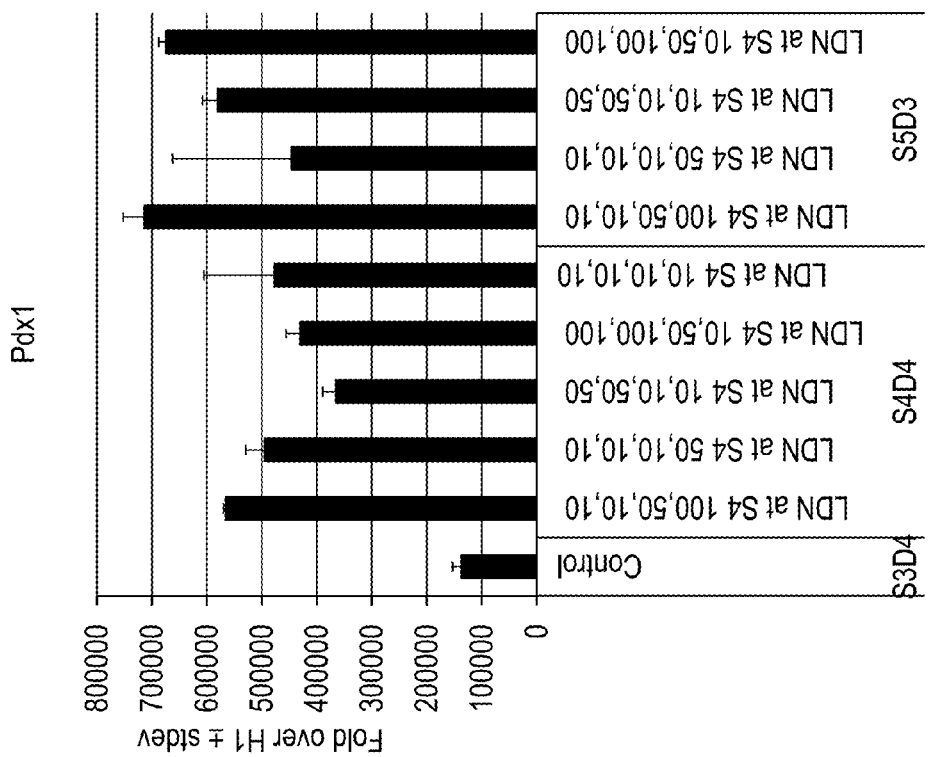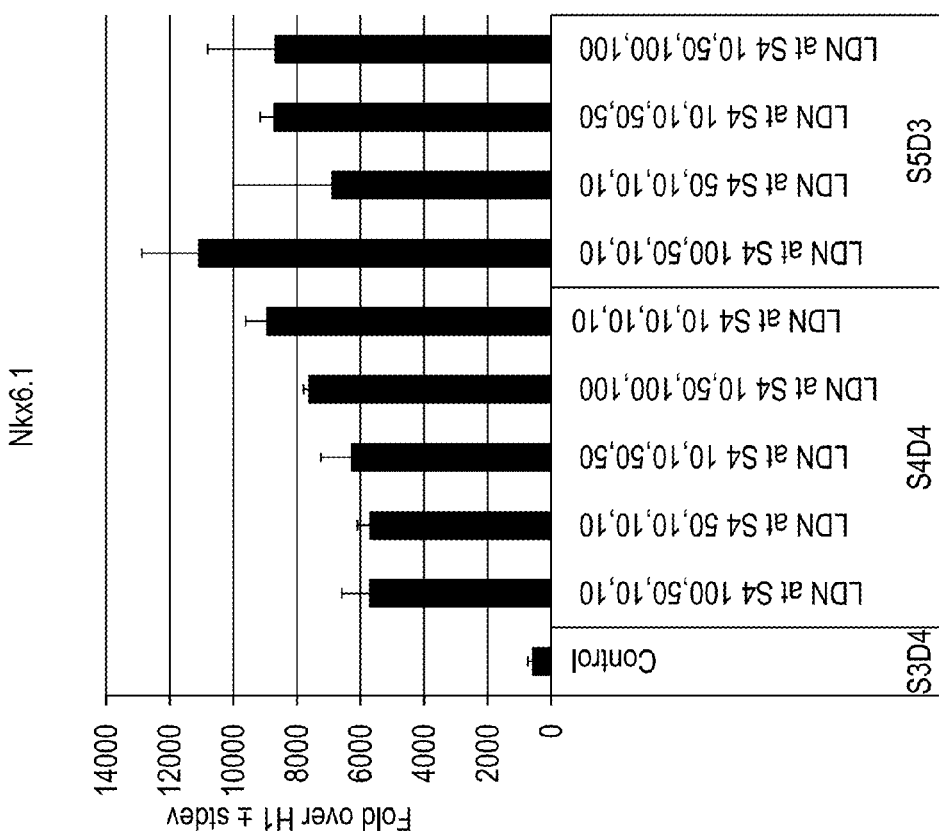

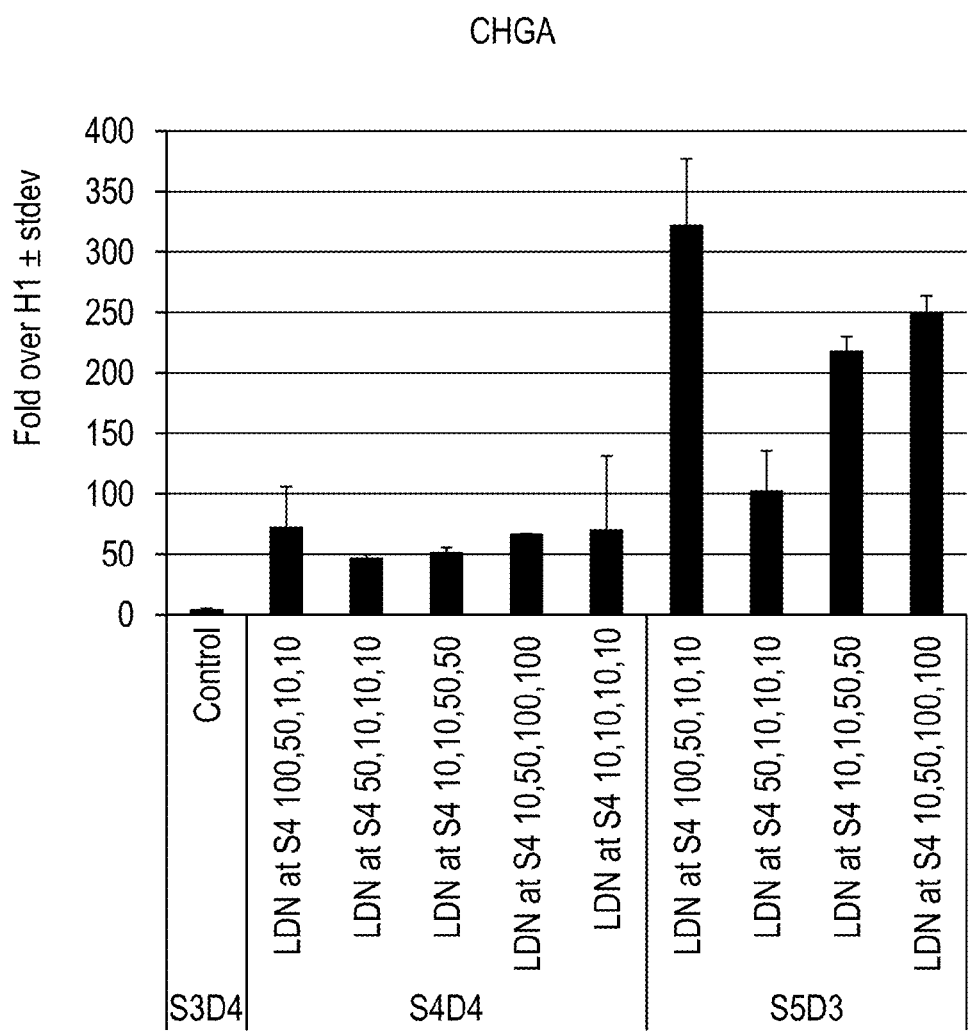

Cdx2

ALBUMIN

Nkx6.1

Pdx1

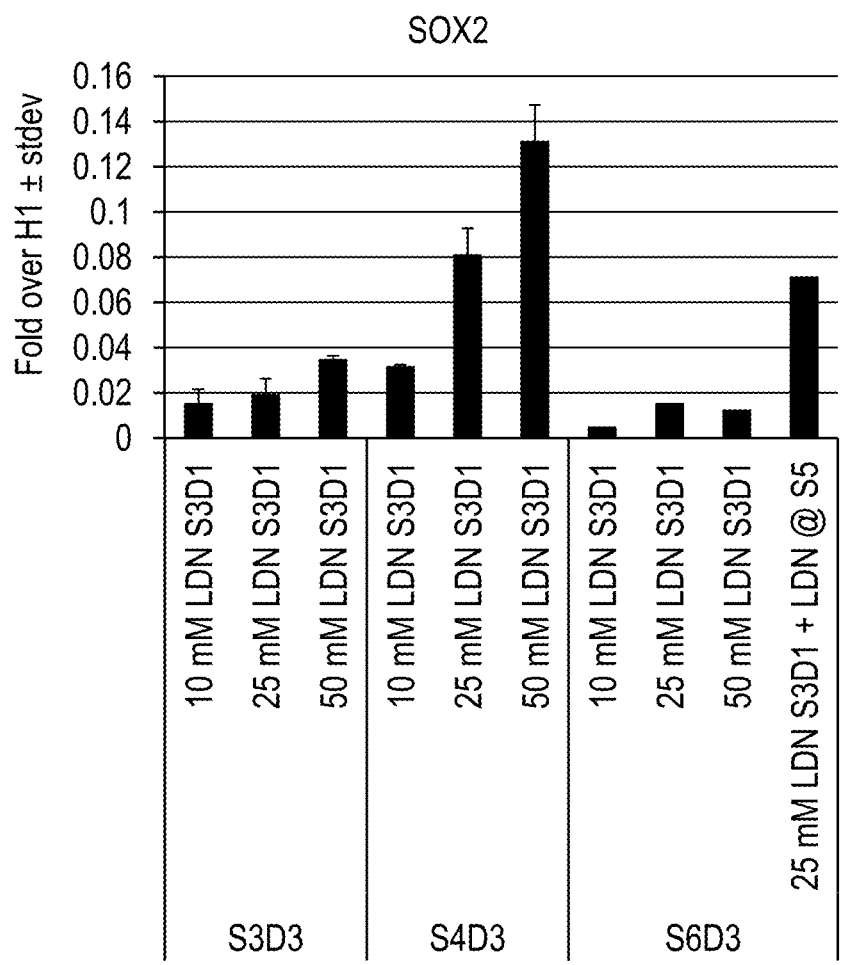

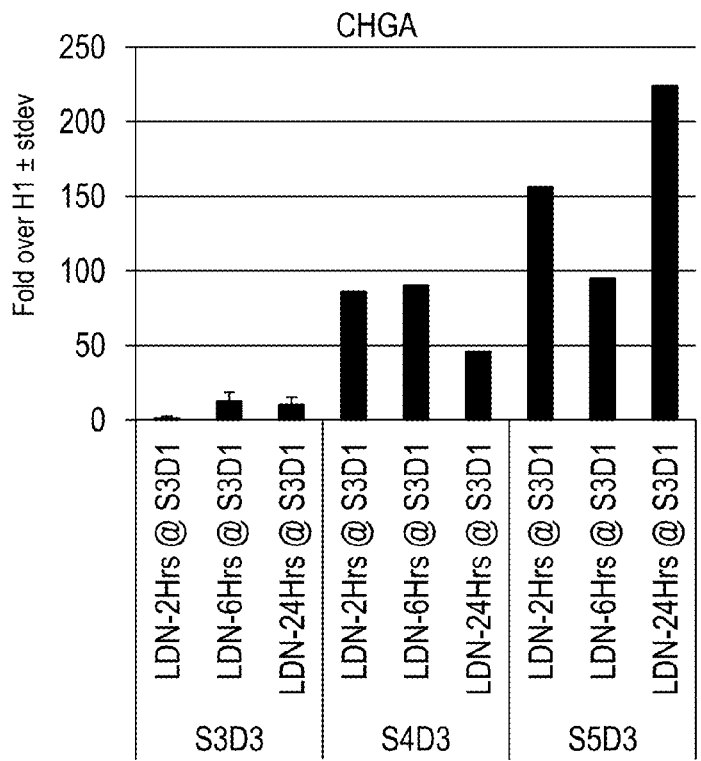
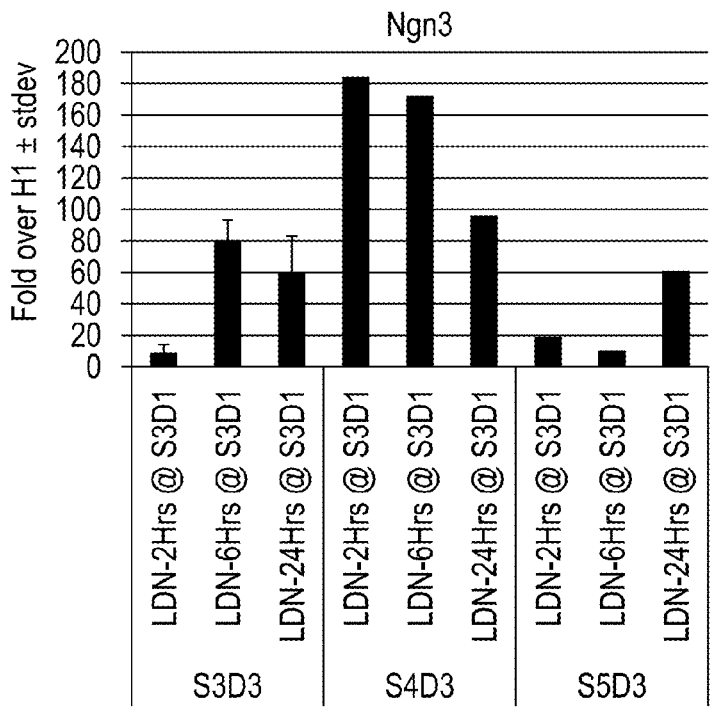

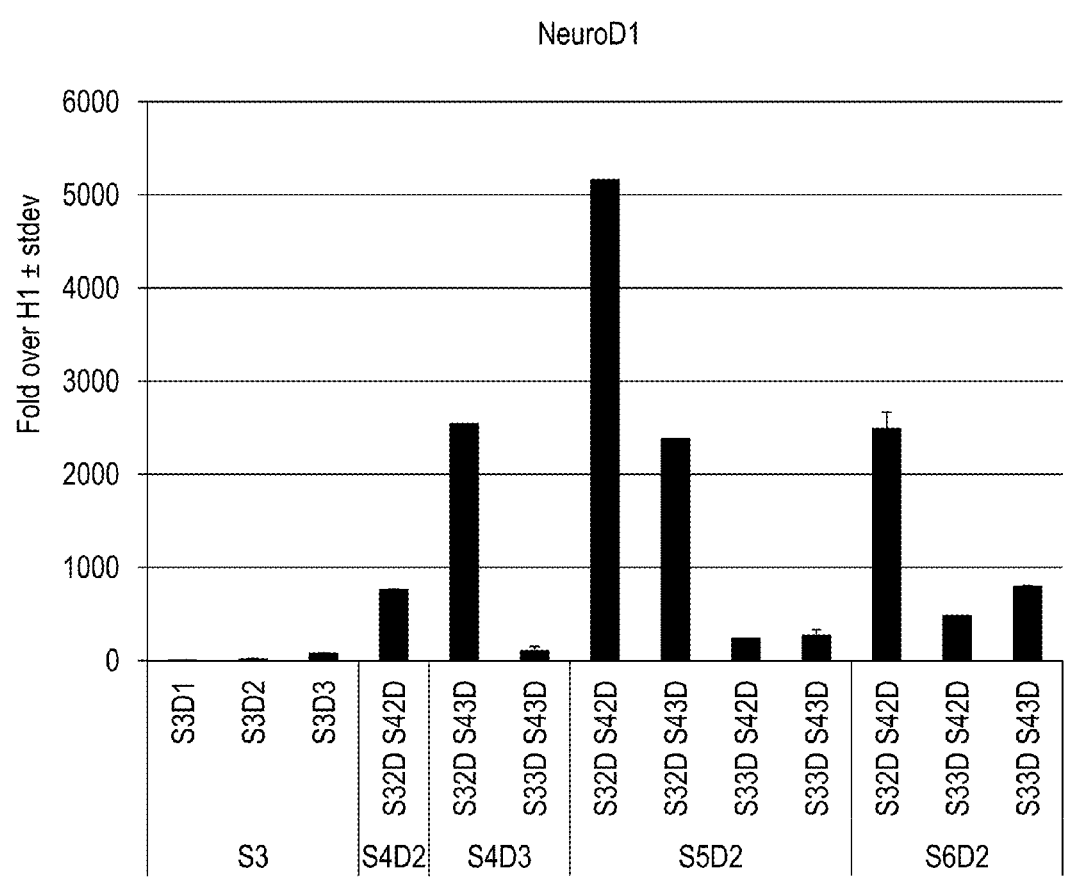

SOX2

HNF3B

CDX2

PDX-1

Isotype

NKX6.1

KI-67

Chromogranin

SOX2

CDX2

PDX-1

Isotype

NKX6.1

Chromogranin

SOX2

CDX2

PDX-1

FOXE1

IPF1

NKX6.1

PROX1

Isotype

NKX6.1

Chromogranin

SOX2

CDX2

KI-67

PDX-1

Isotype

NKX6.1

Chromogranin

SOX2

CDX2

KI-67

PDX-1

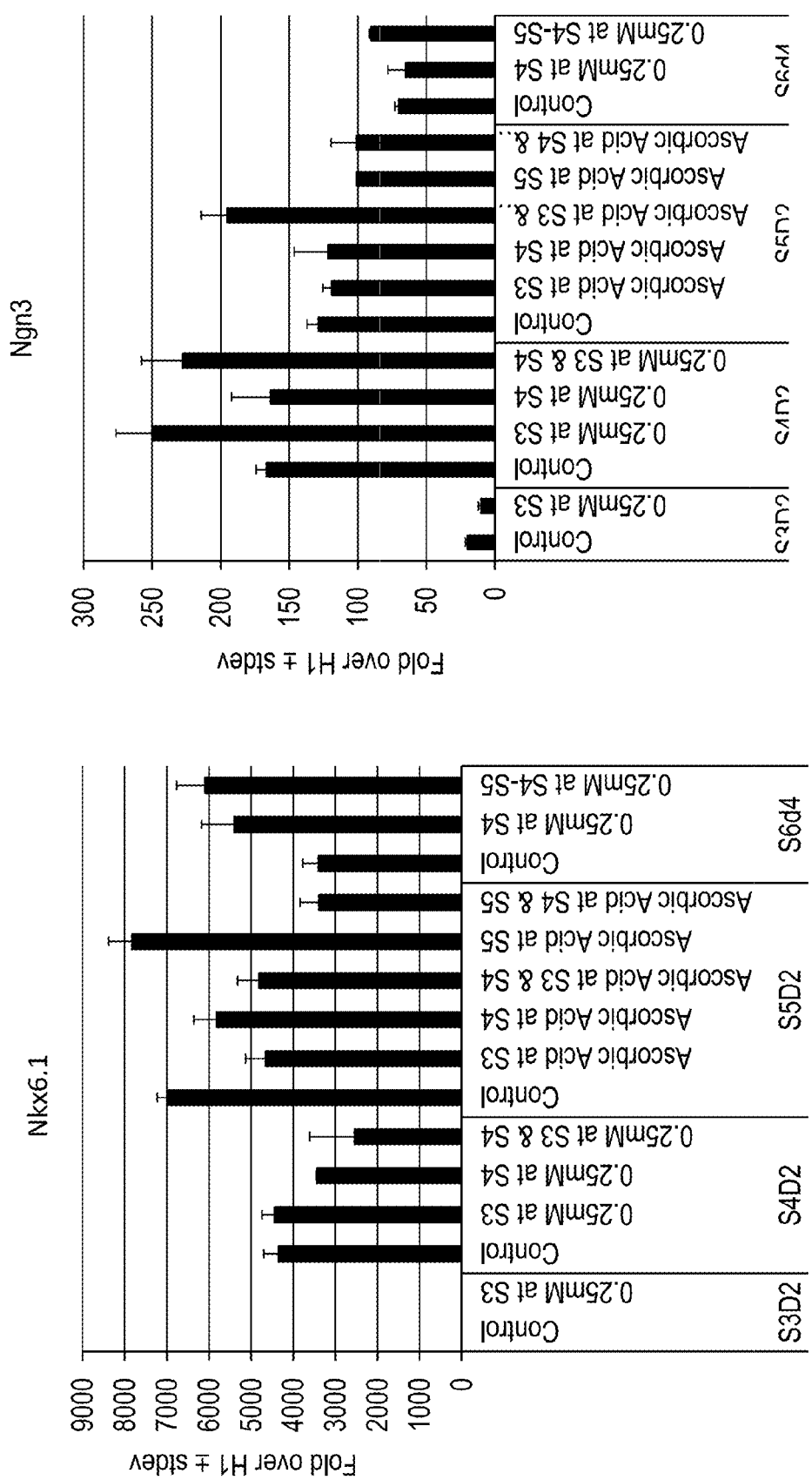

NeuroD1

Glucagon

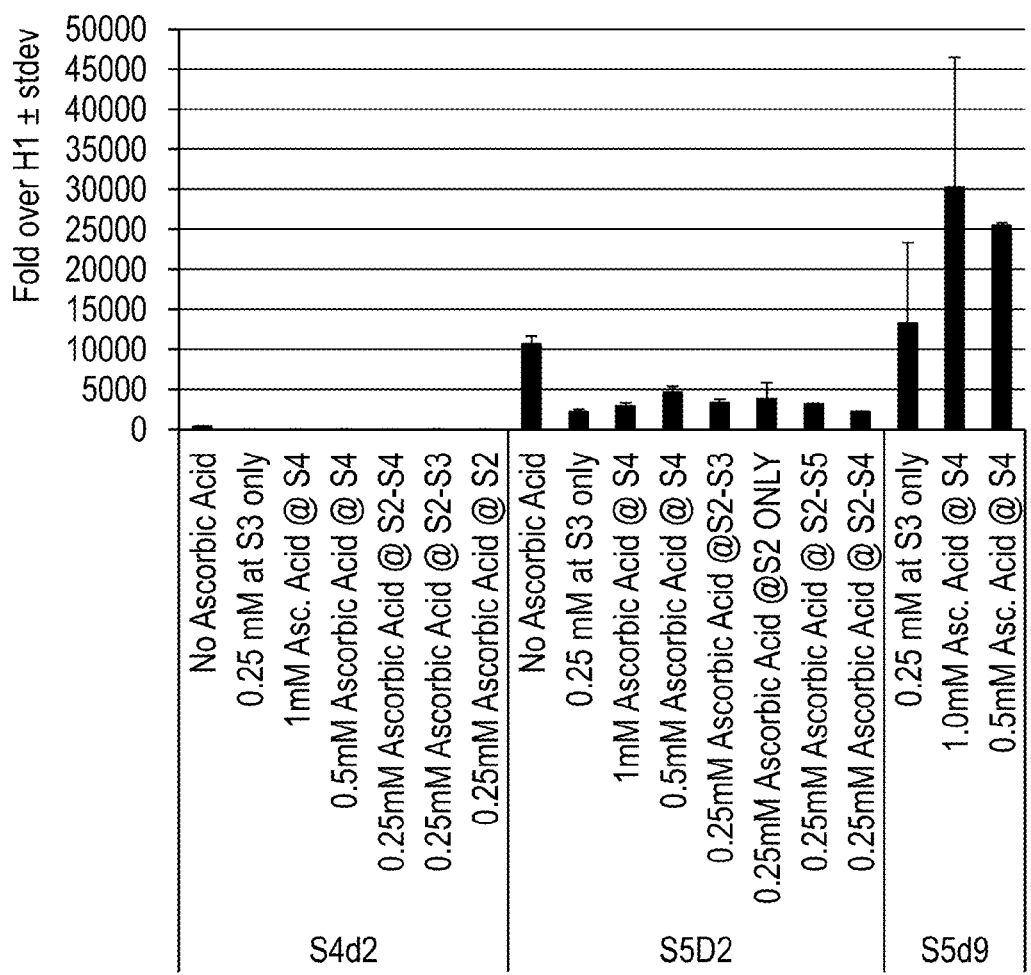

PAX4

Pax6

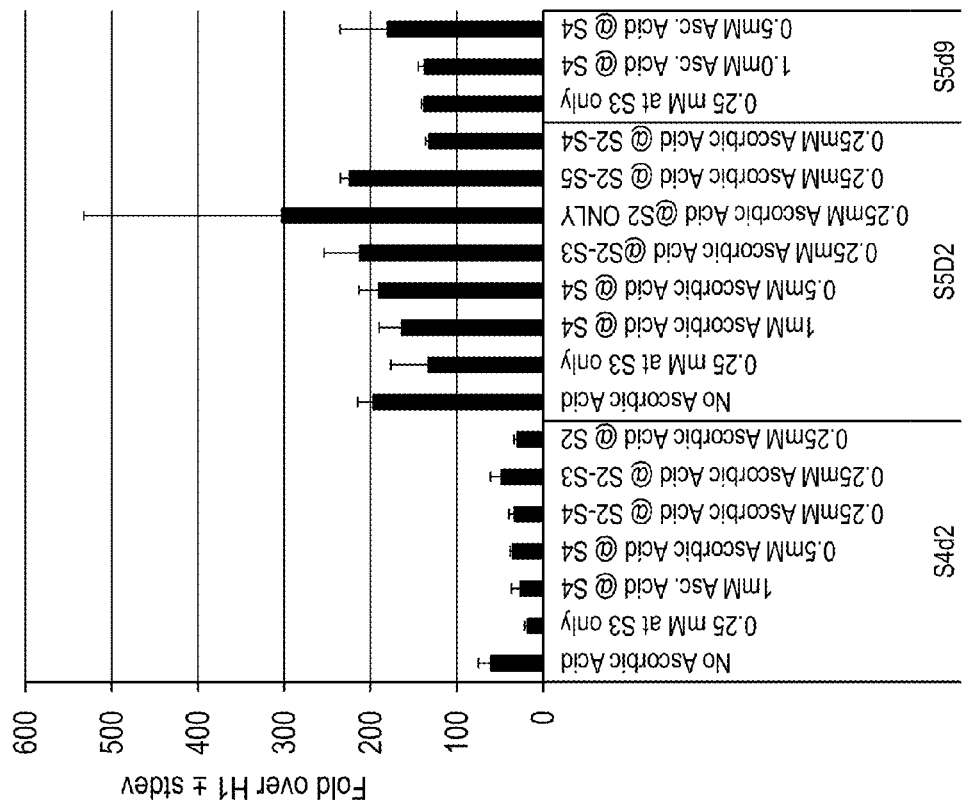
FIG. 21J CHGA
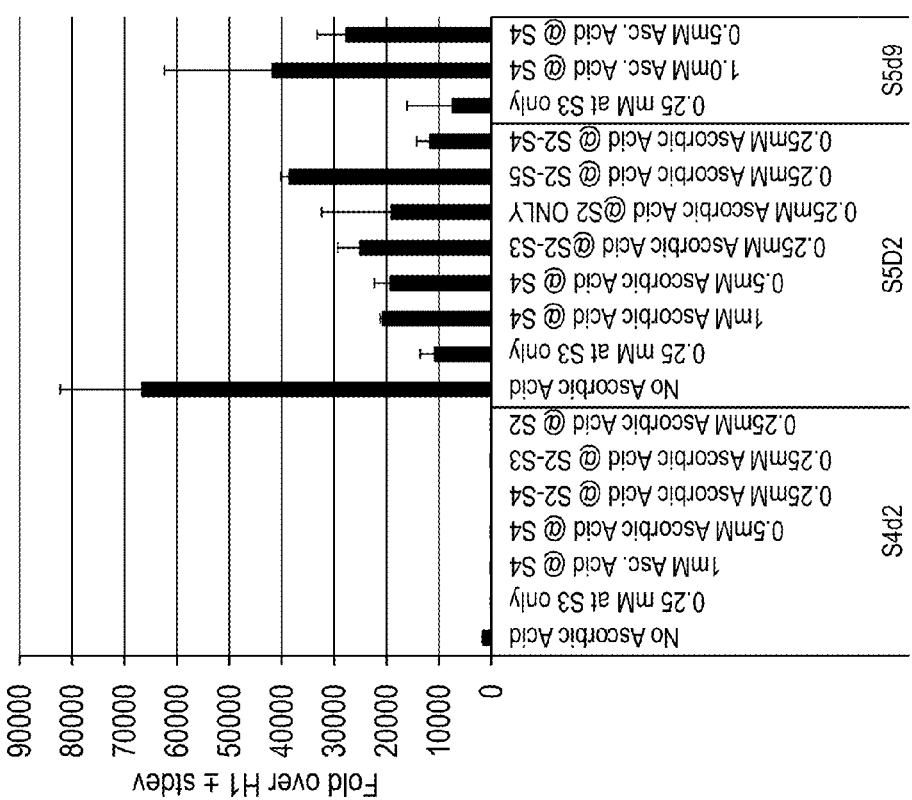
FIG. 21I Glucagon

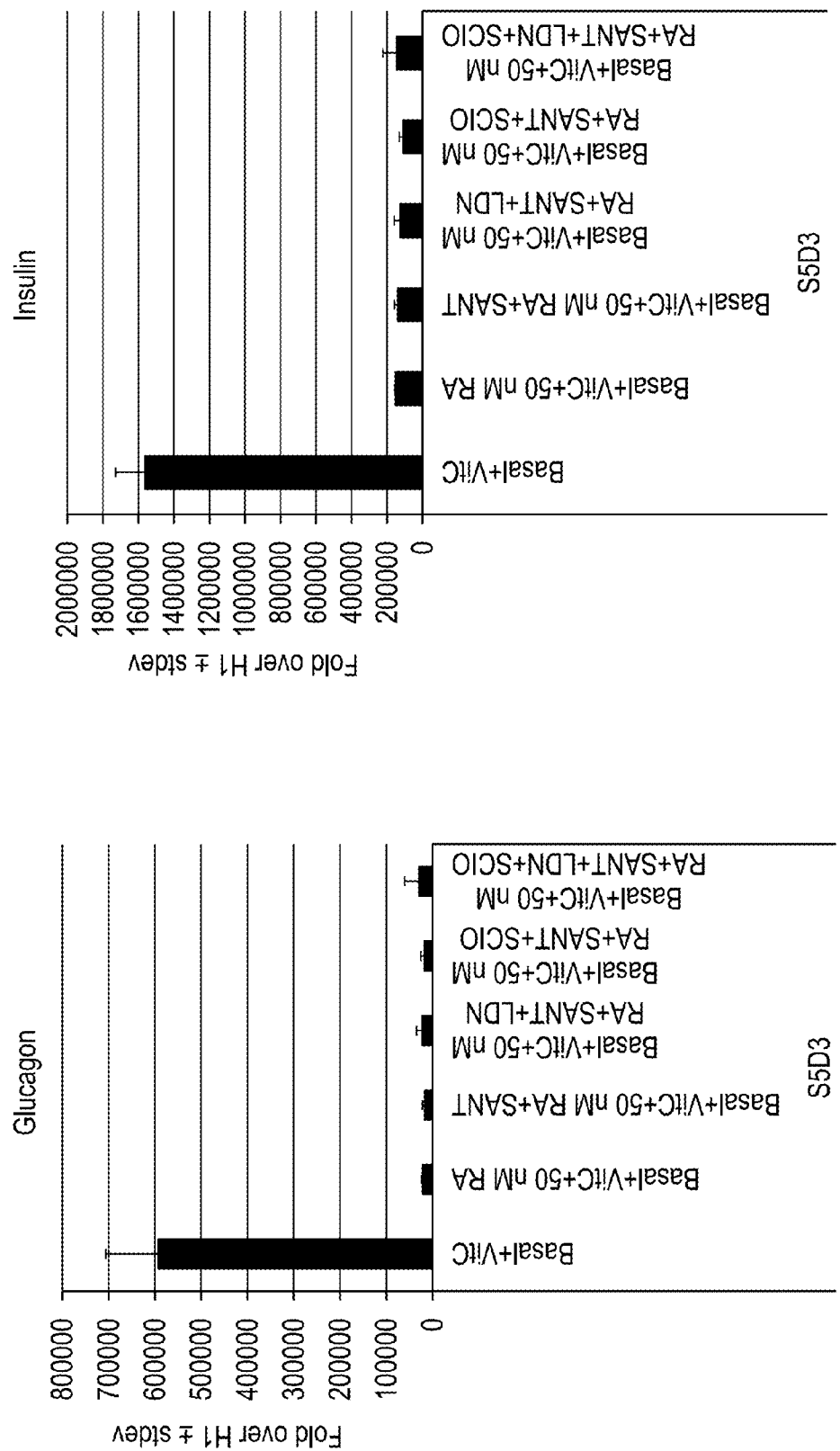

DIFFERENTIATION OF HUMAN EMBRYONIC STEM CELLS INTO SINGLE HORMONAL INSULIN POSITIVE CELLS

CROSS REFERENCE TO RELATED APPLICATION

The present application claims the benefit of U.S. Provisional Patent Application Ser. No. 61/579,351, filed Dec. 22, 2011, which is incorporated herein by reference in its entirety for all purpose.

FIELD OF THE INVENTION

The present invention is in the field of cell differentiation. More specifically, the invention provides single hormonal insulin producing cells differentiated from pluripotent stem cells using defined conditions at each step of a stepwise differentiation. Greater than 10% of the differentiated insulin producing cells in the population express markers characteristic of single hormonal pancreatic beta cells.

BACKGROUND

Advances in cell-replacement therapy for Type I diabetes mellitus and a shortage of transplantable islets of Langerhans have focused interest on developing sources of insulin-producing cells, or β cells, appropriate for engraftment. One approach is the generation of functional β cells from pluripotent stem cells, such as, for example, embryonic stem cells.

In vertebrate embryonic development, a pluripotent cell gives rise to a group of cells comprising three germ layers (ectoderm, mesoderm, and endoderm) in a process known as gastrulation. Tissues such as, thyroid, thymus, pancreas, gut, and liver, will develop from the endoderm, via an intermediate stage. An intermediate stage in this process is the formation of definitive endoderm. Definitive endoderm cells express a number of markers, such as, HNF3beta, GATA4, MIXL1, CXCR4 and SOX17.

By the end of gastrulation, the endoderm is partitioned into anterior-posterior domains that can be recognized by the expression of a panel of factors that uniquely mark anterior, mid, and posterior regions of the endoderm. For example, Hhex, and Sox2 identify the anterior region while Cdx1, 2, and 4 identify the posterior half of the endoderm.

Migration of endoderm tissue brings the endoderm into close proximity with different mesodermal tissues that help in regionalization of the gut tube. This is accomplished by a plethora of secreted factors, such as FGFs, Wnts, TGF-Bs, retinoic acid (RA), and BMP ligands and their antagonists. For example, FGF4 and BMP promote Cdx2 expression in the presumptive hindgut endoderm and repress expression of the anterior genes Hhex and SOX2 (Development 2000, 127: 1563-1567). WNT signaling has also been shown to work in parallel to FGF signaling to promote hindgut development and inhibit foregut fate (Development 2007, 134:2207-2217). Lastly, secreted retinoic acid by mesenchyme regulates the foregut-hindgut boundary (Curr Biol 2002, 12:1215-1220).

The level of expression of specific transcription factors may be used to designate the identity of a tissue. During transformation of the definitive endoderm into a primitive gut tube, the gut tube becomes regionalized into broad domains that can be observed at the molecular level by restricted gene expression patterns. For example, the regionalized pancreas domain in the gut tube shows a very high expression of PDX-1 and very low expression of CDX2 and SOX2. Similarly, the presence of high levels of Foxe1 are indicative of esophagus tissue; highly expressed in the lung tissue is NKX2.1; SOX2/Odd1 (OSR1) are highly expressed in stomach tissue; expression of PROX1/Hhex/AFP is high in liver tissue; SOX17 is highly expressed in biliary structure tissues; PDX1, NKX6.1/PTf1a, and NKX2.2 are highly expressed in pancreatic tissue; and expression of CDX2 is high in intestine tissue. The summary above is adapted from Dev Dyn 2009, 238:29-42 and Annu Rev Cell Dev Biol 2009, 25:221-251.

Formation of the pancreas arises from the differentiation of definitive endoderm into pancreatic endoderm (Annu Rev Cell Dev Biol 2009, 25:221-251; Dev Dyn 2009, 238:29-42). Dorsal and ventral pancreatic domains arise from the foregut epithelium. Foregut also gives rise to the esophagus, trachea, lungs, thyroid, stomach, liver, pancreas, and bile duct system.

Cells of the pancreatic endoderm express the pancreatic-duodenal homeobox gene PDX1. In the absence of PDX1, the pancreas fails to develop beyond the formation of ventral and dorsal buds. Thus, PDX1 expression marks a critical step in pancreatic organogenesis. The mature pancreas contains, among other cell types, exocrine tissue and endocrine tissue. Exocrine and endocrine tissues arise from the differentiation of pancreatic endoderm.

D'Amour et al. describes the production of enriched cultures of human embryonic stem cell-derived definitive endoderm in the presence of a high concentration of activin and low serum (Nature Biotechnol 2005, 23:1534-1541; U.S. Pat. No. 7,704,738). Transplanting these cells under the kidney capsule of mice resulted in differentiation into more mature cells with characteristics of endodermal tissue (U.S. Pat. No. 7,704,738). Human embryonic stem cell-derived definitive endoderm cells can be further differentiated into PDX1 positive cells after addition of FGF-10 and retinoic acid (U.S. Patent Publication No. 2005/0266554A1). Subsequent transplantation of these pancreatic precursor cells under the kidney capsule of immune deficient mice resulted in formation of functional pancreatic endocrine cells following a 3-4 month maturation phase (U.S. Pat. No. 7,993,920 and U.S. Pat. No. 7,534,608).

Fisk et al. report a system for producing pancreatic islet cells from human embryonic stem cells (U.S. Pat. No. 7,033, 831). In this case, the differentiation pathway was divided into three stages. Human embryonic stem cells were first differentiated to endoderm using a combination of sodium butyrate and activin A (U.S. Pat. No. 7,326,572). The cells were then cultured with BMP antagonists, such as Noggin, in combination with EGF or betacellulin to generate PDX1 positive cells. The terminal differentiation was induced by nicotinamide.

Small molecule inhibitors have also been used for induction of pancreatic endocrine precursor cells. For example, small molecule inhibitors of TGF-B receptor and BMP receptors (Development 2011, 138:861-871; Diabetes 2011, 60:239-247) have been used to significantly enhance number of pancreatic endocrine cells. In addition, small molecule activators have also been used to generate definitive endoderm cells or pancreatic precursor cells (Curr Opin Cell Biol 2009, 21:727-732; Nature Chem Biol 2009, 5:258-265).

Previous attempts at the induction of pancreatic precursor cells from human embryonic stem cells have highlighted the importance of co-expression of PDX-1 and NKX6.1 in correctly identifying pancreatic endoderm. However, while the art has identified the population of cells positive in expression of PDX-1 and NKX6.1 to be low or absent of CDX2 expression, previous reports have failed to test for presence of markers just anterior to the developing pancreas. SOX2, which marks the anterior endoderm, is not expressed in adult islets and is expressed at a very low level in developing pancreas (Diabetes 2005, 54:3402-4309). In contrast, some of the examples in this application disclose cell populations where at least 30% of the pancreatic endoderm cells generated from human embryonic stem cells are positive for the expression of PDX-1 and NKX6.1, and negative for the expression of CDX2 and SOX2.

All of the previous attempts to generate functional pancreatic beta cells have fallen short of attaining cells with characteristics of mature beta cells. Hallmarks of mature beta cells include expression of single hormonal insulin, correct processing of proinsulin into insulin and C-peptide, strong expression of PDX-1 and NKX6.1, appropriate insulin release in response to glucose, expression of glucose transporters, and high expression of glucokinase. All of the previous reports have resulted in endocrine cells that produce two or more of the pancreatic hormones. For example, D'Amour et al (Nature Biotech 2006, 24:1392-1401) report the generation of a cell population comprising ~10% insulin positive cells and ~20% endocrine cells as measured by synaptophysin. Similar reports by others (Cell Res 2009, 19:429-438; Stem Cells 2007, 25:1940-1953; Diabetes Obes Metab 2008, 10:186-194) have also shown differentiation of pluripotent cells to non-functional insulin positive cells. Indeed, recent studies have clearly established that transplantation of polyhormonal cells in Severe Combined ImmunoDeficiency (SCID) mice did not result in generation of functional beta cells (Diabetes 2011, 60:239-247; Nature Biotech 2011, 29:750-756). While in human fetal pancreas a fraction (~10-20%) of endocrine cells are polyhormonal cells; polyhormonal cells disappear in adult human pancreas (Histochem Cell Biol 1999, 112:147-153; J Histochem Cytochem 2009, 57:811-824).

As the burgeoning field of regenerative medicine continues to mature, a method for the formation of terminally differentiated, appropriately regulated pancreatic endocrine cells is highly desirable. We demonstrate here that with appropriate and defined manipulation of culture conditions, and precise timing of the addition of activators/inhibitors of various pathways, human embryonic stem cells can be differentiated in vitro into functional pancreatic beta cells. In particular, precise timing of BMP inhibition, using a gradient of retinoic acid along with the use of Vitamin C proved effective in generation of single hormonal pancreatic endocrine cells.

SUMMARY

The present invention provides a population of cells of the pancreatic endoderm lineage obtained in vitro by the stepwise differentiation of pluripotent cells. The medium used at each step of differentiation is supplemented with glucose. In some embodiments, at each step of differentiation the cells are cultured in medium comprising 5 mM to 20 mM glucose.

In some embodiments, differentiation of pluripotent stem cells generates a pancreatic endoderm cell population where greater than 10% of the cells in the differentiated population express markers characteristic of single hormonal pancreatic beta cells.

In some embodiments, differentiation of pluripotent stem cells generates a pancreatic endoderm cell population where greater than 30% of the differentiated population is positive for the expression of PDX-1 and NKX6.1 while being negative for the expression of CDX2 and SOX2.

In some embodiments, the stepwise differentiation comprises culturing undifferentiated human embryonic stem cells in medium further supplemented with a TGF-B ligand. In some embodiments, the stepwise differentiation comprises culturing undifferentiated human embryonic stem cells in medium further supplemented with a WNT activator. In some embodiments, the stepwise differentiation comprises culturing definitive endoderm cells in medium further supplemented with a FGF ligand. In some embodiments, the stepwise differentiation comprises culturing gut tube cells in medium further supplemented with a shh inhibitor, a FGF ligand, a PKC activator, a TGF-B ligand, a retinoid, and a gradient of a BMP inhibitor. In some embodiments, the stepwise differentiation comprises culturing posterior foregut cells in medium further supplemented with a PKC activator, a shh inhibitor, a retinoid, and a BMP inhibitor. In some embodiments, the stepwise differentiation comprises culturing cells in medium further supplemented with ascorbic acid.

In an embodiment, the invention provides an in vitro method for the stepwise differentiation of pluripotent cells into a population of cells of the pancreatic endoderm lineage, which comprises culturing the cells at each stage of differentiation in medium comprising 5 mM to 20 mM glucose. In some embodiments, the in vitro method for the stepwise differentiation of pluripotent cells further comprises differentiating the pluripotent cells into definitive endoderm (DE) cells by culturing the pluripotent cells in medium supplemented with a TGF-B ligand and a WNT activator. In some embodiments, the in vitro method for the stepwise differentiation of pluripotent cells further comprises differentiating the DE cells into gut tube cells by culturing the DE cells in medium supplemented with a FGF ligand. In some embodiments, the in vitro method for the stepwise differentiation of pluripotent cells further comprises differentiating the gut tube cells into posterior foregut endoderm cells by culturing the gut tube cells in medium supplemented with a shh inhibitor, a FGF ligand, a PKC activator, a TGF-B ligand, a retinoid, and a BMP inhibitor. In some embodiments, the in vitro method for the stepwise differentiation of pluripotent cells further comprises differentiating the gut tube cells into posterior foregut endoderm cells by culturing the gut tube cells in medium supplemented with a shh inhibitor, a FGF ligand, a PKC activator, a TGF-B ligand, a retinoid, and a BMP inhibitor. In some embodiments, the in vitro method for the stepwise differentiation of pluripotent cells further comprises differentiating the posterior foregut endoderm cells into pancreatic foregut cells by culturing the posterior foregut endoderm cells in medium supplemented with a PKC activator, a shh inhibitor, a retinoid, and a BMP inhibitor. In some embodiments, the in vitro method for the stepwise differentiation of pluripotent cells further comprises differentiating the pancreatic foregut cells into pancreatic endoderm cells by culturing the pancreatic foregut cells in medium supplemented with a shh inhibitor, a TGF-B inhibitor, and a retinoid. In some embodiments, the in vitro method for the stepwise differentiation of pluripotent cells further comprises differentiating the pancreatic endoderm cells into a pancreatic beta cell population.

In an embodiment, in at least one step of the in vitro method for the stepwise differentiation of pluripotent cells the medium is further supplemented with ascorbic acid. In some embodiments, greater than 10% of the cells in the differentiated population are single hormonal insulin positive cells. In some embodiments, greater than 30% of pancreatic endoderm cells in culture generated by the methods of the invention are PDX-1+, NKX6.1+, SOX2−, and CDX2−.

In an embodiment, the invention relates to an in vitro method for differentiating human embryonic stem cells into pancreatic beta cells comprising: a) culturing undifferentiated human embryonic stem cells in medium supplemented with glucose, a TGF-B ligand, and a WNT activator, to generate a population of definite endoderm (DE) cells; b) culturing the DE cells in medium supplemented with glucose, and a FGF ligand to generate a population of gut tube cells; c) culturing the gut tube cells in medium supplemented with glucose, a shh inhibitor, a FGF ligand, a PKC activator, a TGF-B ligand, a retinoid, and a gradient of a BMP inhibitor to generate a population of posterior foregut endoderm cells expressing PDX-1 and SOX2; d) culturing the posterior foregut cells in medium supplemented with glucose, a PKC activator, a shh inhibitor, a retinoid, and a BMP inhibitor to generate a population of pancreatic foregut cells expressing PDX-1 and NKX6.1, and expressing lower level of SOX2 as compared to the posterior foregut cells; e) culturing the pancreatic foregut cells in medium supplemented with glucose, a shh inhibitor, a TGF-B inhibitor, and a retinoid to obtain a population of pancreatic endoderm cells expressing PDX-1, a higher level of NKX6.1, and a lower level of SOX2 as compared to pancreatic foregut cells; and f) differentiating the pancreatic endoderm cells into a pancreatic beta cell population. In some embodiments, the pancreatic beta cell population generated by the methods of the invention is PDX-1+, NKX6.1+, SOX2−, and CDX2−. In some embodiments the medium in at least one step of the stepwise differentiation method is further supplemented with ascorbic acid. In some embodiments, the pancreatic beta cells obtained by the methods of the invention are single hormonal insulin-producing cells which are also NKX6.1+ and PDX-1+.

BRIEF DESCRIPTION OF THE DRAWINGS

FIG. 1A: Isotype control; FIG. 1B: chromogranin; FIG. 1C: KI-67; FIG. 1D: NKX6.1; FIG. 1E: SOX2; FIG. 1F: CDX2; FIG. 1G: PDX-1. Percentage expression for each marker is shown on each histogram.

FIG. 2A to FIG. 2G show the FACS histogram expression profiles of the following markers in cells differentiated according to Example 1, and harvested at S4 day 2. FIG. 2A: Isotype control; FIG. 2B: chromogranin; FIG. 2C: KI-67; FIG. 2D: NKX6.1; FIG. 2E: SOX2; FIG. 2F: CDX2; FIG. 2G: PDX-1. Percentage expression for each marker is shown on each histogram.

FIG. 3A: Isotype control; FIG. 3B: chromogranin; FIG. 3C: KI-67; FIG. 3D: NKX6.1; FIG. 3E: SOX2; FIG. 3F: CDX2; FIG. 3G: PDX-1. Percentage expression for each marker is shown on each histogram.

FIG. 4A to FIG. 4G show FACS histogram expression profiles of the following markers of cells differentiated according to Example 1 and harvested at S5 day 7. FIG. 4A: Isotype control; FIG. 4B: chromogranin; FIG. 4C: KI-67; FIG. 4D: NKX6.1; FIG. 4E: SOX2; FIG. 4F: CDX2; FIG. 4G: PDX-1. Percentage expression for each marker is shown on each histogram.

FIG. 5A: chromogranin (y-axis) and CDX2 (x axis); FIG. 5B: chromogranin (y-axis) and SOX2 (x axis); FIG. 5C: chromogranin (y-axis) and NKX6.1 (x axis). Percentage co-expression for each plot is shown on each histogram.

FIG. 6A: CDX2; FIG. 6K: PTF1a; FIG. 6T: somatostatin.

FIG. 7A: NKX6.1; FIG. 7B: PDX-1; FIG. 7C: chromogranin; FIG. 7D: NGN3; FIG. 7E: CDX2; FIG. 7F: albumin; FIG. 7G: SOX2.

FIG. 8A to FIG. 8G depict data from real-time PCR analyses of the expression of the following markers in H1 cells differentiated according to Example 3 and harvested at S2, S3, S4, or S5. FIG. 8A: NKX6.1; FIG. 8B: PDX-1; FIG. 8C: NGN3; FIG. 8D: NeuroD; FIG. 8E: chromogranin; FIG. 8F: CDX2; FIG. 8G: SOX2.

FIG. 9A to FIG. 9H depict data from real-time PCR analyses of the expression of the following markers in H1 cells differentiated according to Example 4 and harvested at day 4 of S3 and S4. FIG. 9A: NKX6.1; FIG. 9B: PDX-1; FIG. 9C: chromogranin; FIG. 9D: NGN3; FIG. 9E: NeuroD; FIG. 9F: CDX2; FIG. 9G: albumin; FIG. 9H: SOX2.

FIG. 10A to FIG. 10H depict data from real-time PCR analyses of the expression of the following genes in cells of the human embryonic stem cell line H1 differentiated according to the Example 5 and harvested at stage 4. FIG. 10A: NKX6.1; FIG. 10B: PDX-1; FIG. 10C: chromogranin; FIG. 10D: NGN3; FIG. 10E: NeuroD; FIG. 10F: CDX2; FIG. 10G: albumin; FIG. 10H: SOX2.

FIG. 11A to FIG. 11H show data from real-time PCR analysis of the expression of the following genes in cells of the human embryonic stem cell line H1 differentiated according to the Example 6 and harvested at day 3 of S3 or S6. FIG. 11A: NKX6.1; FIG. 11B: PDX-1; FIG. 11C: chromogranin; FIG. 11D: NGN3; FIG. 11E: NeuroD; FIG. 11F: CDX2; FIG. 11G: albumin; FIG. 11H: SOX2.

FIG. 12A to FIG. 12G depict data from real-time PCR analysis of the expression of the following genes in cells of the human embryonic stem cell line H1 differentiated according to the Example 7 and harvested at day 3 of S3, S4, or S5. FIG. 12A: NKX6.1; FIG. 12B: PDX-1; FIG. 12C: chromogranin; FIG. 12D: NGN3; FIG. 12E: NeuroD; FIG. 12F: CDX2; FIG. 12G: SOX2.

FIG. 13A to FIG. 13G depict data from real-time PCR analyses of the expression of the following genes in cells of the human embryonic stem cell line H1 differentiated according to the Example 8 and harvested at S3, S4, S5, or S6. FIG. 13A: NKX6.1; FIG. 13B: PDX-1; FIG. 13C: chromogranin; FIG. 13D: NGN3; FIG. 13E: NeuroD; FIG. 13F: CDX2; FIG. 13G: SOX2.

FIG. 14A: Isotype control; FIG. 14B: chromogranin; FIG. 14C: KI-67; FIG. 14D: NKX6.1; FIG. 14E: SOX2; FIG. 14F: HNF3B; FIG. 14G: CDX2; FIG. 14H: PDX-1. Percentage expression for each marker is shown on each histogram.

FIG. 15A: Isotype control; FIG. 15B: NKX6.1; FIG. 15C: KI-67; FIG. 15D: chromogranin; FIG. 15E: SOX2; FIG. 15F CDX2; FIG. 15G: PDX-1. Percentage expression for each marker is shown on each histogram.

FIG. 16A: Isotype control; FIG. 16B: NKX6.1; FIG. 16C: chromogranin; FIG. 16D: SOX2; FIG. 16E: CDX2; FIG. 16F: PDX-1. Percentage expression for each marker is shown on each histogram.

FIG. 17A: CDX2; FIG. 17B: HHex; FIG. 17C: FOXE1; FIG. 17D: IPF1 (PDX-1); FIG. 17E: NKX2.1; FIG. 17F: NKX2.2; FIG. 17G: NKX6.1; FIG. 17H: PROX1; FIG. 17I: SOX2; FIG. 17J: SOX9.

FIG. 18A: Isotype control; FIG. 18B: NKX6.1; FIG. 18C: chromogranin; FIG. 18D: SOX2; FIG. 18E: CDX2; FIG. 18F: KI-67; FIG. 18G: PDX-1. Percentage expression for each marker is shown on each histogram.

FIG. 19A: Isotype control; FIG. 19B: NKX6.1; FIG. 19C: chromogranin; FIG. 19D: SOX2; FIG. 19E: CDX2; FIG. 19F: KI-67; FIG. 19G: PDX-1. Percentage expression for each marker is shown on each histogram.

FIG. 20A to FIG. 20J show real-time PCR analysis of the expression of the following genes in cells of the human embryonic stem cell line H1 differentiated according to the Example 11. FIG. 20A: somatostatin; FIG. 20B: PDX1; FIG. 20C: Pax6; FIG. 20D: Pax4; FIG. 20E: NKX6.1; FIG. 20F: NGN3; FIG. 20G: glucagon; FIG. 20H: NeuroD; FIG. 20I: insulin; FIG. 20J: chromogranin.

FIG. 21A to FIG. 21J show data from real-time PCR analysis of the expression of the following genes in cells of the human embryonic stem cell line H1 differentiated according to the Example 12 and harvested at S4 day 2, S5 day 2, and S5 day 9. FIG. 21A: somatostatin; FIG. 21B: PDX1; FIG. 21C: Pax6; FIG. 21D: Pax4; FIG. 21E: NKX6.1; FIG. 21F: NGN3; FIG. 21G: NeuroD; FIG. 21H: insulin; FIG. 21I: glucagon; FIG. 21J: chromogranin.

FIG. 22A to FIG. 22L show data from real-time PCR analyses of the expression of the following genes in cells of the embryonic stem cell line H1 differentiated according to example 13 and harvested at S5 day 3. FIG. 22A: Pax4; FIG. 22B: Pax6; FIG. 22C: PDX1; FIG. 22D: PTF1a; FIG. 22E: glucagon; FIG. 22F: insulin; FIG. 22G: NeuroD; FIG. 22H: ngn3; FIG. 22I: Zic1; FIG. 22J: CDX2; FIG. 22K: albumin; FIG. 22L: NKX6.1.

DETAILED DESCRIPTION

Figure 1A:
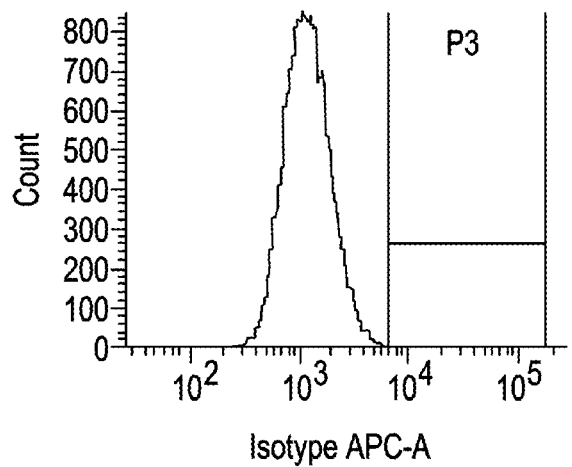
FIG. 1A to FIG. 1G show the FACS histogram expression profiles of the following markers at S3 day 2 of cells differentiated according to Example 1.

For clarity of disclosure, and not by way of limitation, the detailed description of the invention is divided into the following subsections that describe or illustrate certain features, embodiments or applications of the present invention.

DEFINITIONS

Stem cells are undifferentiated cells defined by their ability, at the single cell level, to both self-renew and differentiate. Stem cells may produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm). Stem cells also give rise to tissues of multiple germ layers following transplantation and contribute substantially to most, if not all, tissues following injection into blastocysts.

Stem cells are classified by their developmental potential as: (1) totipotent, meaning able to give rise to all embryonic and extraembryonic cell types; (2) pluripotent, meaning able to give rise to all embryonic cell types; (3) multipotent, meaning able to give rise to a subset of cell lineages but all within a particular tissue, organ, or physiological system (for example, hematopoietic stem cells (HSC) can produce progeny that include HSC (self-renewal), blood cell restricted oligopotent progenitors, and all cell types and elements (e.g., platelets) that are normal components of the blood); (4) oligopotent, meaning able to give rise to a more restricted subset of cell lineages than multipotent stem cells; and (5) unipotent, meaning able to give rise to a single cell lineage (e.g., spermatogenic stem cells).

Differentiation is the process by which an unspecialized ("uncommitted") or less specialized cell acquires the features of a specialized cell such as, for example, a nerve cell or a muscle cell. A differentiated cell or a differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. "De-differentiation" refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

"Markers", as used herein, are nucleic acid or polypeptide molecules that are differentially expressed in a cell of interest. In this context, differential expression means an increased level for a positive marker and a decreased level for a negative marker. The detectable level of the marker nucleic acid or polypeptide is sufficiently higher or lower in the cells of interest compared to other cells, such that the cell of interest can be identified and distinguished from other cells using any of a variety of methods known in the art.

As used herein, a cell is "positive for" a specific marker or "positive" when the specific marker is detected in the cell. Similarly, the cell is "negative for" a specific marker, or "negative" when the specific marker is not detected in the cell.

As used herein, "stage 1" and "S1" are used interchangeably to identify cells expressing markers characteristic of the definitive endoderm (DE).

"Definitive endoderm", as used herein, refers to cells which bear the characteristics of cells arising from the epiblast during gastrulation and which form the gastrointestinal tract and its derivatives. Definitive endoderm cells express at least one of the following markers: HNF3 beta, GATA4, SOX17, CXCR4, Cerberus, OTX2, goosecoid, C-Kit, CD99, and MIXL1.

"Gut tube", as used herein, refers to cells derived from definitive endoderm that express at least one of the following markers: HNF3-beta, HNF1-beta, or HNF4-alpha. Gut tube cells can give rise to all endodermal organs, such as lungs, liver, pancreas, stomach, and intestine.

Used herein interchangeably are "stage 2" and "S2" which identify cells expressing markers characteristic of the primitive gut tube.

"Foregut endoderm" refers to endoderm cells that give rise to esophagus, lungs, stomach, liver, pancreas, gall bladder, and a portion of the duodenum.

"Posterior foregut" refers to endoderm cells that can give rise to posterior stomach, pancreas, liver, and a portion of the duodenum.

"Mid-gut endoderm" refers to endoderm cells that can give rise to the intestines, portions of the duodenum, appendix, and ascending colon.

"Hind-gut endoderm" refers to endoderm cells that can give rise to the distal third of the transverse colon, the descending colon, sigmoid colon and rectum.

Both "stage 3" and "S3" are used interchangeably to identify cells expressing markers characteristic of the foregut endoderm. "Cells expressing markers characteristic of the foregut lineage", as used herein, refers to cells expressing at least one of the following markers: PDX-1, FOXA2, CDX2, SOX2, and HNF4 alpha.

Used interchangeably herein are "stage 4" and "S4" to identify cells expressing markers characteristic of the pancreatic foregut precursor. "Cells expressing markers characteristic of the pancreatic foregut precursor lineage", as used herein, refers to cells expressing at least one of the following markers: PDX-1, NKX6.1, HNF6, FOXA2, PTF1a, Prox1 and HNF4 alpha.

As used herein, "stage 5" and "S5" are used interchangeably to identify cells expressing markers characteristic of the pancreatic endoderm and pancreatic endocrine precursor cells. "Cells expressing markers characteristic of the pancreatic endoderm lineage", as used herein, refers to cells expressing at least one of the following markers: PDX1, NKX6.1, HNF1 beta, PTF1 alpha, HNF6, HNF4 alpha, SOX9, HB9 or PROX1. Cells expressing markers characteristic of the pancreatic endoderm lineage do not substantially express CDX2 or SOX2.

As used herein, "stage 6" and "S6" are used interchangeably to identify cells enriched in pancreatic endocrine cells.

"Pancreatic endocrine cell", or "Pancreatic hormone expressing cell", or "Cells expressing markers characteristic of the pancreatic endocrine lineage" as used herein, refers to a cell capable of expressing at least one of the following hormones: insulin, glucagon, somatostatin, ghrelin, and pancreatic polypeptide.

"Pancreatic endocrine precursor cell" or "Pancreatic endocrine progenitor cell" refers to pancreatic endoderm cells capable of becoming a pancreatic hormone expressing cell. Such a cell can express at least one of the following markers: NGN3, NKX2.2, NeuroD, ISL-1, Pax4, Pax6, or ARX.

"Functional pancreatic beta cell" as used herein, refers to a single hormonal insulin positive cell capable of being glucose responsive and positive for PDX-1 and NKX6.1.

Used interchangeably herein are "d1", "d 1", and "day 1"; "d2", "d 2", and "day 2"; "d3", "d 3", and "day 3", and so on. These number letter combinations specify the day of incubation in the different stages during the stepwise differentiation protocol of the instant application.

"Ascorbic acid" and "Vitamin C" are used interchangeably herein and relate to an essential nutrient for humans and other animal species.

"Glucose" and "D-Glucose" are used interchangeably herein and refer to dextrose, a sugar commonly found in nature.

A cell "positive" for a specific marker or which is marker "+" (i.e., PDX-1+) is a cell in which the particular marker may be detected. A cell "negative" for a specific marker or which is marker "−" (i.e., NKX6.1−) is a cell in which the marker is not detected by the methods taught in the instant specification.

In the instant application "chromogranin" and "CHGN" are used interchangeably to identify the gene endcoding the acidic secretory glycoprotein chromogranin.

Used interchangeably herein are "NeuroD" and "NeuroD1" which identify a protein expressed in pancreatic endocrine progenitor cells and the gene encoding it.

Used interchangeably herein are "LDN" and "LDN-193189" to indicate a BMP receptor inhibitor available from Stemgent, Calif., USA.

Isolation, Expansion and Culture of Pluripotent Stem Cells

Pluripotent stem cells may express one or more of the stage-specific embryonic antigens (SSEA) 3 and 4, and markers detectable using antibodies designated Tra-1-60 and Tra-1-81 (Thomson et al., Science 282:1145, 1998). Differentiation of pluripotent stem cells in vitro results in the loss of SSEA-4, Tra-1-60, and Tra-1-81 expression. Undifferentiated pluripotent stem cells typically have alkaline phosphatase activity, which can be detected by fixing the cells with 4% paraformaldehyde, and then developing with Vector Red as a substrate, as described by the manufacturer (Vector Laboratories, CA, USA). Undifferentiated pluripotent stem cells also typically express OCT4 and TERT, as detected by RT-PCR.

Another desirable phenotype of propagated pluripotent stem cells is a potential to differentiate into cells of all three germinal layers: endoderm, mesoderm, and ectoderm tissues. Pluripotency of stem cells can be confirmed, for example, by injecting cells into SCID mice, fixing the teratomas that form using 4% paraformaldehyde, and then examining them histologically for evidence of cell types from the three germ layers. Alternatively, pluripotency may be determined by the creation of embryoid bodies and assessing the embryoid bodies for the presence of markers associated with the three germinal layers.

Propagated pluripotent stem cell lines may be karyotyped using a standard G-banding technique and compared to published karyotypes of the corresponding primate species. It is desirable to obtain cells that have a "normal karyotype," which means that the cells are euploid, wherein all human chromosomes are present and not noticeably altered. Pluripotent cells may be readily expanded in culture using various feeder layers or by using matrix protein coated vessels. Alternatively, chemically defined surfaces in combination with defined media such as mTesr™1 media (StemCell Technologies, Vancouver, Canada) may be used for routine expansion of the cells. Pluripotent cells may be readily removed from culture plates using enzymatic, mechanical or use of various calcium chelators such as EDTA (Ethylenediaminetetraacetic acid). Alternatively, pluripotent cells may be expanded in suspension in the absence of any matrix proteins or a feeder layer.

Sources of Pluripotent Stem Cells

The types of pluripotent stem cells that may be used include established lines of pluripotent cells derived from tissue formed after gestation, including pre-embryonic tissue (such as, for example, a blastocyst), embryonic tissue, or fetal tissue taken any time during gestation, typically but not necessarily, before approximately 10 to 12 weeks gestation. Non-limiting examples are established lines of human embryonic stem cells (hESCs) or human embryonic germ cells, such as, for example the human embryonic stem cell lines H1, H7, and H9 (WiCell Research Institute, Madison, Wis., USA). Also suitable are cells taken from a pluripotent stem cell population already cultured in the absence of feeder cells. Also suitable are inducible pluripotent cells (IPS) or reprogrammed pluripotent cells that can be derived from adult somatic cells using forced expression of a number of pluripotent related transcription factors, such as OCT4, Nanog, Sox2, KLF4, and ZFP42 (Annu Rev Genomics Hum Genet, 2011, 12:165-185). The human embryonic stem cells used in the methods of the invention may also be prepared as described by Thomson et al. (U.S. Pat. No. 5,843,780; Science, 1998, 282:1145; Curr. Top. Dev. Biol., 1998, 38:133; Proc. Natl. Acad. Sci. U.S.A., 1995: 92:7844).

Formation of Cells Expressing Markers
Characteristic of the Pancreatic Endoderm Lineage
from Pluripotent Stem Cells Characteristics of pluripotent stem cells are well known to those skilled in the art, and additional characteristics of pluripotent stem cells continue to be identified. Pluripotent stem cell markers include, for example, the expression of one or more of the following: ABCG2, cripto, FOXD3, CONNEXIN43, CONNEXIN45, OCT4, SOX2, NANOG, hTERT, UTF1, ZFP42, SSEA-3, SSEA-4, Tra 1-60, Tra 1-81.

Pluripotent stem cells suitable for use in the present invention include, for example, the human embryonic stem cell line H9 (NIH code: WA09), the human embryonic stem cell line H1 (NIH code: WA01), the human embryonic stem cell line H7 (NIH code: WA07), and the human embryonic stem cell line SA002 (Cellartis, Sweden). Also suitable for use in the present invention are cells that express at least one of the following markers characteristic of pluripotent cells: ABCG2, cripto, CD9, FOXD3, CONNEXIN43, CONNEXIN45, OCT4, SOX2, NANOG, hTERT, UTF1, ZFP42, SSEA-3, SSEA-4, Tra 1-60, and Tra 1-81.

Markers characteristic of the definitive endoderm lineage are selected from the group consisting of SOX17, GATA4, HNF3 beta, GSC, CERT, Nodal, FGF8, Brachyury, Mix-like homeobox protein, FGF4, CD48, eomesodermin (EOMES), DKK4, FGF17, GATA6, CXCR4, C-Kit, CD99, and OTX2. Suitable for use in the present invention is a cell that expresses at least one of the markers characteristic of the definitive endoderm lineage. In one aspect of the present invention, a cell expressing markers characteristic of the definitive endoderm lineage is a primitive streak precursor cell. In an alternate aspect, a cell expressing markers characteristic of the definitive endoderm lineage is a mesendoderm cell. In an alternate aspect, a cell expressing markers characteristic of the definitive endoderm lineage is a definitive endoderm cell.

Markers characteristic of the pancreatic endoderm lineage are selected from the group consisting of PDX1, NKX6.1, HNF1 beta, PTF1 alpha, HNF6, HNF4 alpha, SOX9, HB9 and PROX1. Suitable for use in the present invention is a cell that expresses at least one of the markers characteristic of the pancreatic endoderm lineage. In one aspect of the present invention, a cell expressing markers characteristic of the pancreatic endoderm lineage is a pancreatic endoderm cell wherein the expression of PDX-1 and NKX6.1 are substantially higher than the expression of CDX2 and SOX2.

Markers characteristic of the pancreatic endocrine lineage are selected from the group consisting of NGN3, NEUROD, ISL1, PDX1, NKX6.1, PAX4, ARX, NKX2.2, and PAX6. In one embodiment, a pancreatic endocrine cell is capable of expressing at least one of the following hormones: insulin, glucagon, somatostatin, and pancreatic polypeptide. Suitable for use in the present invention is a cell that expresses at least one of the markers characteristic of the pancreatic endocrine lineage. In one aspect of the present invention, a cell expressing markers characteristic of the pancreatic endocrine lineage is a pancreatic endocrine cell. The pancreatic endocrine cell may be a pancreatic hormone-expressing cell. Alternatively, the pancreatic endocrine cell may be a pancreatic hormone-secreting cell.

In one aspect of the present invention, the pancreatic endocrine cell is a cell expressing markers characteristic of the β cell lineage. A cell expressing markers characteristic of the β cell lineage expresses PDX1 and at least one of the following transcription factors: NKX2.2, NKX6.1, NEUROD, ISL1, HNF3 beta, MAFA, PAX4, and PAX6. In one aspect of the present invention, a cell expressing markers characteristic of the β cell lineage is a β cell.

This invention describes an in vitro method and a cell population that can generate single hormonal insulin positive cells which are also PDX-1 and NKX6.1 positive. The method used in this invention includes a series of stages that direct, in a stepwise manner, the differentiation of human pluripotent cells to single hormonal cells through the following intermediate stages:
  a) generation of definite endoderm (DE) cells from undifferentiated human embryonic stem cells comprising culturing pluripotent cells in medium comprising glucose, a TGF-B ligand and a WNT activator;
  b) differentiation of DE cells into gut tube cells comprising culturing DE cells in medium comprising glucose, Vitamin C, and a FGF ligand;
  c) differentiation of gut tube cells into posterior foregut endoderm cells expressing PDX-1 and SOX2. This differentiation is accomplished by culturing the gut tube cells in the presence of a shh inhibitor, a BMP inhibitor, a TGF-B ligand, a FGF ligand, retinoic acid, vitamin C and a PKC activator;
  d) differentiating the posterior foregut cells into pancreatic foregut cells expressing PDX-1 and NKX6.1, and expressing lower level of SOX2 as compared to posterior foregut cells. This differentiation is accomplished by culturing the posterior foregut cells in the presence of a shh inhibitor, a BMP inhibitor, low dose of retinoic acid, vitamin C and a PKC activator.
  e) differentiating pancreatic foregut cells into pancreatic endoderm cells expressing PDX-1, a higher level of NKX6.1, and a lower level of SOX2 as compared to pancreatic foregut cells. The differentiation is accomplished by culturing the pancreatic foregut cells in medium supplemented with a shh inhibitor, a TGF-B inhibitor, low dose of retinoic acid, and vitamin C; and
  f) differentiating pancreatic endoderm cells into pancreatic endocrine precursor cells followed by single-hormonal pancreatic endocrine cells. The differentiation is accomplished by culturing the pancreatic endoderm cells in medium supplemented with a shh inhibitor, low dose of retinoic acid, and vitamin C.

In an embodiment, the cells in all stages of stepwise differentiation are cultured in a media formulation containing less than 25 mM glucose. In some embodiments, the glucose concentration is in the range of about 8 mM to about 20 mM glucose.

In some embodiments, media formulations used to generate gut tube stage cells and all subsequent steps contain ascorbic acid (also known as Vitamin C). In an embodiment, the concentration of ascorbic acid is about 0.01 mM to about 1 mM. In an embodiment, the concentration of ascorbic acid is from about 0.1 mM to about 0.5 mM.

The present invention is further illustrated, but not limited, by the following examples.

Example 1

Differentiation of Human Embryonic Stem Cells of the Cell Line H1 to Pancreatic Endocrine Precursor Cells in the Absence of Fetal Bovine Serum-Modulation of BMP/TGF-B Pathways Results in Improved Production of Pancreatic Endoderm Population and Reduced Percentage of SOX2+ Population This example was carried out to show that pancreatic endoderm cultures can be generated having very high expression levels of PDX-1 and NKX6.1 while having low level expression of CDX2 and SOX2.

Cells of the human embryonic stem cell line H1 (hESC H1) were harvested at various passages (passage 40 to passage 52) and were seeded as single cells at a density of 100,000 cells/cm$^2$ on MATRIGEL™ (1:30 dilution; BD Biosciences, NJ, USA) coated dishes in mTeSR®1 media (StemCell Technologies, Vancouver, Canada) supplemented with 10 µM of Y27632 (Rock inhibitor, Catalog# Y0503, SigmaAldrich, MO, USA). Forty-eight hours post seeding, cultures were washed and incubated in incomplete PBS (phosphate buffered saline without Mg or Ca) for approximately 30 seconds. Cultures were differentiated into pancreatic endocrine lineage as follows:

a. Stage 1 (Definitive Endoderm (DE)—3 days): Cells were cultured for one day in stage 1 media: MCDB-131 medium (Catalog#10372-019, Invitrogen, CA, USA) supplemented with 0.1% fatty acid-free BSA (Catalog#68700, Proliant, Iowa, USA), 0.0012 g/ml sodium bicarbonate (Catalog #S3187, SigmaAldrich, MO, USA), 1× GlutaMax™ (Catalog #35050-079, Invitrogen), 5 mM D-Glucose (Catalog# G8769, SigmaAldrich, MO, USA), containing 100 ng/ml GDF8 (R&D Systems, MN, USA) and 1 µM MCX compound (a GSK3B inhibitor, 14-Prop-2-en-1-yl-3,5,7,14,17,23,27-heptaazatetracyclo[19.3.1.1~2,6~.1~8,12~]heptacosa-1(25),2(27),3,5,8(26),9,11,21,23-nonaen-16-one, U.S. patent application Ser. No. 12/494,789; incorporated herein by reference in its entirety). Cells were then cultured for one day in MCDB-131 medium supplemented with 0.1% fatty acid-free BSA, 0.0012 g/ml sodium bicarbonate, 1× GlutaMax™, 5 mM D-Glucose, 100 ng/ml GDF8, and 100 nM MCX compound. Cells were then cultured for one day in MCDB-131 medium to which 0.1% fatty acid-free BSA, 0.0012 g/ml sodium bicarbonate, 1× GlutaMax™, 5 mM D-Glucose, and 100 ng/ml GDF8 had been added.

b. Stage 2 (Primitive gut tube—2 days): Stage 1 cells were treated for two days with MCDB-131 medium supplemented with 0.1% fatty acid-free BSA, 0.0012 g/ml sodium bicarbonate, 1× GlutaMax™, 5 mM D Glucose, and 25 ng/ml FGF7.

c. Stage 3 (Foregut—2 days): Stage 2 cells were cultured for one day in Stage 3 medium: MCDB-131 medium supplemented with 1:200 dilution of ITS-X (Invitrogen), 2.5 mM Glucose, 1× GlutaMax™, 0.0015 g/ml sodium bicarbonate, 2% fatty acid-free BSA, 25 ng/ml FGF7, 10 ng/ml activin-A (R & D systems), 0.25 µM SANT-1 (shh inhibitor, SigmaAldrich), 1 µM Retinoic acid (RA) (SigmaAldrich), and 200 nM TPB (PKC activator; Catalog#565740; EMD, NJ, USA), containing 100 nM LDN-193189 (BMP receptor inhibitor; Catalog #04-0019; Stemgent, Calif., USA). The cells were then cultured for an additional day in the Stage 3 medium supplement with 10 nM LDN-193189.

d. Stage 4 (Pancreatic foregut precursor—2 days): Stage 3 cells were cultured for two days in MCDB-131 medium supplemented with a 1:200 dilution of ITS-X, 2.5 mM Glucose, 1× GlutaMax™, 0.0015 g/ml sodium bicarbonate, 2% fatty acid-free BSA, 0.25 µM SANT-1, 50 nM RA, 200 nM TPB, and 50 nM LDN-193189.

e. Stage 5 (Pancreatic endoderm, 2-7 days): Stage 4 cells were cultured for 2-7 days in MCDB-131 medium supplemented with a 1:200 dilution of ITS-X, 2.5 mM Glucose, 1× GlutaMax™, 0.0015 g/ml sodium bicarbonate, 2% fatty acid-free BSA, 0.25 µM SANT-1, and 50 nM RA.

At specified stages, samples were collected and analyzed by real-time PCR, immune-histochemistry, or fluorescent activated cell sorting (FACS).

For FACS analyses, the hESC-derived cells were released into single-cell suspension by incubation in TrypLE Express (Catalog No. 12604, Invitrogen) at 37° C. for 3-5 minutes. Cells were then washed twice in staining buffer (PBS containing 0.2% fatty acid-free BSA) (Catalog No. 554657, BD Biosciences, NJ, USA). For intracellular antibody staining, cells were first incubated for 20 minutes at 4° C. with Green Fluorescent LIVE/DEAD cell dye (Invitrogen Catalog No. L23101), to allow for live/dead cell discrimination during analysis, followed by a single wash in cold PBS. Cells were fixed in 250 µl of Cytofix/Cytoperm Buffer (BD Biosciences Catalog No. 554722) for 20 minutes at 4° C. followed by two washes in BD Perm/Wash Buffer Solution (BD Biosciences Catalog No. 554723). Cells were re-suspended in 100 µl staining/blocking solution consisting of Perm/Wash buffer supplemented with 2% normal serum (of the appropriate species of the secondary antibody). Cells were then incubated for 30 minutes at 4° C. with primary antibodies at empirically pre-determined dilutions followed by two washes in Perm/Wash buffer. Lastly, cells were incubated with the appropriate secondary antibodies for 30 minutes at 4° C. followed by two washes with Perm/Wash buffer prior to analyses on the BD FACS Canto II.

The following dilutions of primary antibodies were used: rabbit anti-insulin (1:100; Catalog No. C27C9; Cell Signaling, MA, USA), mouse anti-insulin (1:100; Catalog NO. ab6999, Abcam, Mass., USA), mouse anti-glucagon (1:1250; Catalog No. G2654; Sigma-Aldrich), rabbit anti-synaptophysin (1:100; Catalog No. A0010, Dako, Calif., USA), rabbit anti-chromogranin A (1:800; Dako), mouse anti-NKX6.1 (1:50; DSHB, University of Iowa, Iowa, USA), mouse anti-CDX2 (1:250; Invitrogen), goat anti-NeuroD (1:500; R&D Systems), mouse anti-SOX2 (BD, CA, USA), mouse anti-NKX2.2 (DSHB), mouse anti-Pax6 (BD, CA, USA), mouse anti-PDX-1 (BD, CA, USA). Secondary antibodies were used at the following dilutions: goat anti-mouse Alexa 647 (1:500; Invitrogen), goat anti-rabbit PE (1:200; Invitrogen), donkey anti-goat (1:800; Invitrogen). Samples were incubated for 30 minutes at 4° C. after addition of secondary antibodies, followed by a final wash in Perm/Wash buffer. Cells were analyzed on a BD FACS Canto II using the BD FACS Diva Software with at least 30,000 events being acquired.

FIG. 1A to FIG. 1G depict FACS histogram expression profiles of Isotype control (FIG. 1A), chromogranin (FIG.

Figure 1B:
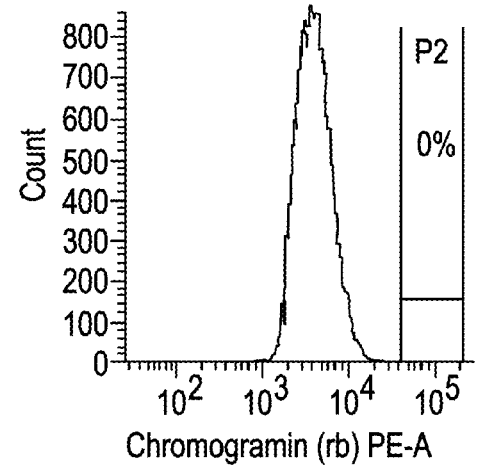
Figure 1C:
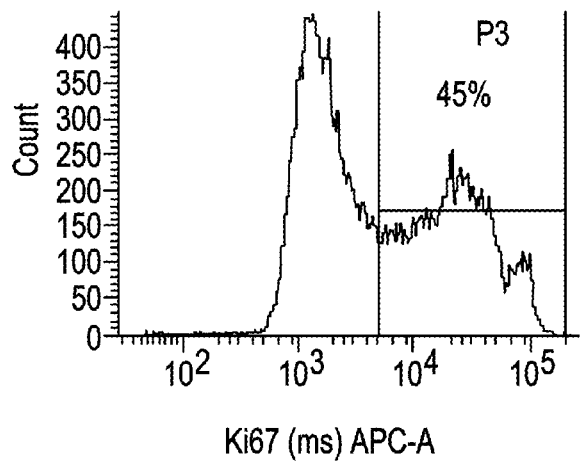
Figure 1D:
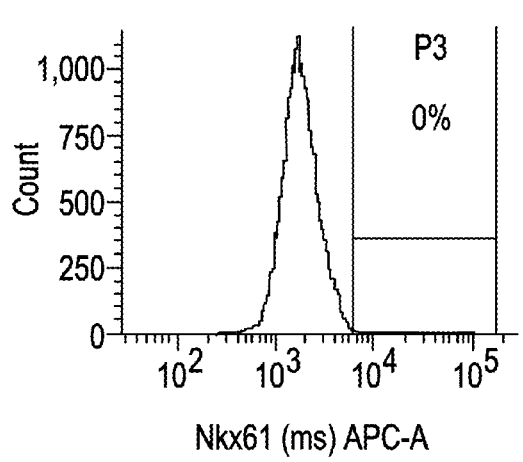
Figure 1E:
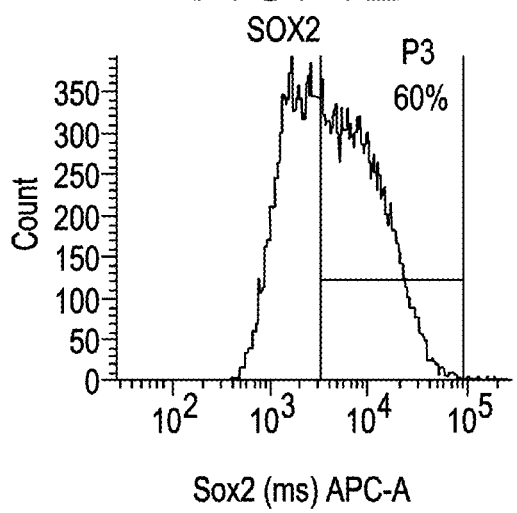
Figure 1F:
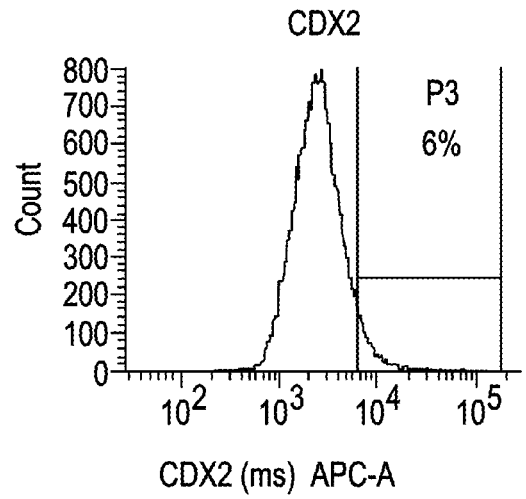
Figure 1G:
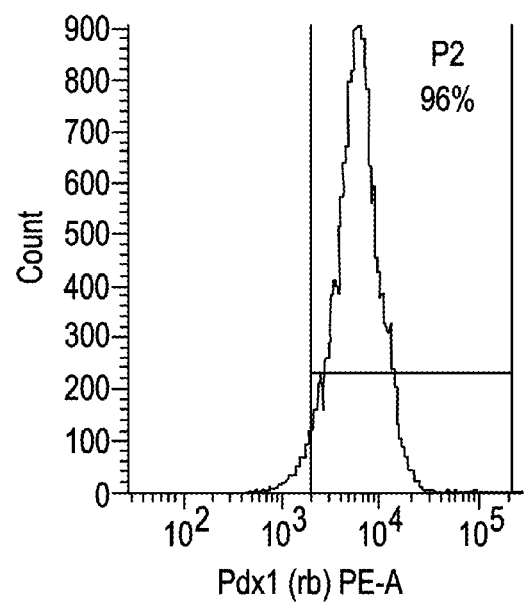

1B), KI-67 (FIG. 1C), NKX6.1 (FIG. 1D), SOX2 (FIG. 1E), CDX2 (FIG. 1F), PDX-1 (FIG. 1G) of cells differentiated according to Example 1 and analyzed at S3 day 2. Percentage expression for each marker is shown on each histogram. At day 2 of stage 3, over 95% of the cells were positive for expression of PDX-1 (FIG. 1G), and about 60% of the cells in the population were positive for expression of SOX2 (FIG. 1E), while less than 10% of the cells were positive for expression of CDX2 (FIG. 1F) or NKX6.1 (FIG. 1D), or chromogranin (FIG. 1B). A significant percentage of cells at stage 3 were in active cell cycle as shown by high percentage of KI-67 positive cells (FIG. 1C).

10%, and NKX6.1 expression significantly increased to >70% and SOX2 expression dramatically decreased to about 2%.

Figure 5A:
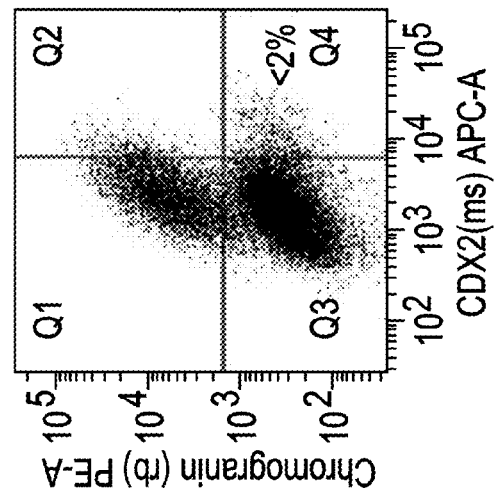
FIG. 5A to FIG. 5C depict FACS histogram expression profiles of the following markers in cells differentiated according to Example 1 and harvested at cells harvested at S5 day 2.
Figure 5B:
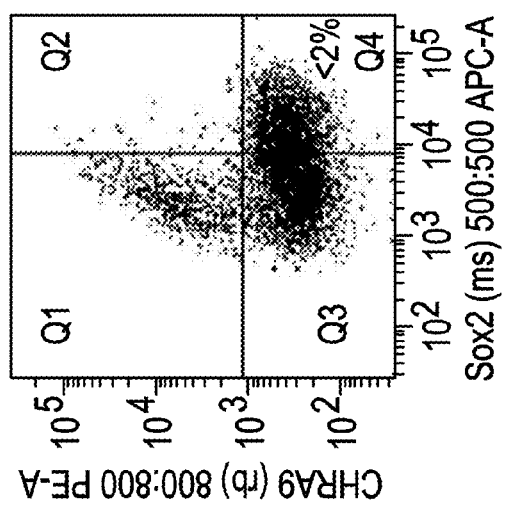
Figure 5C:
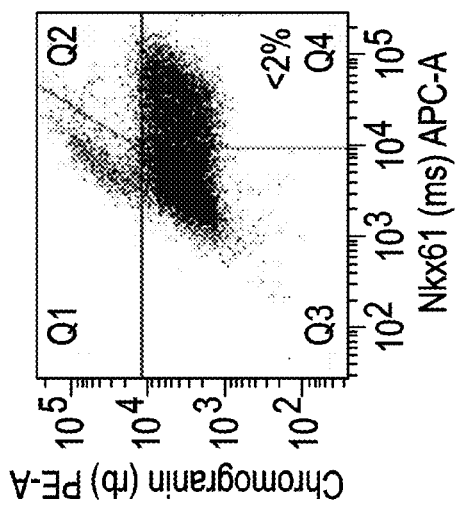

Furthermore, the majority of cells expressing SOX2, CDX2, and NKX6.1 were negative for the expression of chromogranin (see FIG. 5A to FIG. 5C). Thus, S5 cultures prepared following the protocol outlined in this example result in a population of cells where at least 50% of the cells express PDX-1 and NKX6.1 while being negative for CDX-2, SOX2, and chromogranin. Table I summarizes the percentage expression of various endoderm markers at S3-S5.

TABLE I

Average Expression of Endoderm Markers at S3 through S5

|  | Total* | % PDX-1+ | % PDX-1+ and SOX2+ | % PDX-1+ NKX6.1+ and SOX2− | % PDX-1+ CDX2+ | % PDX-1+ NKX6.1+ SOX2+ |
|---|---|---|---|---|---|---|
| Stage 3 2 days | 7 | 96 | 60 | 0 | <5 | 0 |
| Stage 4 2 days | 9 | 97 | 45 | ~40 | <5 | <5 |
| Stage 5 2 days | 11 | 95 | 50 | ~42 | <10 | <25 |
| Stage 5 7 days | 16 | 92 | <2 | ~70 | <5 | <2 |

*Total number of days since start of differentiation.

FIG. 2A to FIG. 2G depict the expression profiles of Isotype control (FIG. 2A), chromogranin (FIG. 2B), KI-67 (FIG. 2C), NKX6.1 (FIG. 2D), SOX2 (FIG. 2E), CDX2 (FIG. 2F), PDX-1 (FIG. 2G), as determined by FACS staining, of cells differentiated according to Example 1, and harvested at day 2 of S4. Percentage expression for each marker is shown on each histogram. Similar to stage 3, over 95% of the cells were positive for PDX-1 expression (FIG. 2G), while about 10% of the cells were positive for CDX2 expression (FIG. 2F), and about 40% of the cells were positive for NKX6.1 expression (FIG. 2D). About 45% of the cells were positive for SOX2 expression (FIG. 2E), a drop from 60% at S3. Chromogranin expression was approximately 3% (FIG. 2B). A significant percentage of cells at stage 4 were in active cell cycle as shown by high percentage of KI-67 positive cells (FIG. 2C).

Figure 3A:
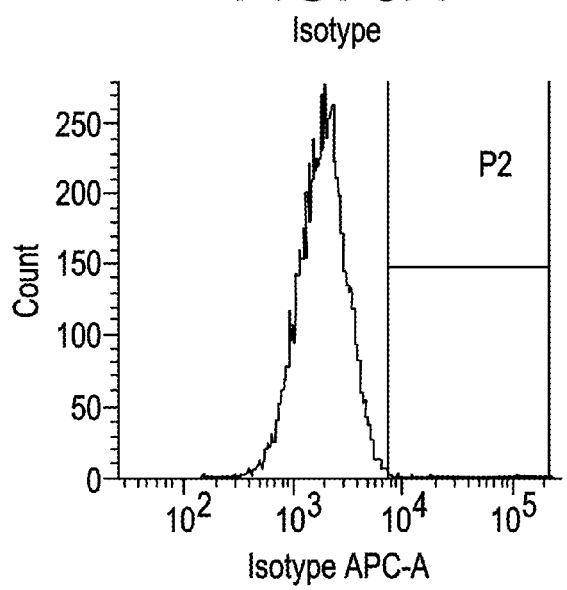
FIG. 3A to FIG. 3G show the FACS histogram expression profiles of the following markers in cells differentiated according to Example 1 and harvested at S5 day 2.
Figure 3B:
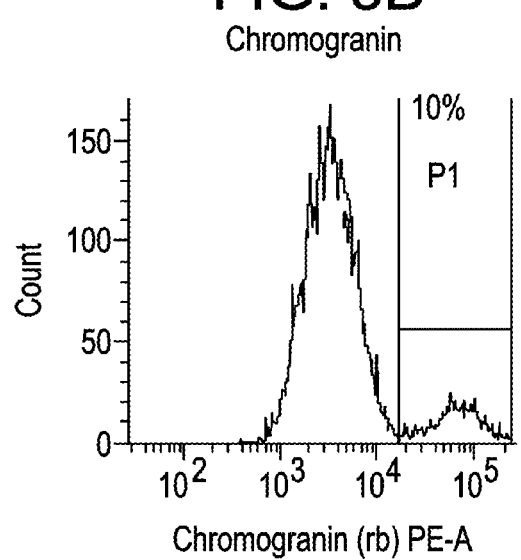
Figure 3C:
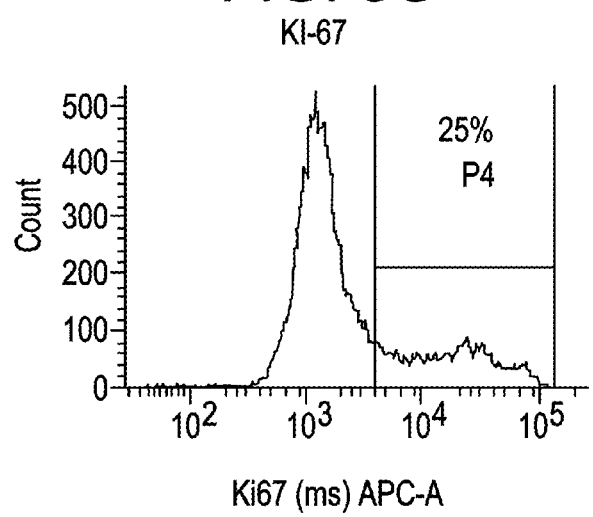
Figure 3D:
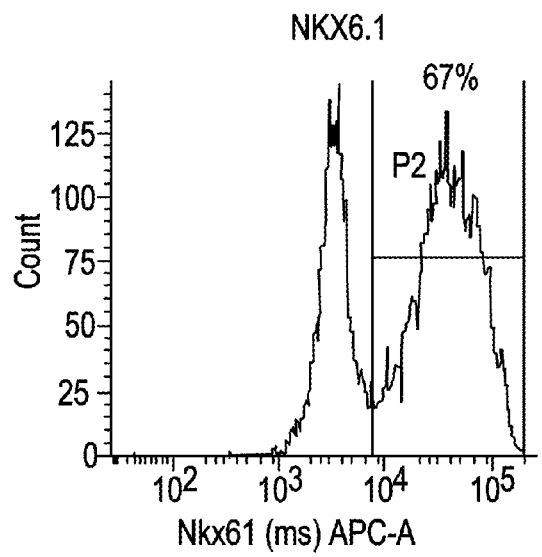
Figure 3E:
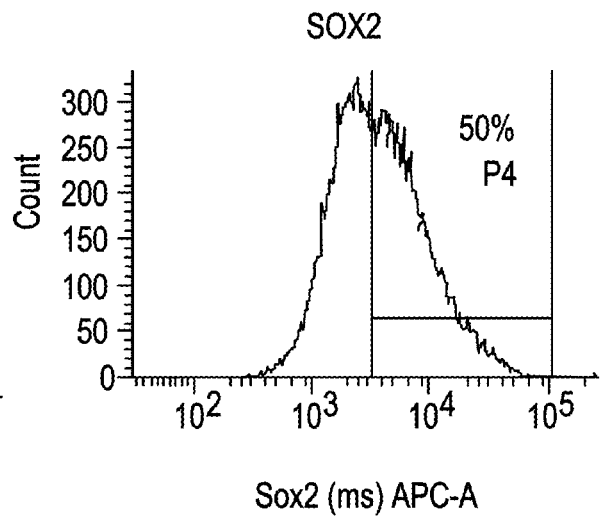
Figure 3F:
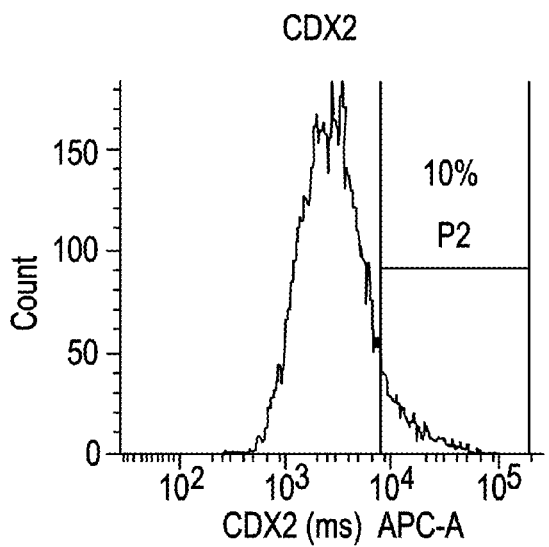
Figure 3G:
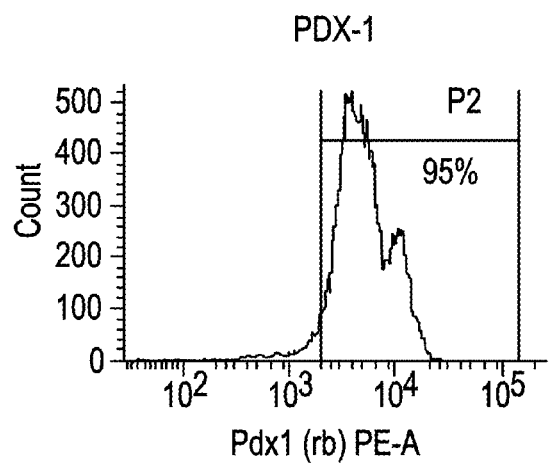

FIG. 3A to 3G depict the relative expression profiles, as determined by FACS analyses, of cells harvested at day 2 of stage 5 following the differentiation protocol outlined in this example. FIG. 3A: isotype control; FIG. 3B: chromogranin; FIG. 3C: KI-67; FIG. 3D: NKX6.1; FIG. 3E: SOX2; FIG. 3F: CDX2; FIG. 3G: PDX-1. Percentage expression for each marker is shown on each histogram. Similar to stages 3 and 4, over 95% of the cells were positive for expression of PDX-1, while approximately 10% of the cells were positive for CDX2 expression, and over 67% of the cells were positive for NKX6.1 expression. SOX2 expression, at approximately 50%, was lower when compared to stage 3, but similar to its expression at S4.

Figure 4F:
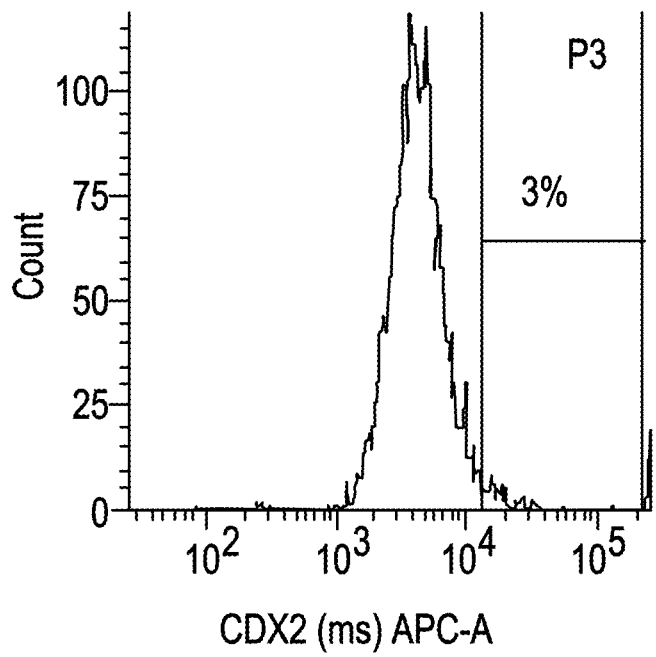
Figure 4G:
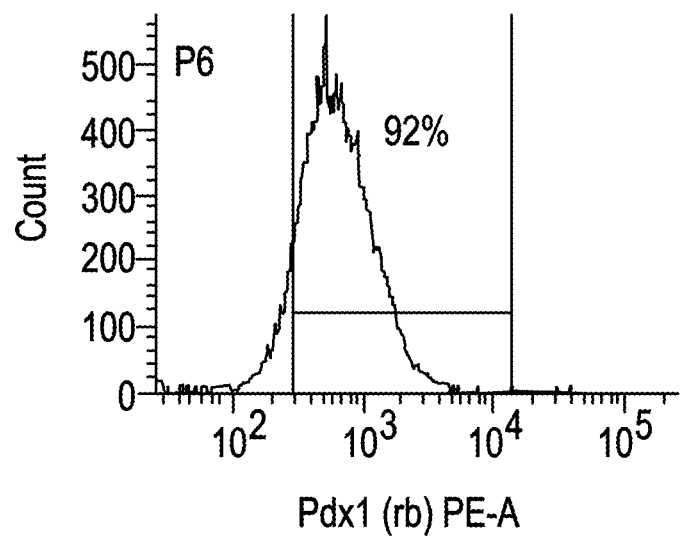
Figure 6A:
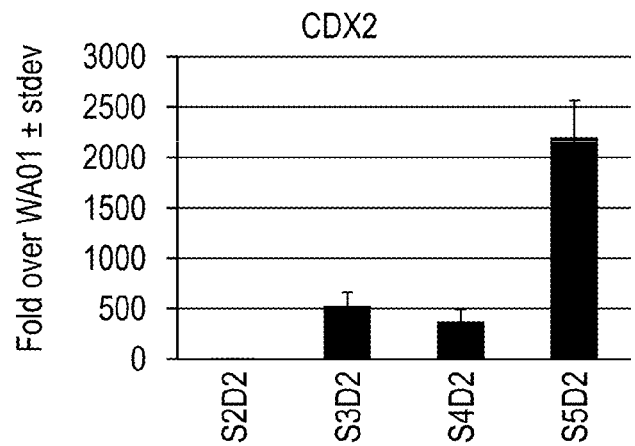
FIG. 6A to FIG. 6T show data from real-time PCR analyses of the expression of the following genes in cells of the human embryonic stem cell line H1 differentiated according to the Example 1 and harvested at S2, S3, S4, and S5.
Figure 6B:
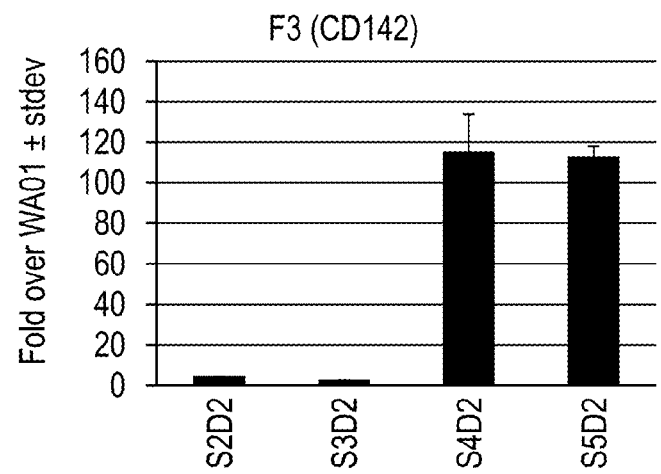
FIG. 6B: CD142.
Figure 6C:
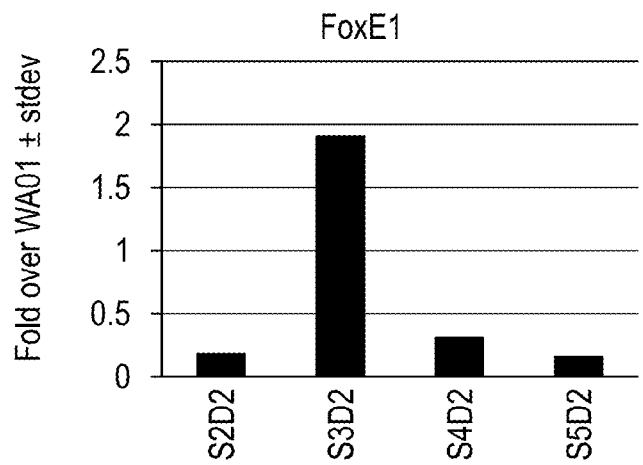
FIG. 6C: FOXE1.
Figure 6D:
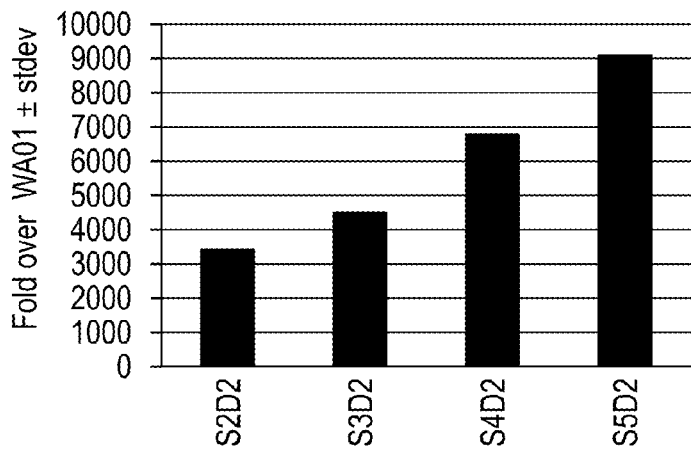
FIG. 6D: HNF4-alpha.
Figure 6E:
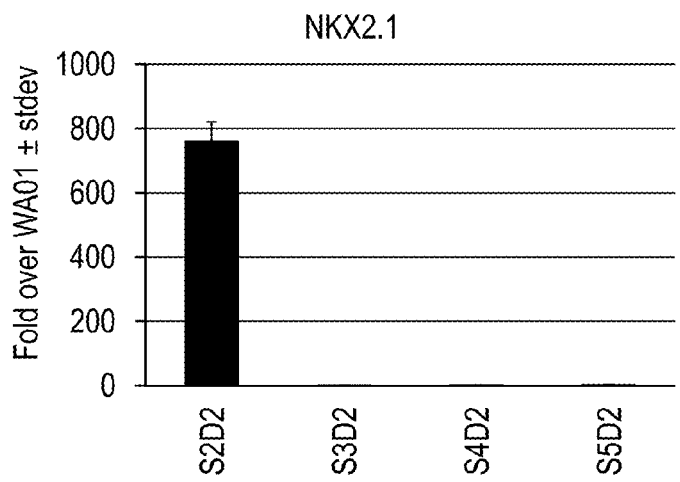
FIG. 6E: NKX2.1.
Figure 6F:
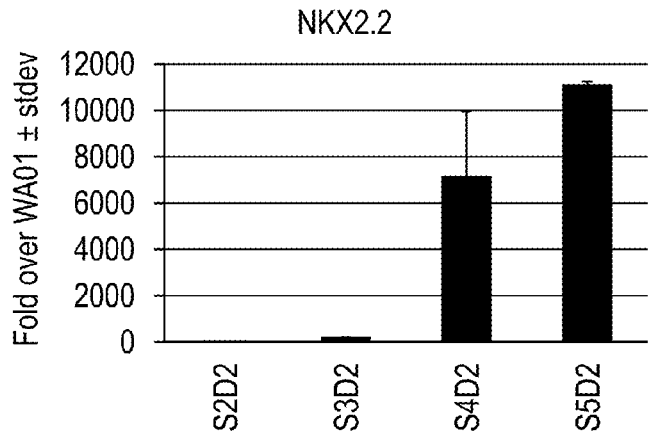
FIG. 6F: NKX2.2.
Figure 6G:
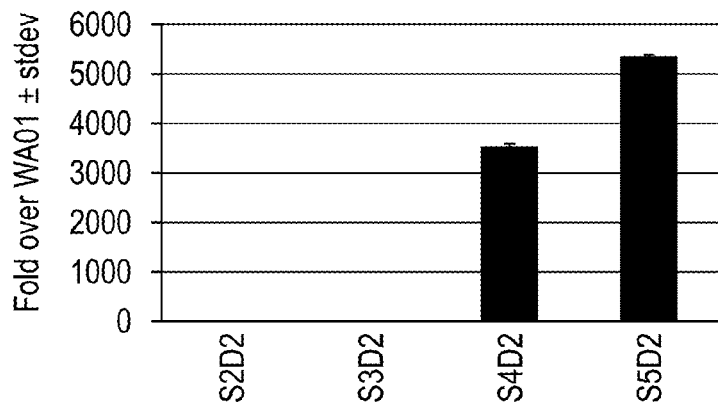
FIG. 6G: NKX6.1.
Figure 6H:
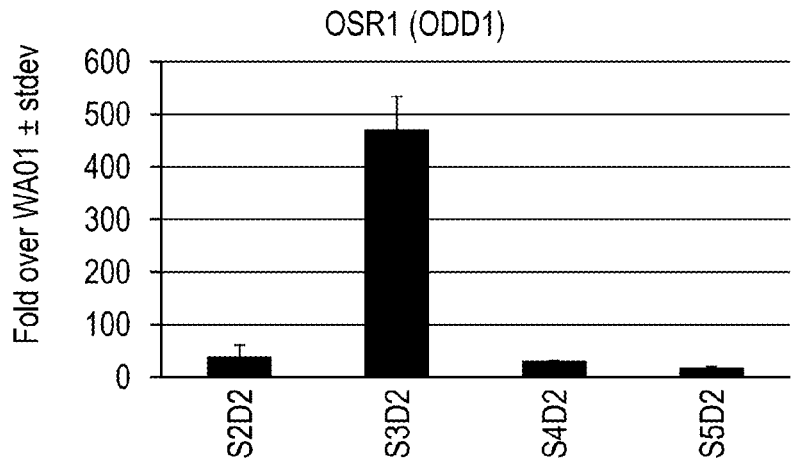
FIG. 6H: OSR1.
Figure 6I:
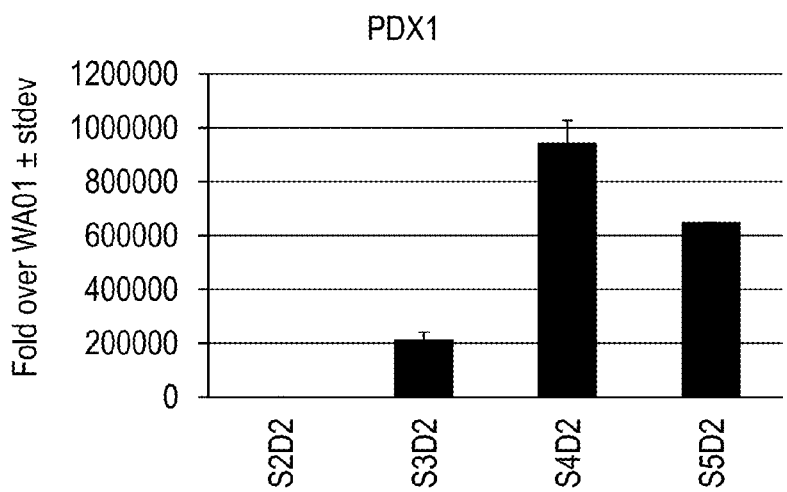
FIG. 6I: PDX-1.
Figure 6J:
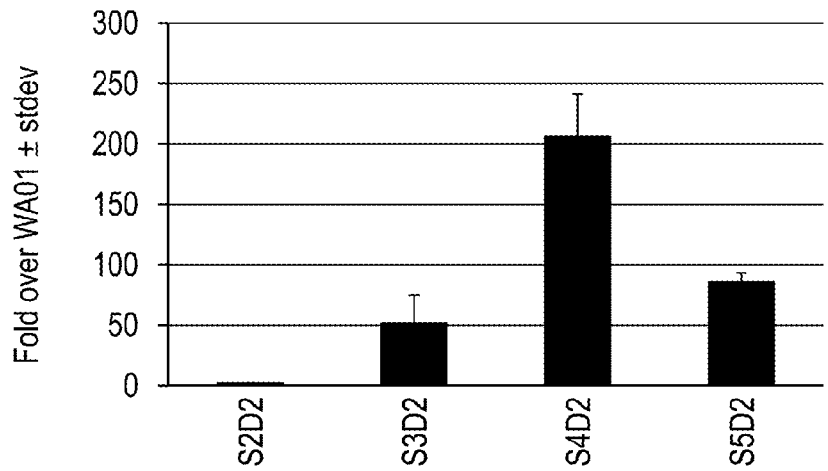
FIG. 6J: PROX1.
Figure 6K:
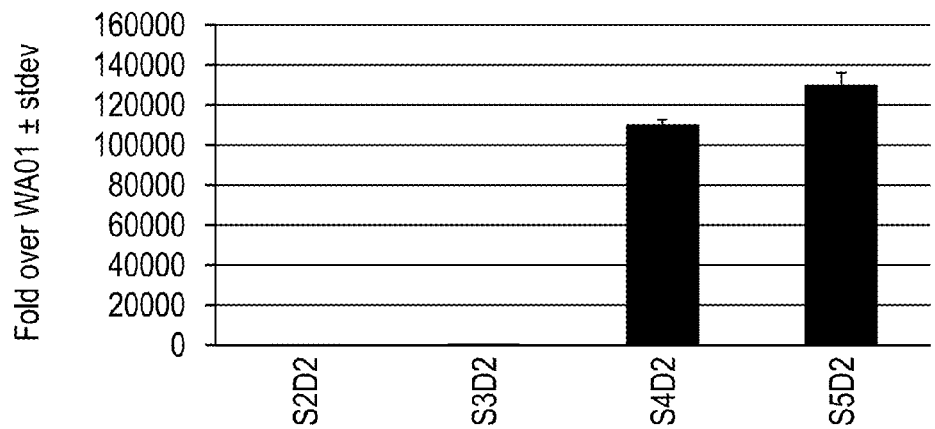
Figure 6L:
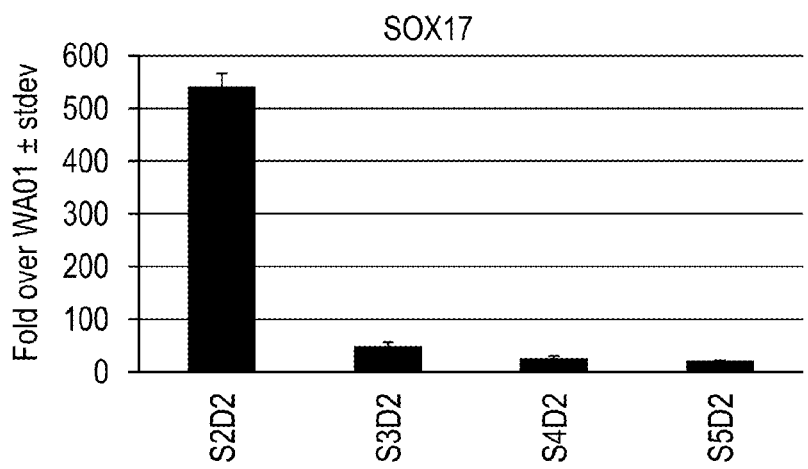
FIG. 6L: SOX17.
Figure 6M:
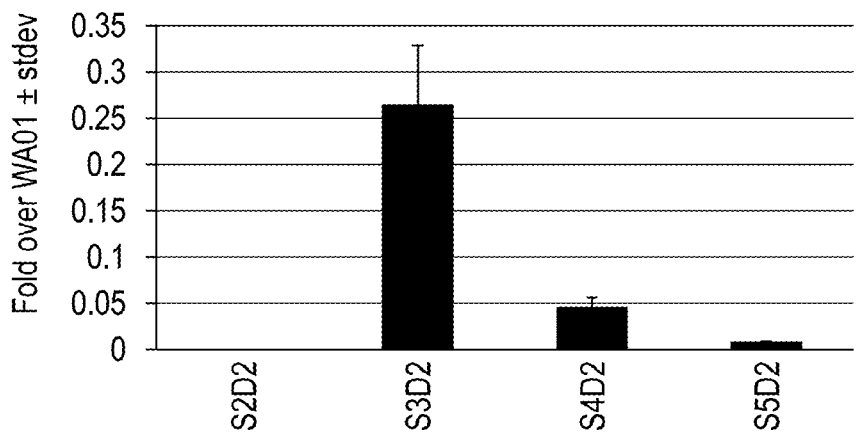
FIG. 6M: SOX2.
Figure 6N:
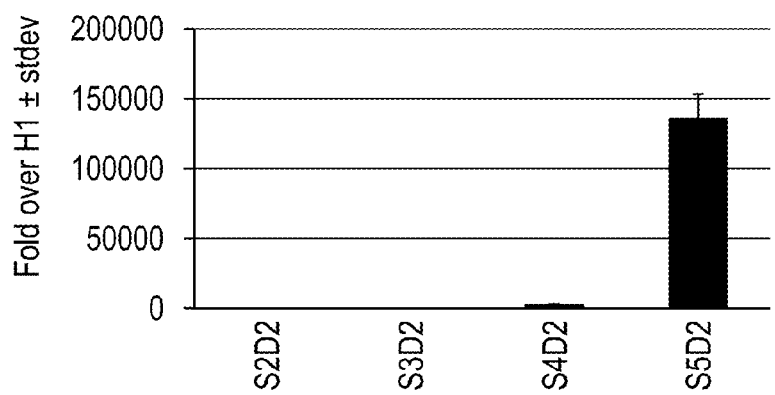
FIG. 6N: insulin.
Figure 6O:
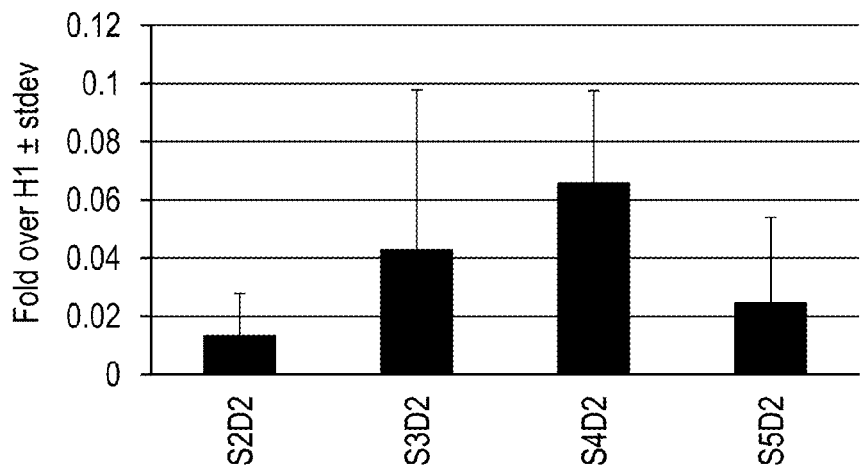
FIG. 6O: ZIC1.
Figure 6P:
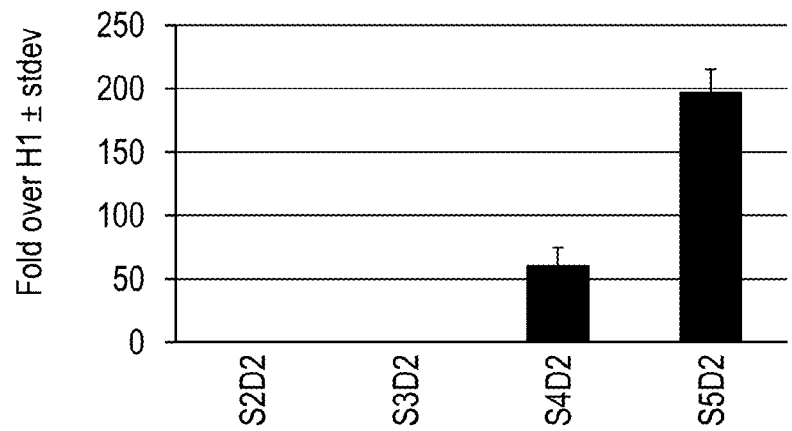
FIG. 6P: chromogranin.
Figure 6Q:
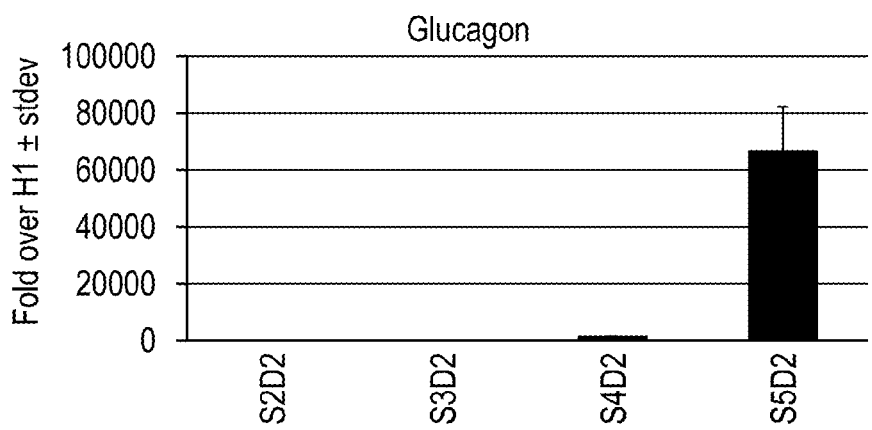
FIG. 6Q: glucagon.
Figure 6R:
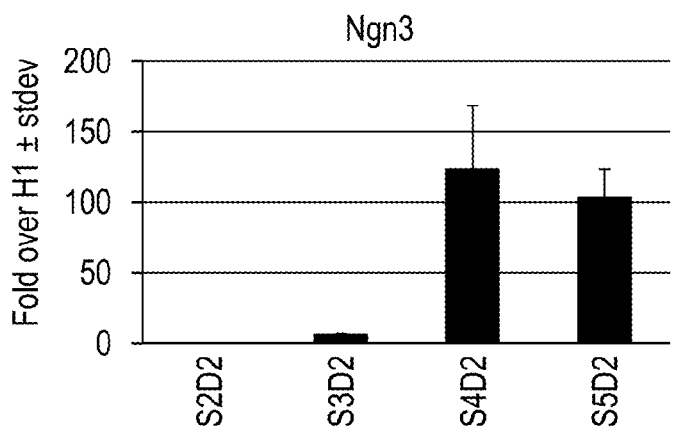
FIG. 6R: Ngn3.
Figure 6S:
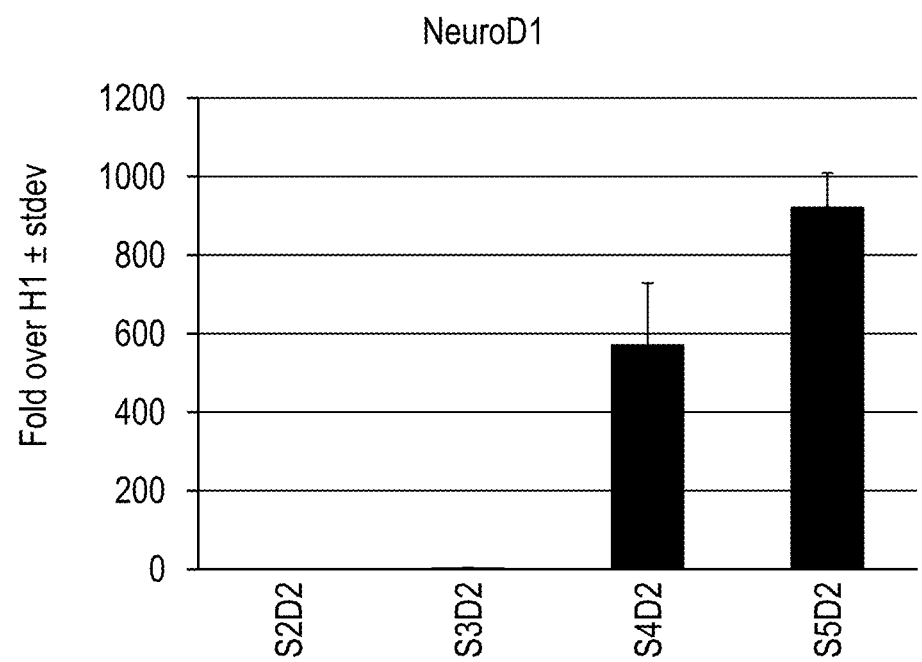
FIG. 6S: NeuroD.
Figure 6T:
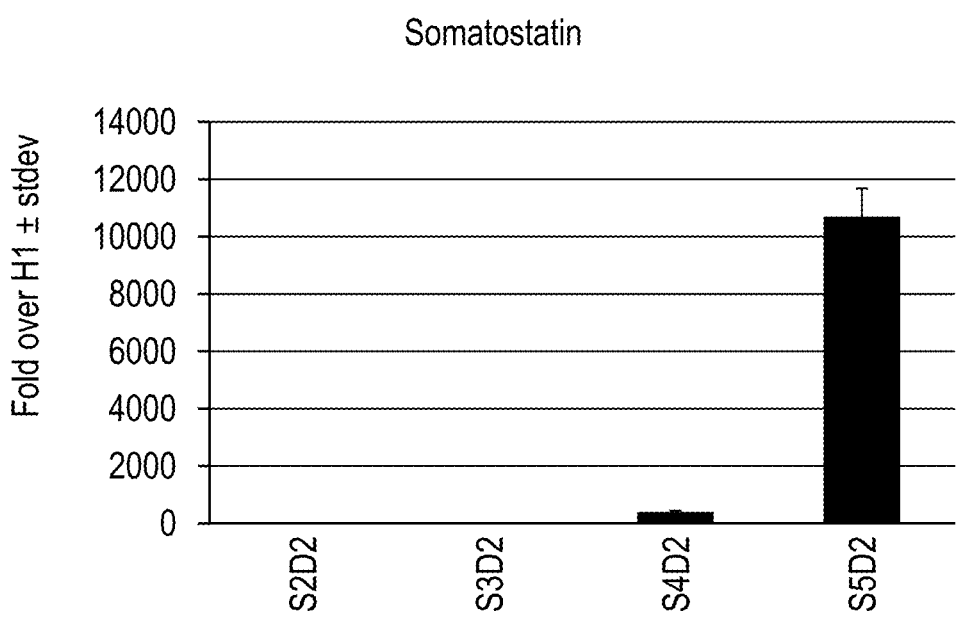

FIG. 4A to FIG. 4G depict the expression of PDX-1 (FIG. 4G), NKX6.1 (FIG. 4D), CDX2 (FIG. 4F), SOX2 (FIG. 4E), Ki-67 (proliferation marker; FIG. 4C) and chromogranin (pan endocrine marker; FIG. 4B) as measured by FACS staining of cells harvested and analyzed at day 7 of stage 5 of differentiation following the protocol outlined in this example. Similar to stages 3 and 4, >90% of the cells were positive for the expression of PDX-1, while CDX2 expression was less than FIG. 6A to FIG. 6T depict mRNA expression profiles measured by real-time PCR of S2, S3, S4, and S5 cells differentiated following the protocol outlined in this example, and reported as fold change over the expression in undifferentiated H1 cells. At stage 3, there was a very low expression of anterior foregut markers such as FOXe1 (FIG. 6C) and NKX2.1 (FIG. 6E). However, at stage 3, SOX2 (FIG. 6M) and OSR1 (FIG. 6H), which mark the stomach region of the gut tube, were significantly upregulated and their expression declined at S4-S5. Pancreatic endoderm markers, such as PTF1a (FIG. 6K), NKX6.1 (FIG. 6G), and PDX-1 (FIG. 6I) reached maximal expression levels at S5 day 2 of culture. The PCR data indicate that at stage 3, the cells transition through a PDX-1+SOX2+ population before becoming PDX-1+ NKX6.1+SOX2−CDX2− at S4-S5. (See FIG. 6I, FIG. 6G, FIG. 6M, and FIG. 6A.) Expression of endocrine markers (chromogranin, insulin, glucagon, and somatostain) reached a maximal expression level at end of S5. Expression of pancreatic endocrine precursor markers, NKX2.2, NeuroD, and NGN3 reached a maximal expression level at S4-S5. Expression of other lineage markers, such as ZIC1 and SOX17 remained low at S4-S5.

In conclusion, cells at stage 5 day 2 which were differentiated following the protocol outlined in this example express low levels of CDX2 and SOX2 while maintaining a high expression level of NKX6.1 and PDX-1. It is believed that the unique combination of timely BMP inhibition, use of low dose RA at S4-S5, use of high glucose at S1-S2 results in the population of cells described in Example 1.

Example 2

Effect of BMP Inhibition and PKC Activation on the Expression of SOX2 at S3-S4

The protocol outlined in this example was performed to shed light on the effects of BMP inhibition, addition of FGF7 along with PKC activation on SOX2 expression at S3-S4.

Cells of the human embryonic stem cell line H1 were harvested at various passages (passage 40 to passage 52) and were seeded as single cells at a density of 100,000 cells/cm$^2$ on MATRIGEL™ (1:30 dilution) coated dishes in mTesr™1 media supplemented with 10 µM of Y27632. Forty eight hours post-seeding, cultures were differentiated into cells of the pancreatic endocrine lineage as follows:

a. Stage 1 (Definitive Endoderm (DE)—3 days): Prior to start of DE, the cultures were washed and incubated with incomplete PBS (no Mg or Ca) for 30 seconds followed by addition of the stage 1 media. Human embryonic stem cells cultured as single cells on MATRIGEL™-coated dishes were treated with MCDB-131 medium supplemented with 0.1% fatty acid-free BSA, 0.0012 g/ml sodium bicarbonate, 1× GlutaMax™, and 2.5 mM D-Glucose, 100 ng/ml GDF8, and 1.5 µM MCX compound (GSK3B inhibitor) for one day. Cells were then treated with MCDB-131 medium supplemented with 0.1% fatty acid-free BSA, 0.0012 g/ml sodium bicarbonate, 1× GlutaMax™, 2.5 mM glucose, and 100 ng/ml GDF8 for days 2-3.

b. Stage 2 (Primitive gut tube—3 days): Stage 1 cells were treated with MCDB-131 medium supplemented with 0.1% fatty acid-free BSA, 0.0012 g/ml sodium bicarbonate, 1× GlutaMax™, 2.5 mM D-Glucose, and 50 ng/ml FGF7 and for three days.

c. Stage 3 (Foregut—3 days): Stage 2 cells were treated with MCDB131 medium supplemented with a 1:200 dilution of ITS-X, 2.5 mM Glucose, 1× GlutaMax™, 0.0015 g/ml sodium bicarbonate, 2% fatty acid-free BSA, 0.25 µM SANT-1, 20 ng/ml of activin-A, 2 µM RA, in the presence or absence of 50 ng/ml FGF7, 50 nM or 200 nM LDN-193189, and/or 200 nM TPB. Cells were incubated for three days in medium using the combinations listed in Table II, below:

TABLE II

Figure 7A:
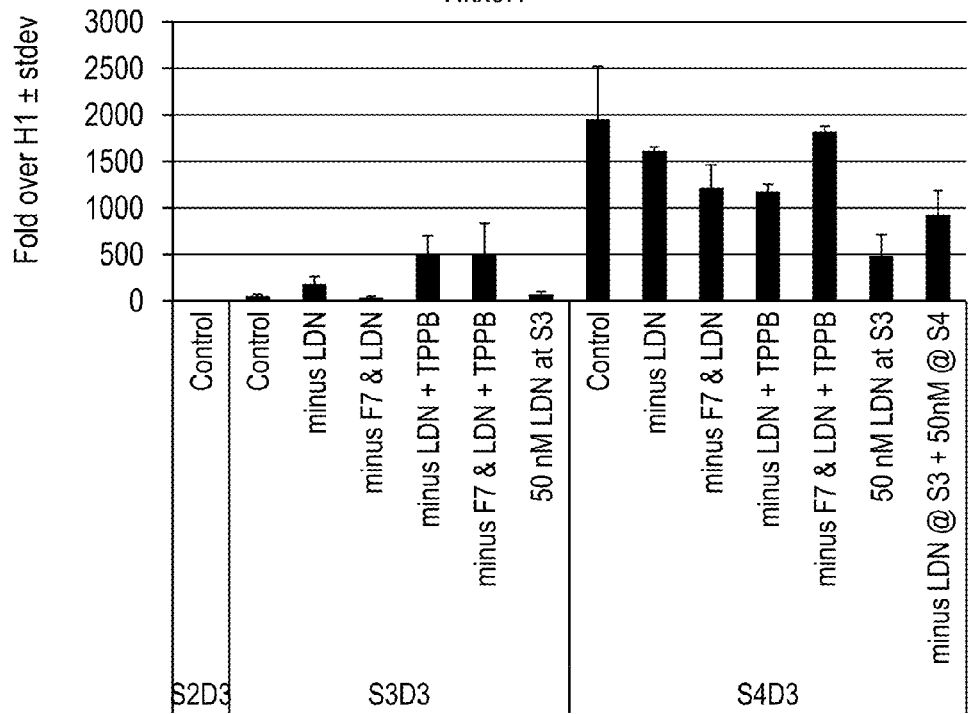
FIG. 7A to FIG. 7G depict data from real-time PCR analyses of the expression of the following genes in cells of the H1 cell line differentiated according to Example 2 and harvested at day 3 of S2, S3, or S4.
Figure 7B:
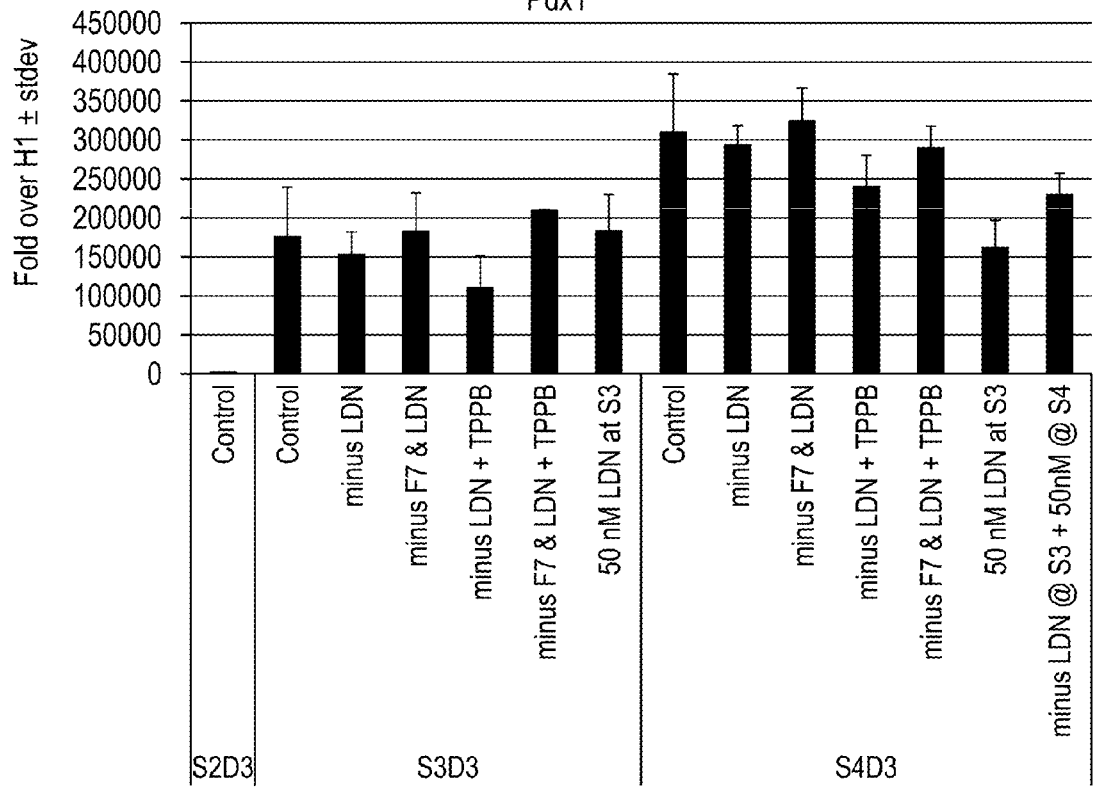
Figure 7C:
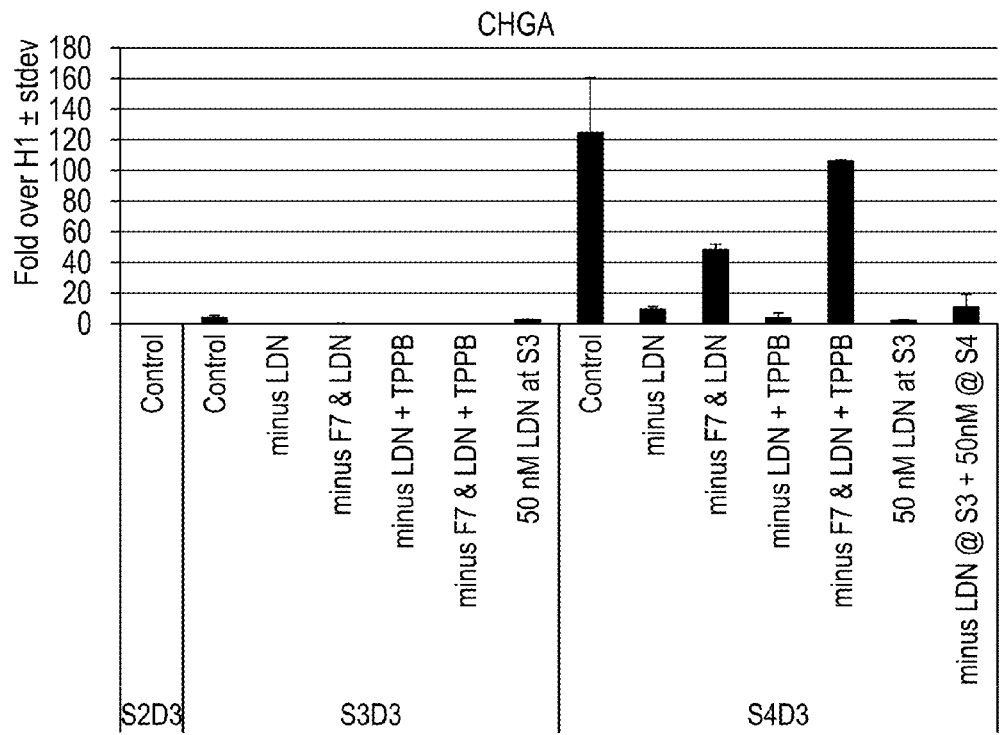
Figure 7D:
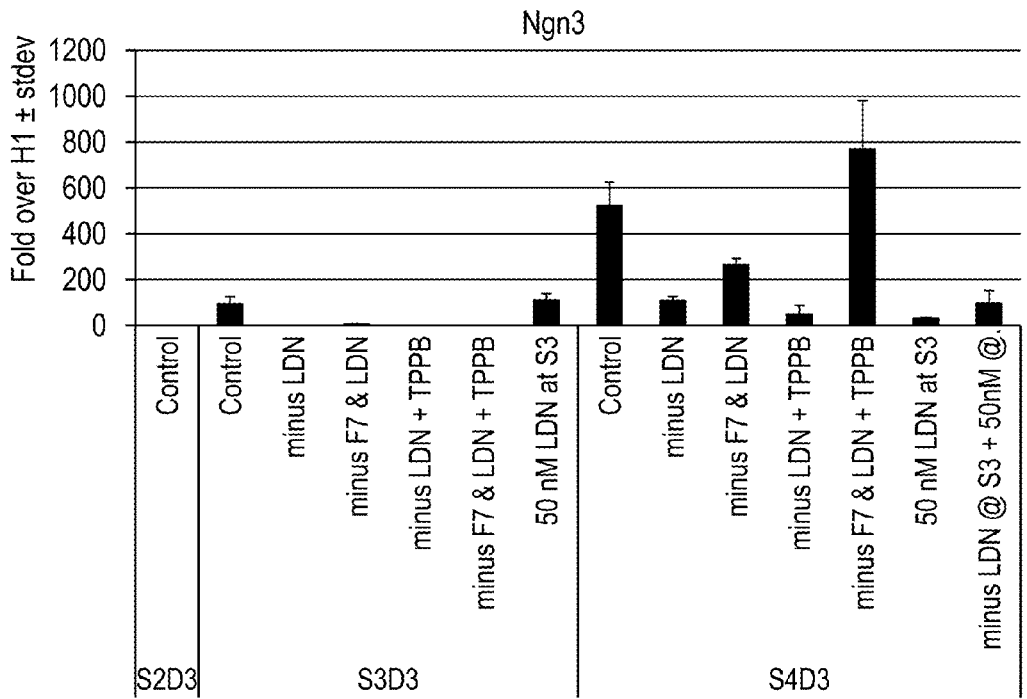
Figure 7E:
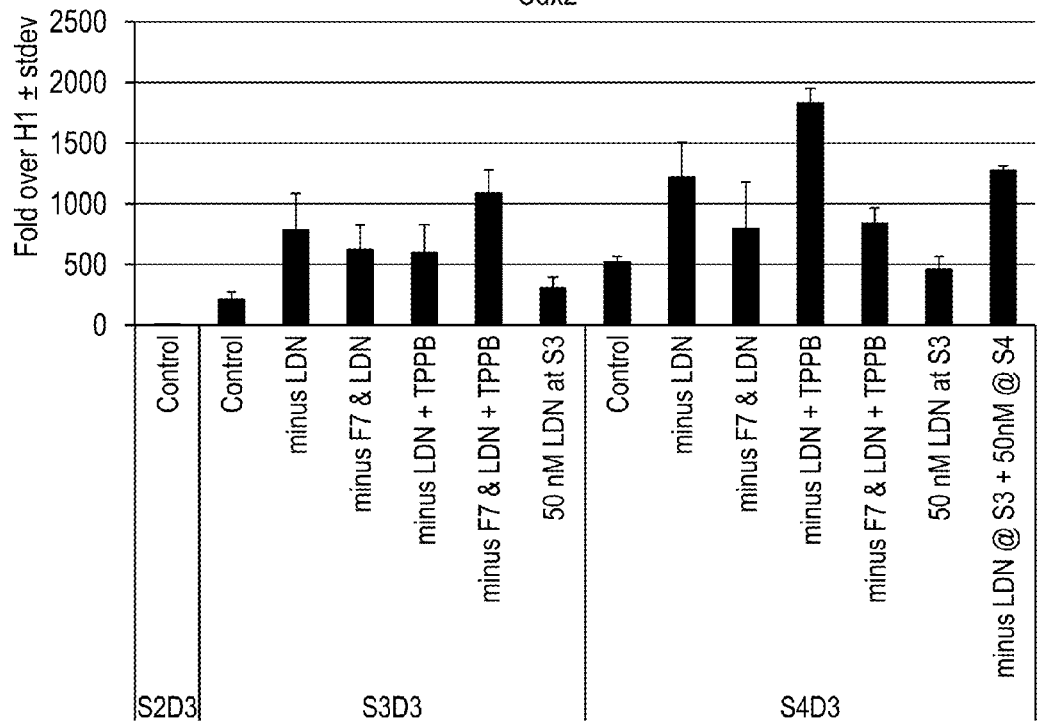

| Stage 3 Treatments | | | | | | |
|---|---|---|---|---|---|---|
| Treatment | AA | FGF7 | LDN-193189 | SANT | RA | TPB |
| 1 | + | + | 200 nM+ | + | + | − |
| 2 | + | + | − | + | + | − |
| 3 | + | − | − | + | + | − |
| 4 | + | + | − | + | + | + |
| 5 | + | − | − | + | + | + |
| 6 | + | + | 50 nM | + | + | − | d. Stage 4 (Pancreatic foregut precursor—3 days): Stage 3 cells were treated with MCDB131 medium supplemented with 1:200 dilution of ITS-X, 2.5 mM Glucose, 1× GlutaMax™, 0.0015 g/ml sodium bicarbonate, 2% fatty acid-free BSA, 0.25 µM SANT-1, 200 nM TPB, 400 nM LDN-193189, 2 µM ALk5 inhibitor (SD-208, disclosed in Molecular Pharmacology 2007, 72:152-161), and 100 nM CYP26A inhibitor (N-{4-[2-Ethyl-1-(1H-1,2,4-triazol-1-yl)butyl]phenyl}-1,3-benzothiazol-2-amine, Janssen, Belgium) for three days.

mRNA was collected at S2-S4 for all the conditions listed above and analyzed using real-time PCR. Control conditions, at S3, refer to cultures where FGF7, AA, SANT, RA, and 200 nM LDN-193189 were used at the concentrations listed at step c, above. As evident by PCR data shown in FIGS. 7A to 7G, removal of LDN-193189 at S3 resulted in a significant decrease in endocrine markers, such as NGN3 (FIG. 7D), and pan-endocrine marker such as chromogranin (see FIG. 7C). Addition of the PKC activator and removal of LDN-193189 at S3 further decreased endocrine markers while enhancing expression of NKX6.1 (see FIG. 7A to FIG. 7G). Furthermore, addition of 50 nM LDN-193189 was as effective as 200 nM LDN-193189 in induction of endocrine markers (chromogranin and NGN3). Removal of LDN-193189 and addition of TPB at S3 enhanced expression of CDX2 (FIG. 7E) and albumin (FIG. 7F) while suppressing SOX2 (FIG. 7G) expression. Moreover, removal of both FGF7 and LDN-193189 significantly enhanced expression of SOX2 (FIG. 7G) and reduced expression of Albumin (FIG. 7F) as compared to cultures were LDN-193189 was removed and FGF7 was retained. These data demonstrate that precise modulation of the BMP inhibition, FGF activation, and PKC activation can result in an endoderm domain that is rich in PDX-1 and NKX6.1 while being low for CDX2, SOX2, and albumin. Lastly, sustained inhibition of BMP at S3-S4 enhanced expression of proendocrine genes plus upregulation of SOX2 expression. This highlights that BMP inhibition needs to be precisely tuned to increase pancreatic endocrine genes while not upregulating SOX2 expression which is absent or low in pancreas development but present in anterior foregut endoderm organs, such as stomach.

Example 3

Early Inhibition of BMP at Foregut Stage is Required for Subsequent Induction of Endocrine Markers This example shows that early inhibition of BMP signaling at S3 is required for subsequent induction of endocrine markers. However, sustained inhibition of BMP at stage 3 also results in strong expression of SOX2. In order to obtain both a high expression of endocrine markers along with low expression of SOX2 expression, a gradient of BMP inhibition was required to induce pro-pancreatic endocrine markers while having a low expression of SXO2 and CDX2.

Cells of the human embryonic stem cell line H1 at various passages (passage 40 to passage 52) were seeded as single cells at a density of 100,000 cells/cm$^2$ on MATRIGEL™ (1:30 dilution) coated dishes in mTesr™1 media supplemented with 10 µM of Y27632. Forty eight hours post seeding, cultures were differentiated into cells of the pancreatic endocrine lineage as follows:

a. Stage 1 (Definitive Endoderm (DE)—4 days): Prior to start of DE, the cells were washed and incubated with incomplete PBS (no Mg or Ca) for 30 seconds followed by incubation in S1 media. Human embryonic stem cells cultured as single cells on MATRIGEL™-coated dishes were treated for one day with MCDB-131 medium supplemented with 0.1% fatty acid-free BSA, 0.0012 g/ml sodium bicarbonate, 1× GlutaMax™, 2.5 mM D-Glucose, 100 ng/ml GDF8, 1.5 µM MCX compound (GSK3B inhibitor). Cells were then treated for two days (days 2-4) with MCDB-131 medium supplemented with 0.1% fatty acid-free BSA, 0.0012 g/ml sodium bicarbonate, 1× GlutaMax™, 2.5 mM glucose, and 100 ng/ml GDF8.

b. Stage 2 (Primitive gut tube—3 days): Stage 1 cells were treated for three days with MCDB-131 medium supplemented with 0.1% fatty acid-free BSA, 0.0012 g/ml sodium bicarbonate, 1× GlutaMax™, 2.5 mM D-Glucose, and 50 ng/ml FGF7.

c. Stage 3 (Foregut—3 days): Stage 2 cells were treated with MCDB-131 medium supplemented with a 1:200 dilution of ITS-X, 2.5 mM Glucose, 1× GlutaMax™, 0.0015 g/ml sodium bicarbonate, 2% fatty acid-free BSA, 0.25 µM SANT-1, 20 ng/ml of Activin-A, 2 µM RA, 50 ng/ml FGF7, 100 nM LDN-193189 (on day 1 only or for the duration of stage 3), and 200 nM TPB. In some cultures, LDN-193189 was removed from stage 3.

d. Stage 4 (Pancreatic foregut precursor—3 days): Stage 3 cells were treated with MCDB-131 medium supplemented with a 1:200 dilution of ITS-X, 2.5 mM Glucose, 1× GlutaMax™, 0.0015 g/ml sodium bicarbonate, 2% fatty acid-free BSA, 0.25 µM SANT-1, 100 nM TPB, 200 nM LDN-193189, 2 µM ALk5 inhibitor, and 100 nM CYP26A inhibitor for three days.

e. Stage 5 (Pancreatic endoderm/endocrine—4 days): Stage 4 cells were treated with MCDB-131 medium supplemented with a 1:200 dilution of ITS-X, 2.5 mM Glucose, 1× GlutaMax™, 0.0015 g/ml sodium bicarbonate, 2% fatty acid-free BSA, 200 nM LDN-193189, and 2 µM ALk5 for four days.

Figure 7F:
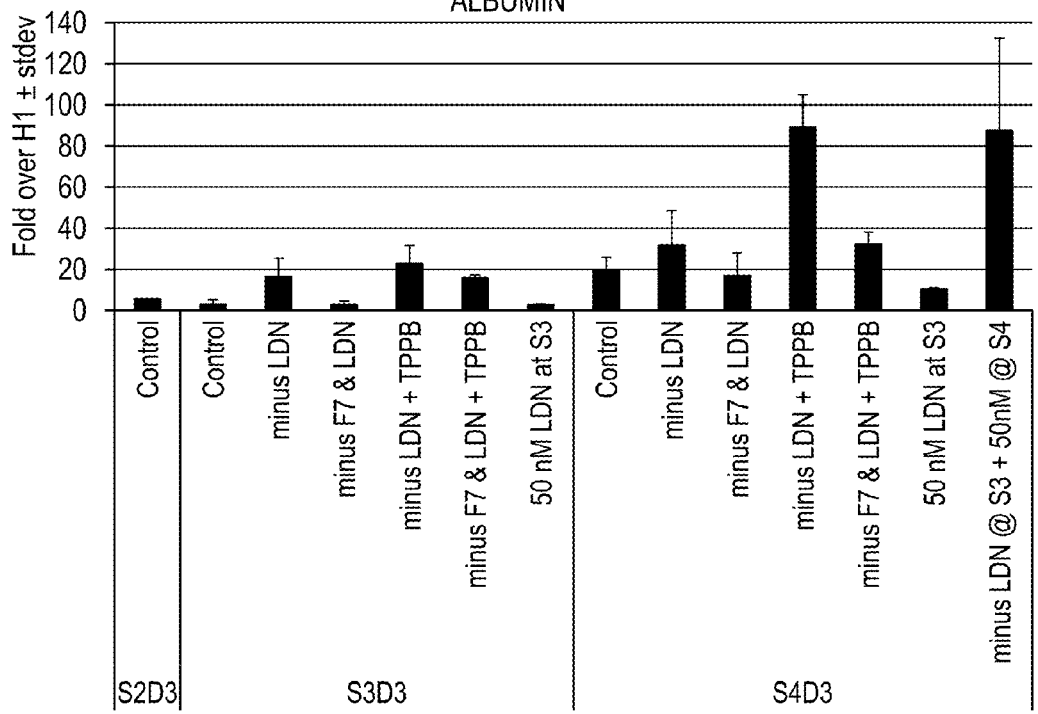
Figure 7G:
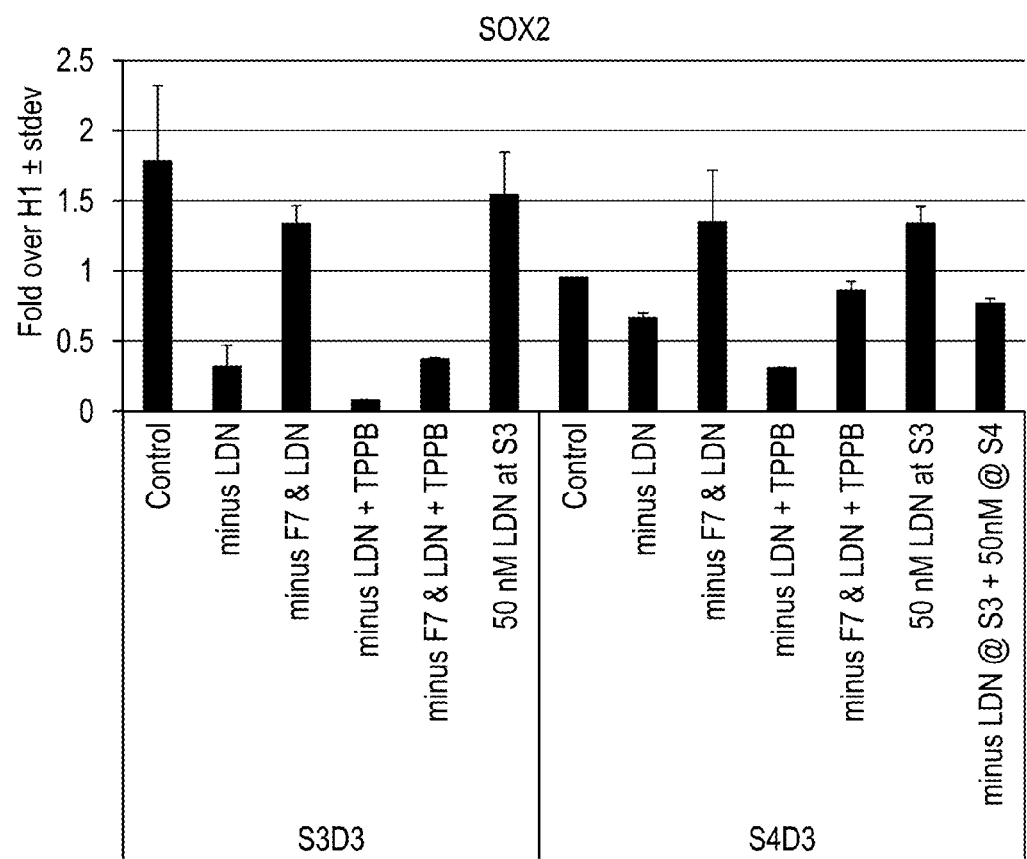
Figure 8A:
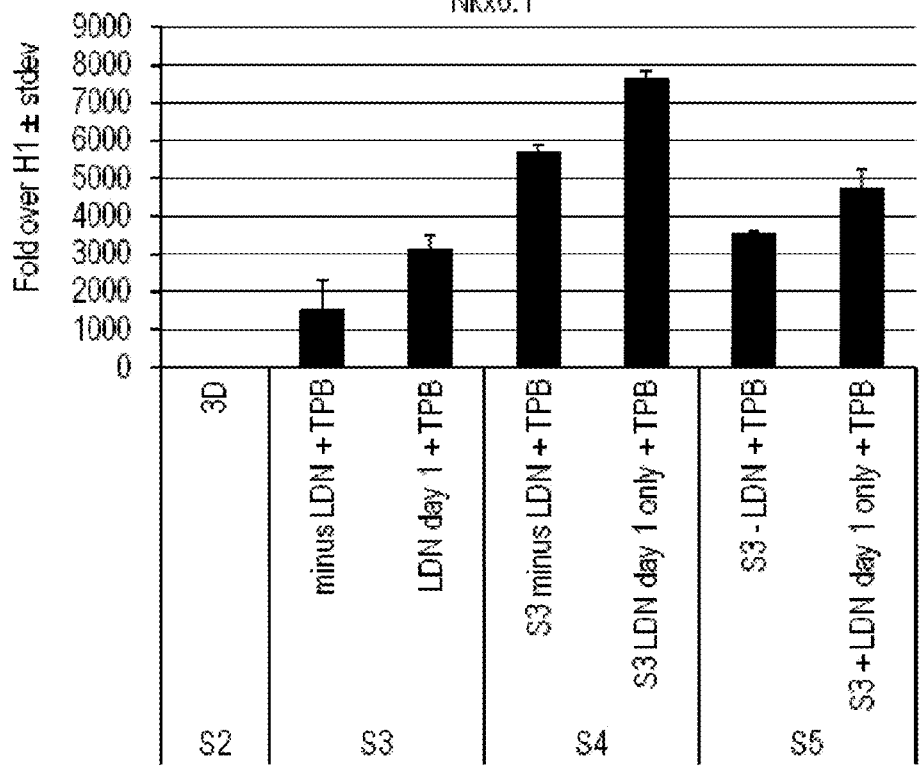
Figure 8B:
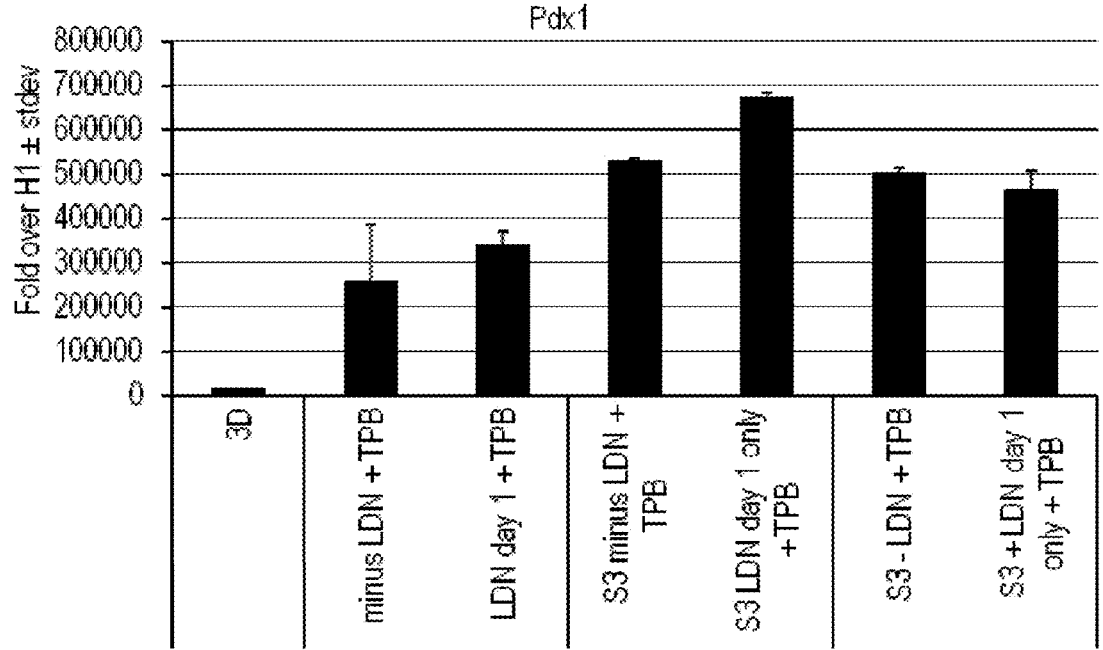
Figure 8C:
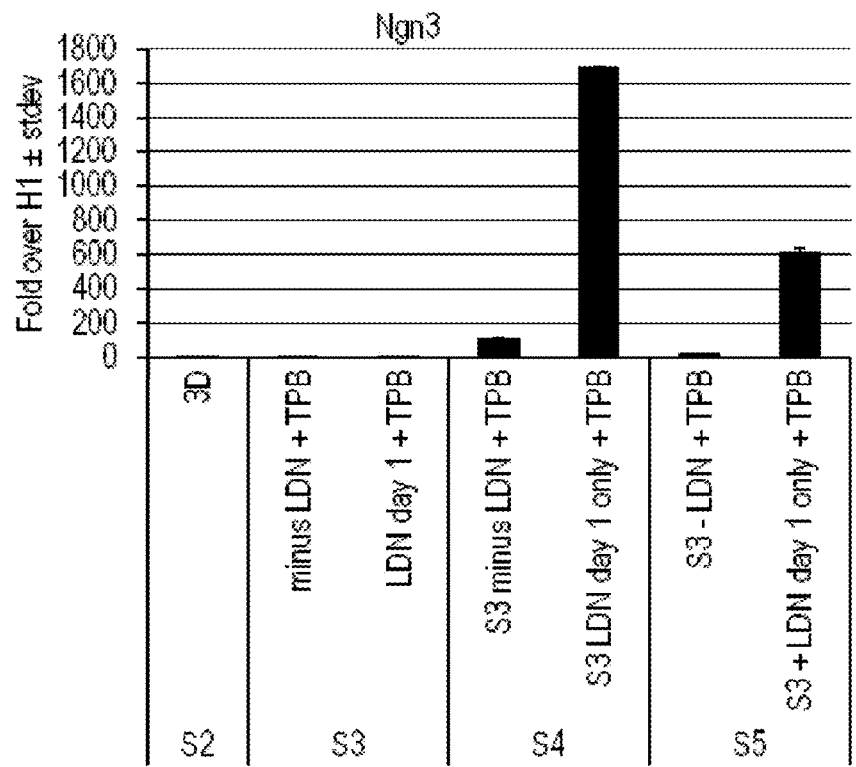
Figure 8D:
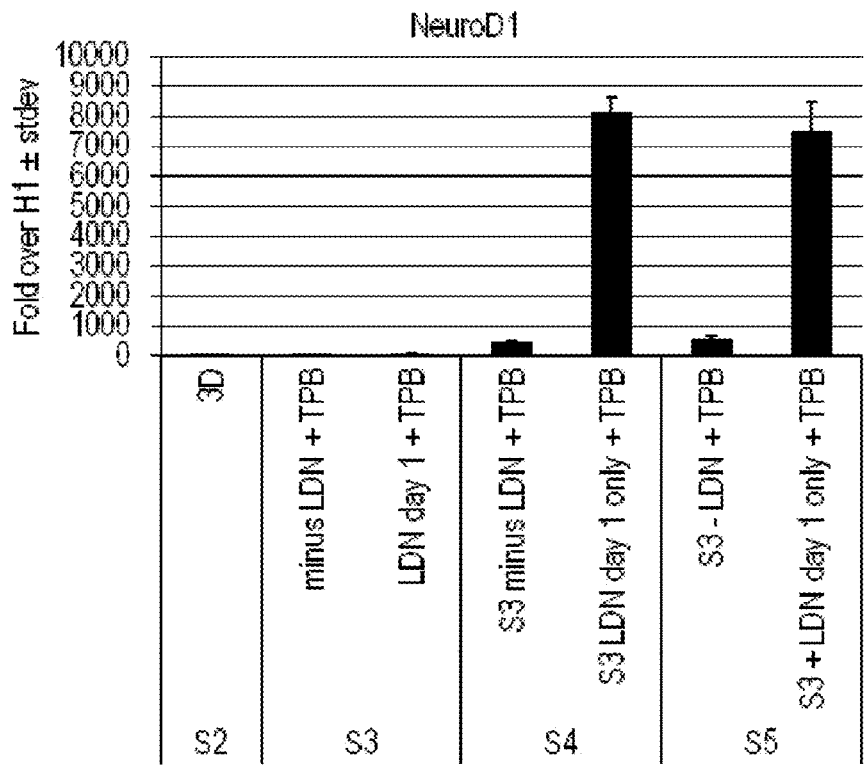
Figure 8E:
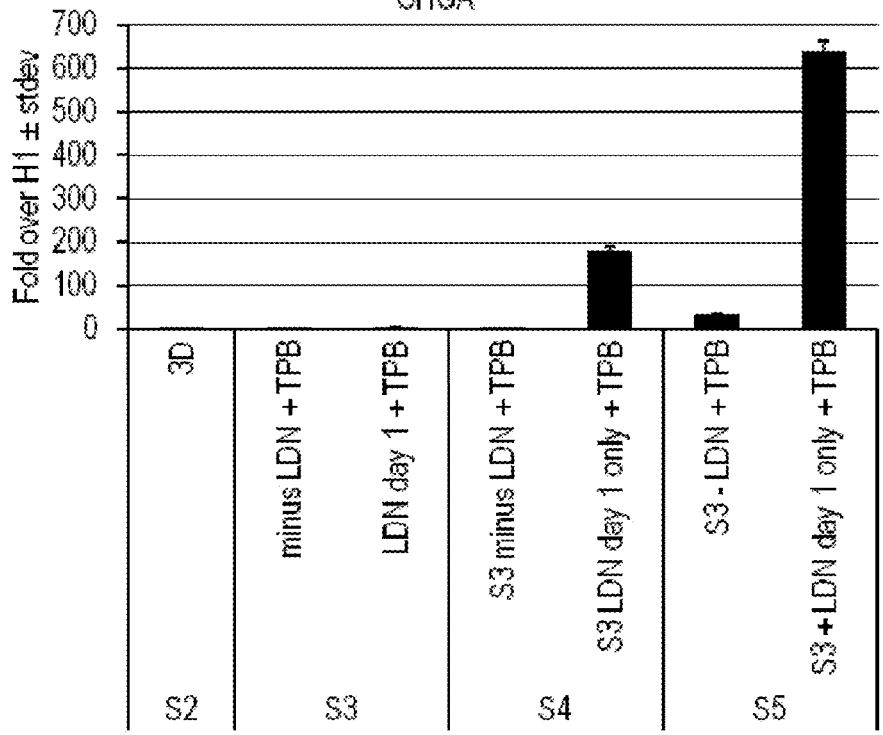
Figure 8F:
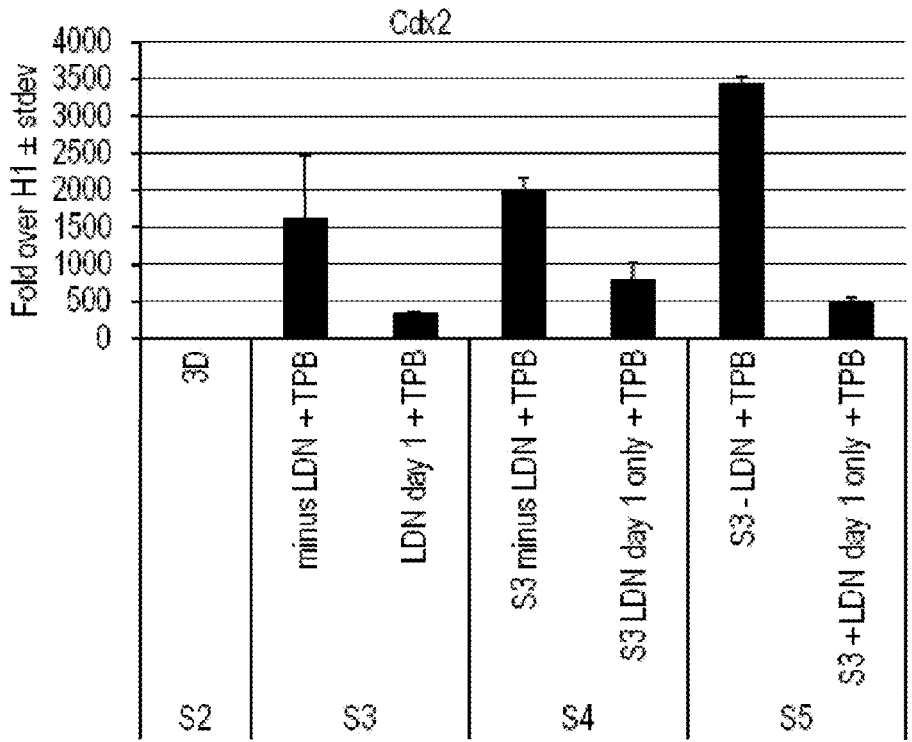

As evidenced by the PCR results shown in FIG. 8A to FIG. 8G, removal of LDN-193189 (BMP inhibitor) from stage 3 abolishes expression of pro-endocrine genes NGN3 (FIG. 8C); NeuroD (FIG. 8D); chromogranin (FIG. 8E) at stage 4 and stage 5. However, expression of PDX-1 (FIG. 8B) and NKX6.1 (FIG. 8A) are not significantly downregulated as compared to NGN3 and NeuroD at stages 4-5. Furthermore, complete removal of LDN-193189 at stage 3 results in a significant increase in CDX2 expression (FIG. 7F). Addition of LDN-193189 for the first day of stage 3 followed by its removal at days 2-3 of stage 3 significantly boosted expression of NGN3 and NeuroD while decreasing CDX2 and SOX2 expression at stage 4. Cultures where LDN-193189 was retained for the duration of stage 3 showed a very high expression of SOX2 (FIG. 8G) at S3-S4. This data shows that BMP inhibition on day 1 of stage 3 is sufficient to trigger pancreatic endocrine markers while suppressing SOX2 and CDX2 expression.

In summary, BMP inhibition is required at day 1 of stage 3 to induce formation of endocrine precursor cells at stages 4-5 and to maintain expression of PDX-1 and NKX6.1 while suppressing SOX2 expression. Furthermore, addition of a PKC activator at stages 3 further enhanced expression of PDX-1 and NKX6.1.

Example 4

Inhibition of BMP Signaling at Day 1 of Stage 3 is Sufficient to Generate Pancreatic Precursor Cells at Stage 4, while Inhibition of BMP Signaling on Last Day of Stage 3 Results in Significantly Lower Expression of Endocrine Markers This example shows that early inhibition of BMP signaling at stage 3 allows for induction of pancreatic endocrine precursor markers while inhibition of BMP signaling late at stage 3 significantly lowers expression level of endocrine precursor markers at stag4.

Cells of the human embryonic stem cells line H1 at various passages (passage 40 to passage 52) were seeded as single cells at a density of 100,000 cells/cm² on MATRIGEL™ (1:30 dilution) coated dishes in mTesr™1 media supplemented with 10 µM of Y27632. Forty eight hours post seeding, cultures were differentiated into cells of the pancreatic endocrine lineage as follows:

a. Stage 1 (Definitive Endoderm (DE)—4 days): Prior to start of DE, the cultures were washed and incubated with incomplete PBS (no Mg or Ca) for 30 seconds followed by addition of the stage 1 media. Human embryonic stem cells cultured as single cells on MATRIGEL™-coated dishes were treated for one day with MCDB-131 medium supplemented with 0.1% fatty acid-free BSA, 0.0012 g/ml sodium bicarbonate, 1× GlutaMax™, 2.5 mM D-Glucose, 100 ng/ml GDF8 and 1.5 µM MCX compound (GSK3B inhibitor). Cells were then treated for three days with MCDB-131 medium supplemented with 0.1% fatty acid-free BSA, 0.0012 g/ml sodium bicarbonate, 1× GlutaMax™, 2.5 mM glucose, and 100 ng/ml GDF8.

b. Stage 2 (Primitive gut tube—3 days): Stage 1 cells were treated for three days with MCDB-131 supplemented with 0.1% fatty acid-free BSA, 0.0012 g/ml sodium bicarbonate, 1× GlutaMax™, 2.5 mM D-Glucose, and 50 ng/ml FGF7.

c. Stage 3 (Foregut—3 days): Stage 2 cells were treated with MCDB-131 medium supplemented with a 1:200 dilution of ITS-X, 2.5 mM Glucose, 1× GlutaMax™, 0.0015 g/ml sodium bicarbonate, 2% fatty acid-free BSA, 0.25 µM SANT-1, 50 ng/ml FGF7, 2 µM RA and the combinations listed in Table III, below for three days.

TABLE III

Stage 3 Treatments

| | | 20 ng/ml AA | LDN-193189 | 1 µM Alk5 inhibitor (SCIO compound) | TPB |
|---|---|---|---|---|---|
| A | S3D1 | + | — | — | +200 nM |
|   | D2-3 | + | — | — | +200 nM |
| B | D1 | — | +100 nM | +1 µM | — |
|   | D2-3 | + | — | — | +200 nM |
| C | D1 | — | +100 nM | +1 µM | +100 nM |
|   | D2-3 | + | — | — | +200 nM |
| D | D1 | — | +100 nM | +1 µM | +200 nM |
|   | D2-3 | + | — | — | +200 nM |
| E | D1 | + | — | — | +100 nM |
|   | D2-3 | + | +100 nM (on day 3 only) | — | +100 nM | d. Stage 4 (Pancreatic foregut precursor—3 days): Stage 3 cells were treated with MCDB-131 medium supplemented with a 1:200 dilution of ITS-X, 2.5 mM Glucose, 1× GlutaMax™, 0.0015 g/ml sodium bicarbonate, 2% fatty acid-free BSA, 0.25 µM SANT-1, 100 nM TPB, 200 nM LDN-193189, 2 µM ALk5 inhibitor, and 100 nM CYP26A inhibitor for three days.

Figure 9A:
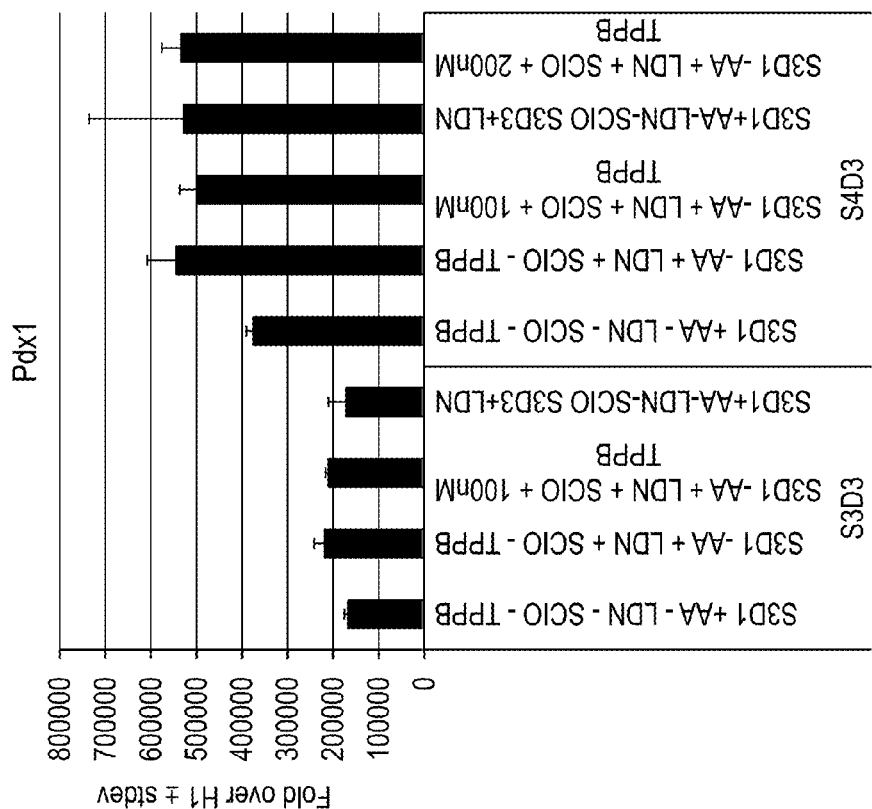
Figure 9B:
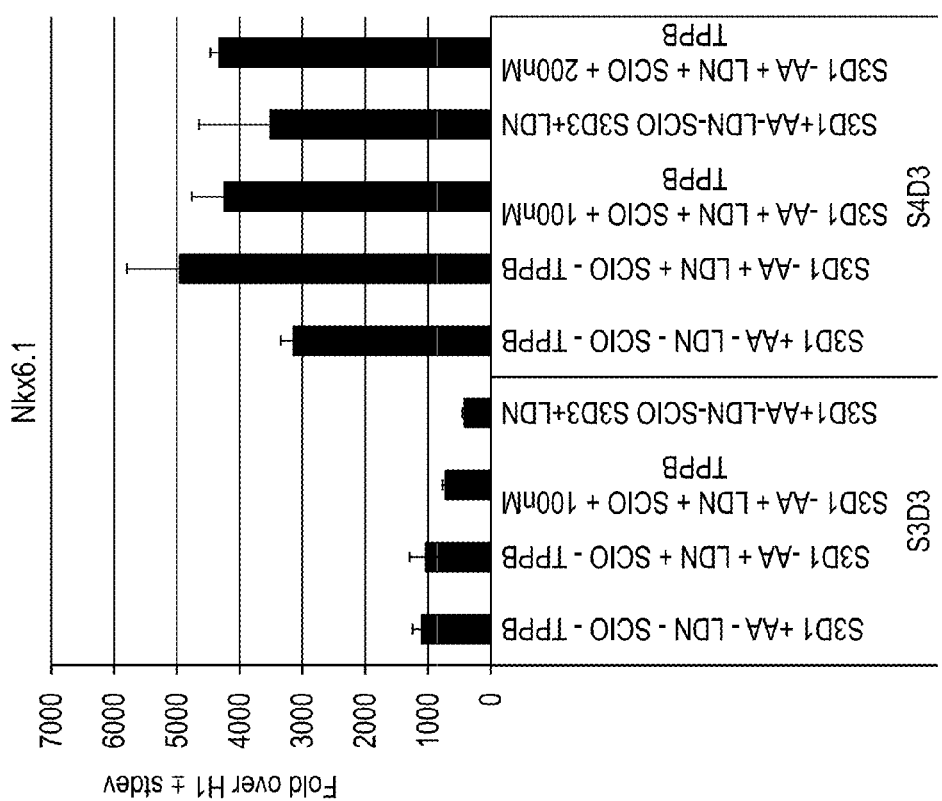
Figure 9D:
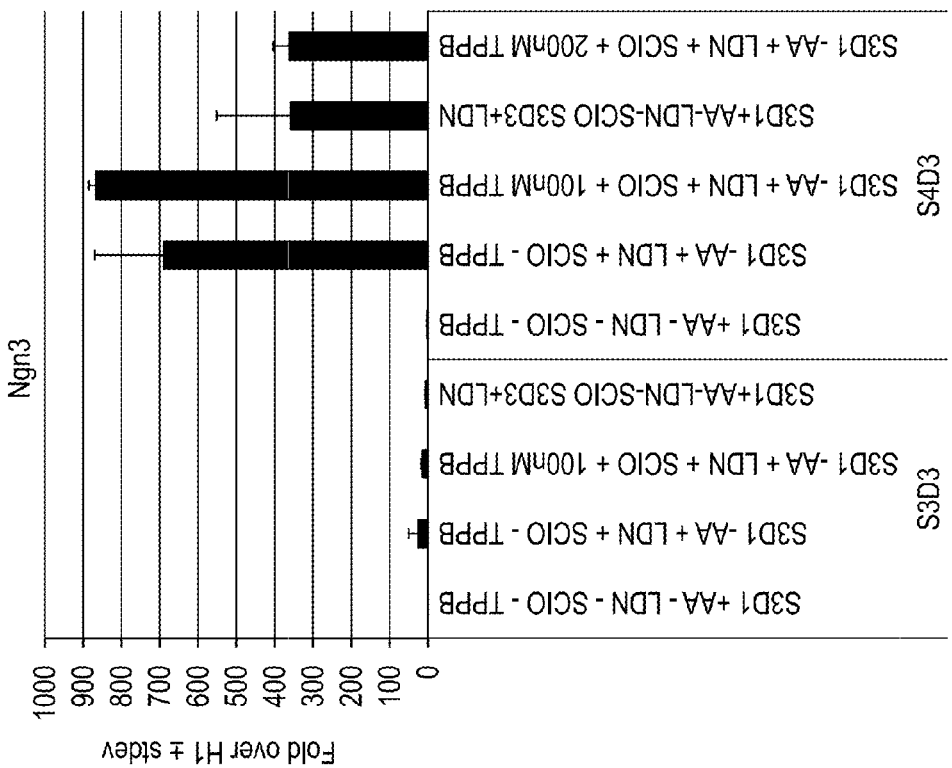
Figure 9C:
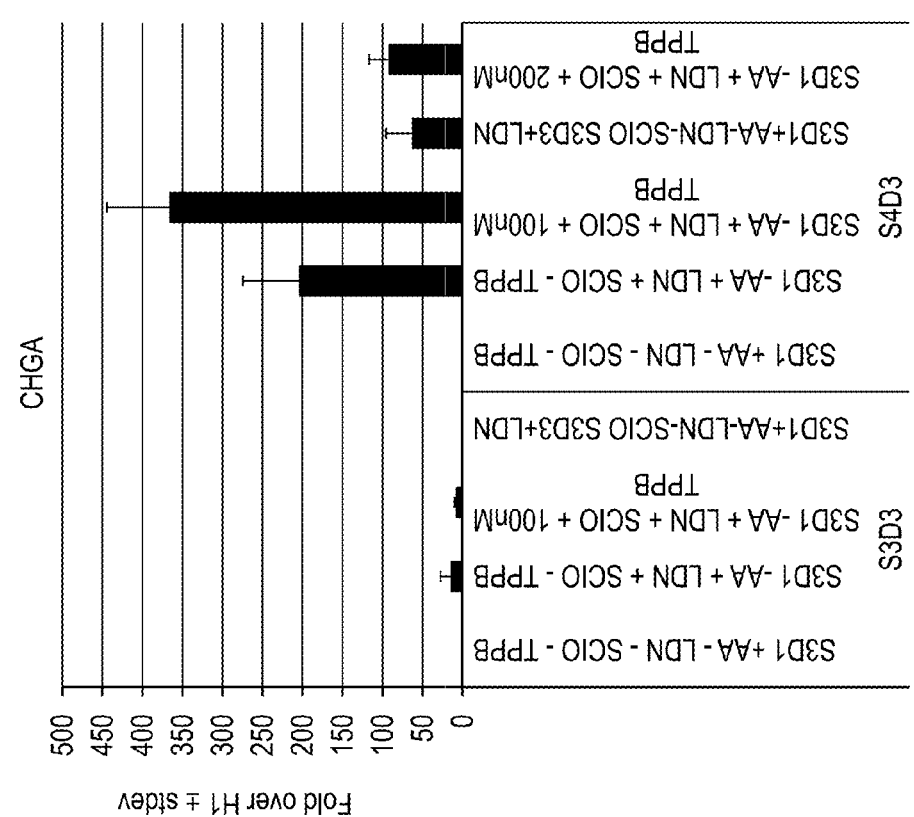
Figure 9E:
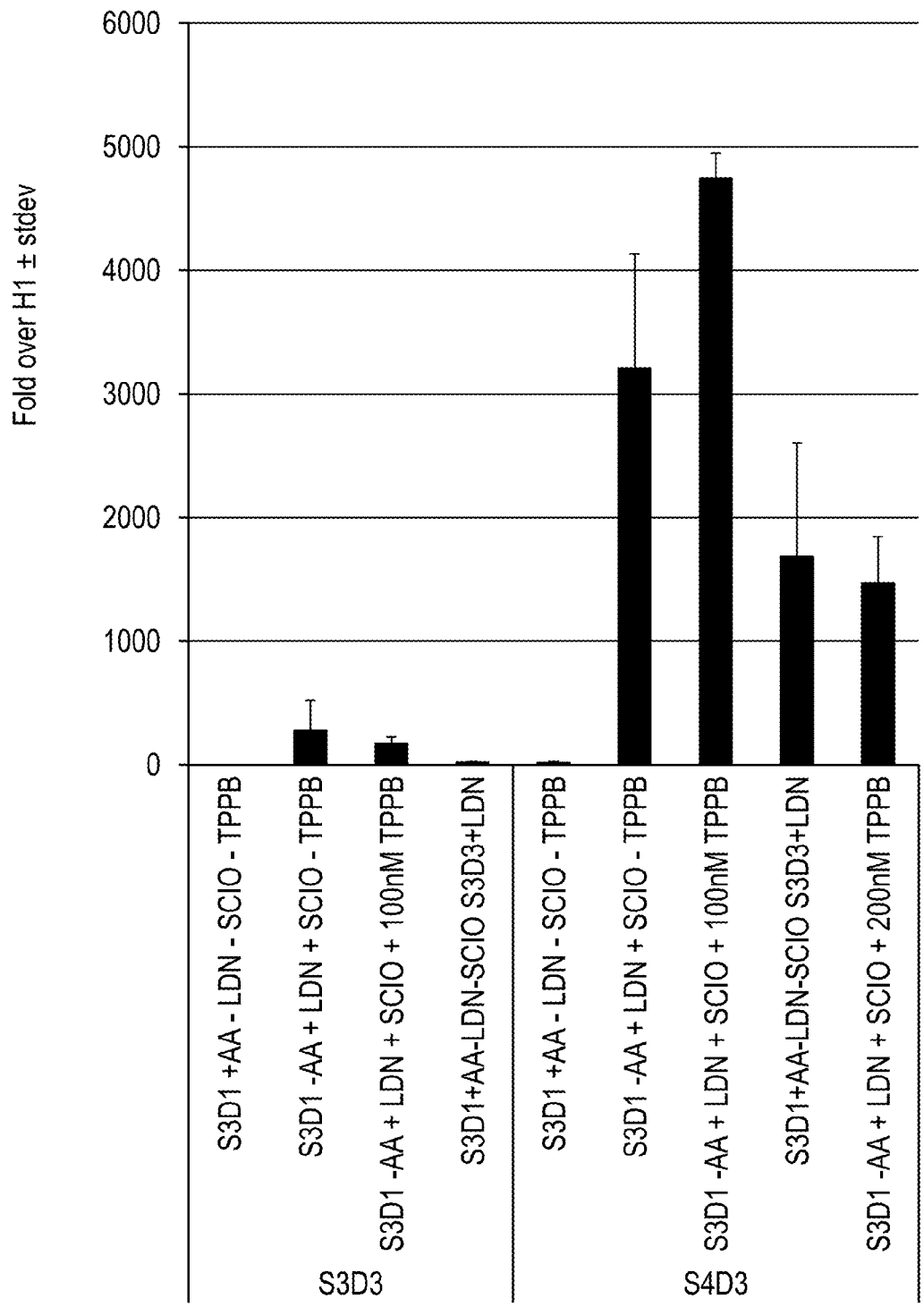
Figure 9H:
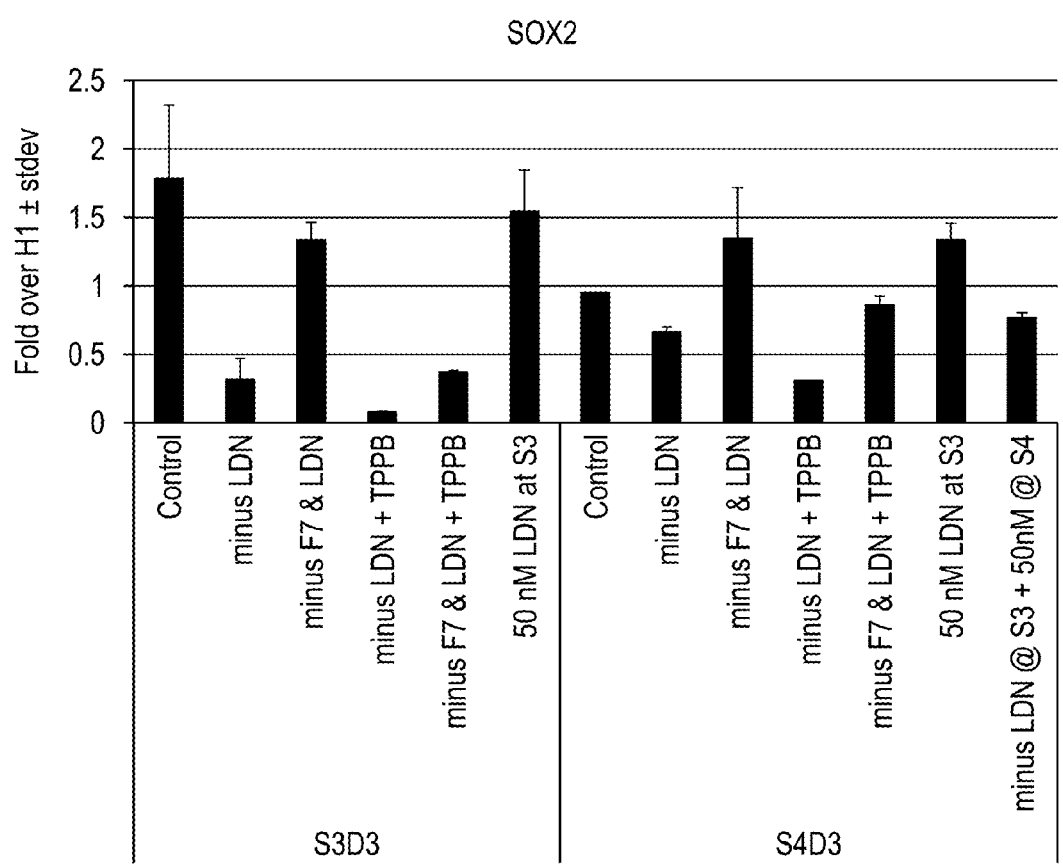
Figure 10D:
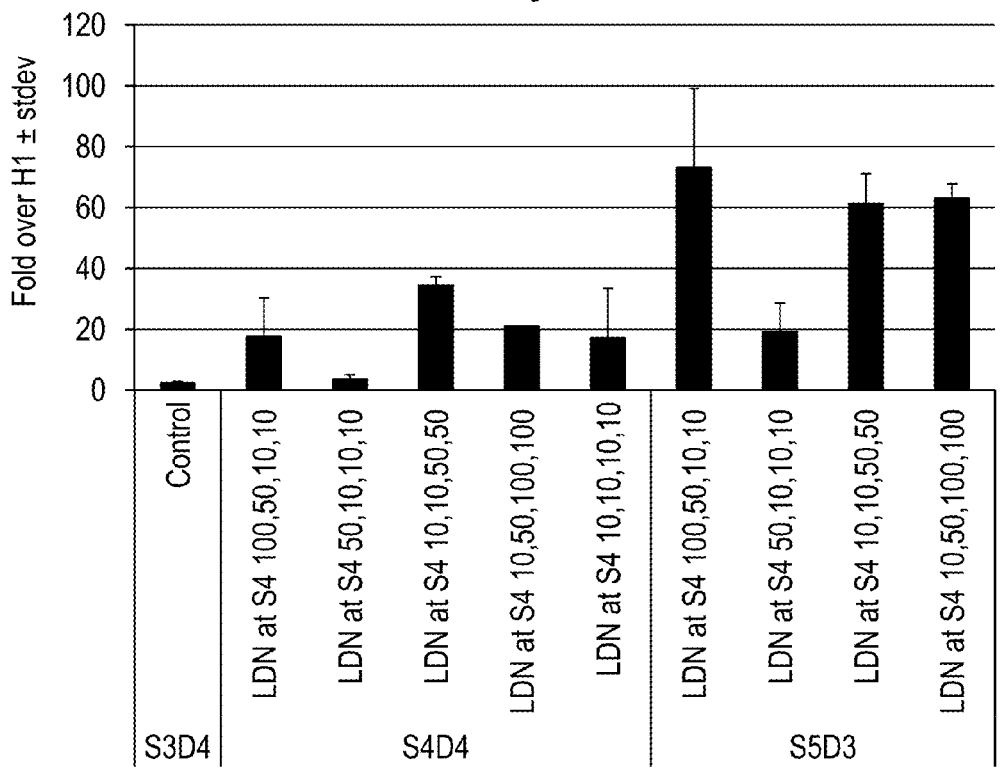
Figure 10E:
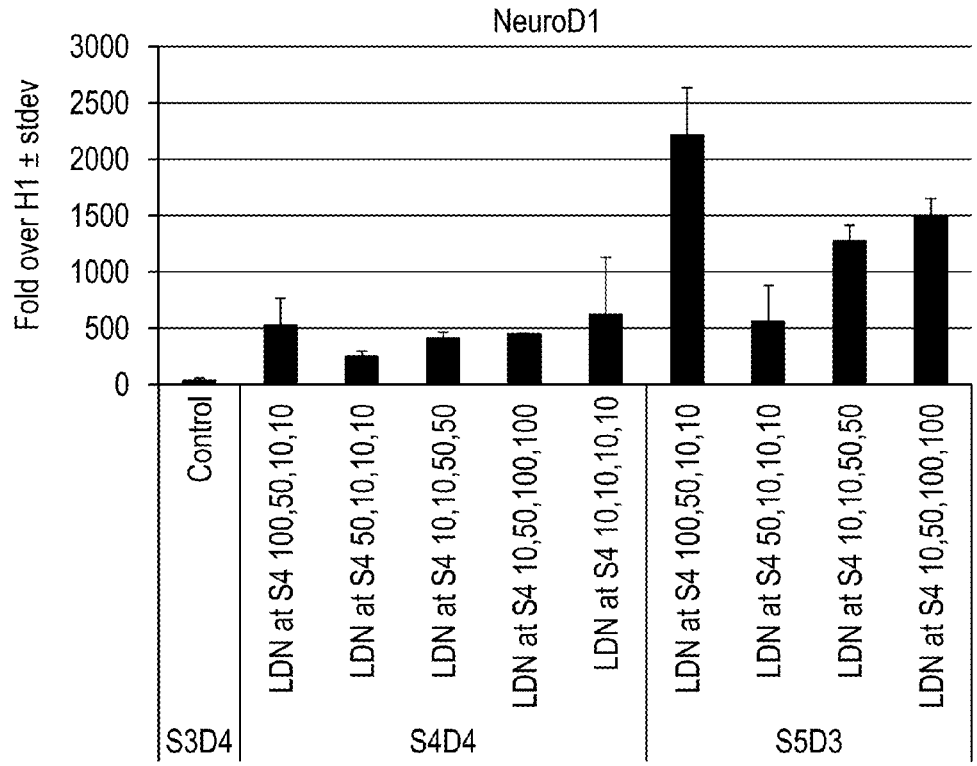
Figure 10F:
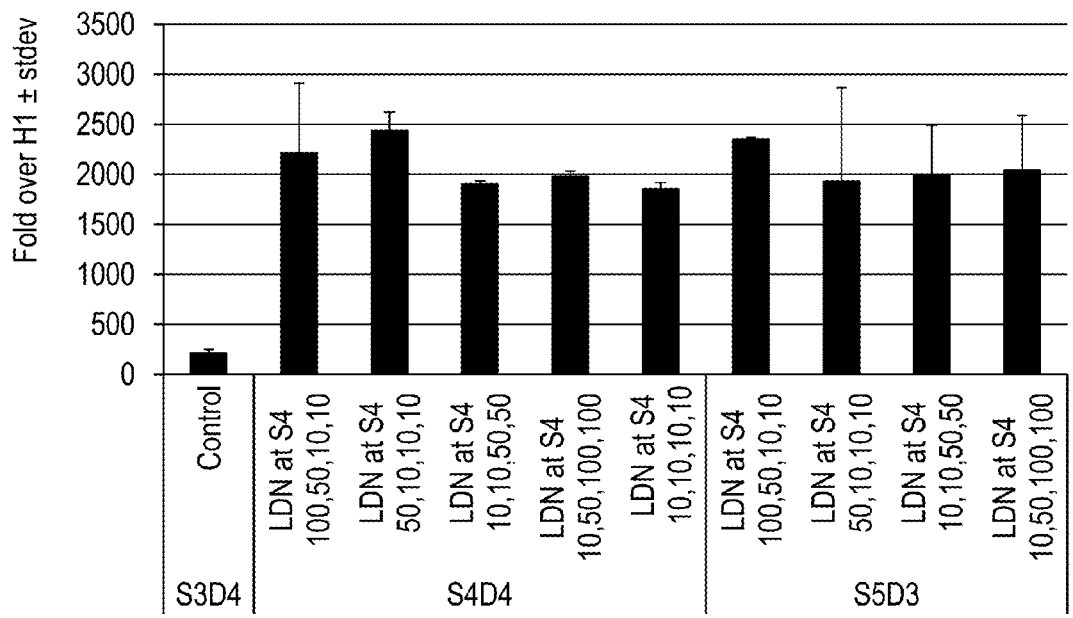
Figure 10G:
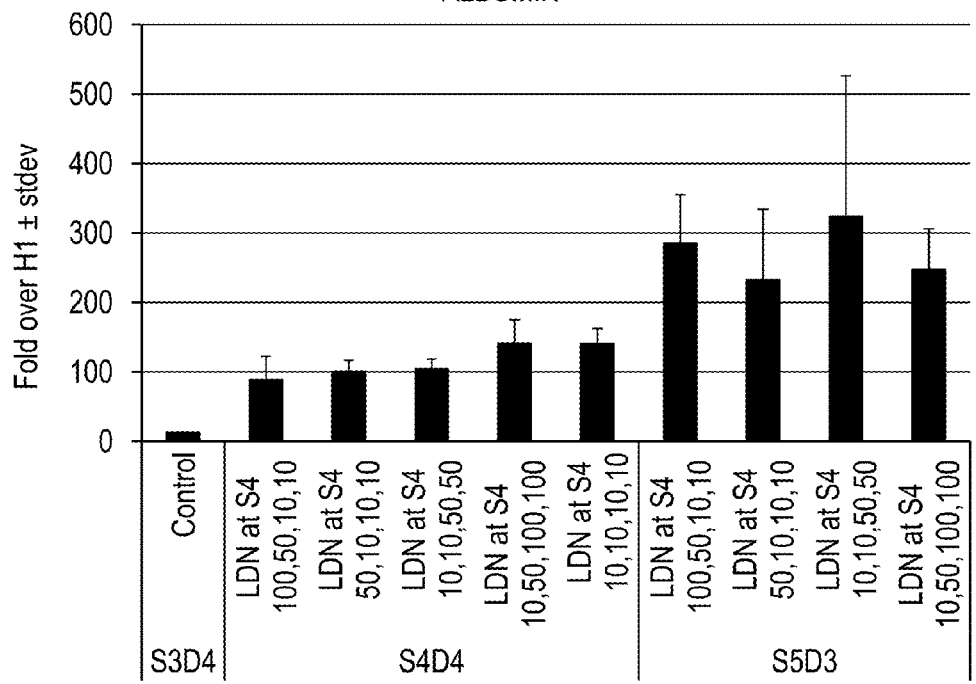
Figure 10H:
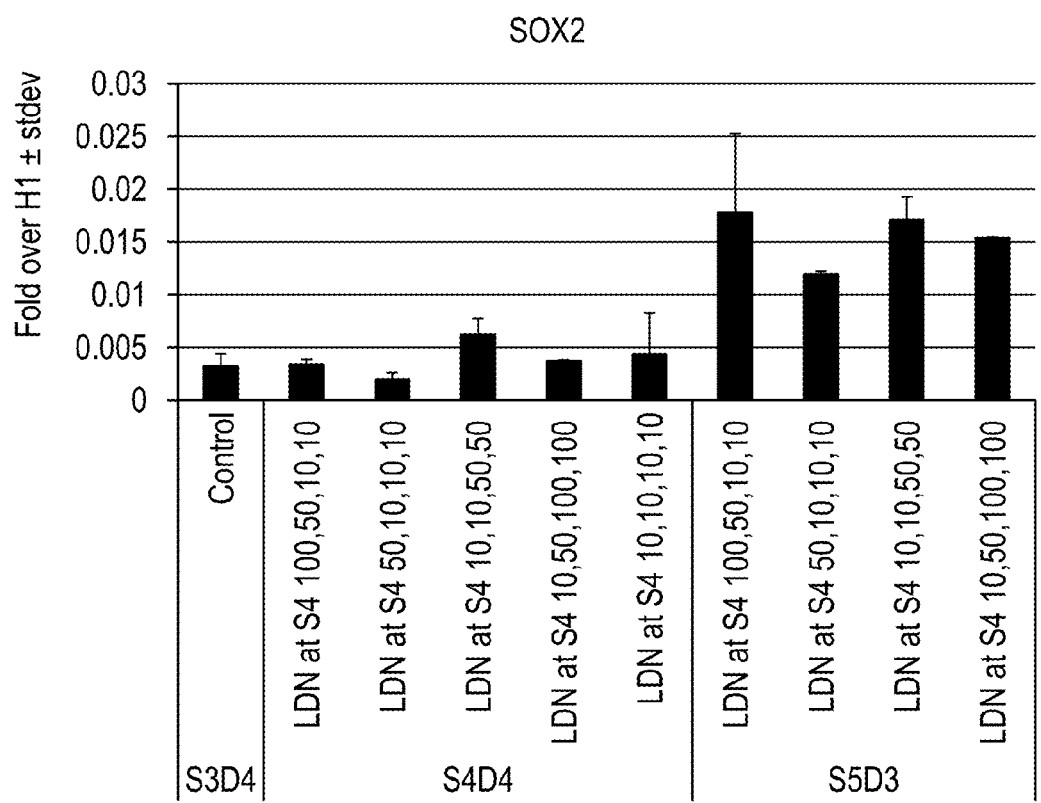
Figure 11A:
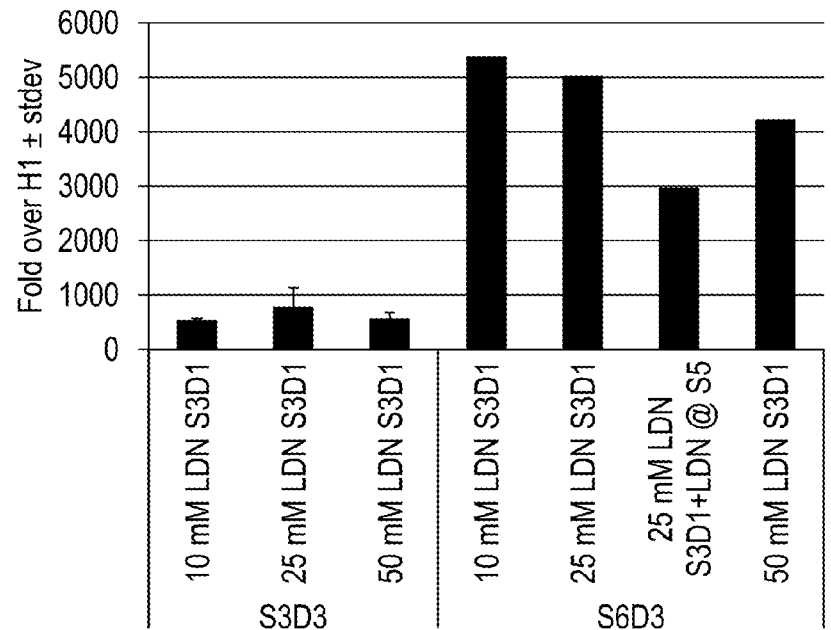
Figure 11B:
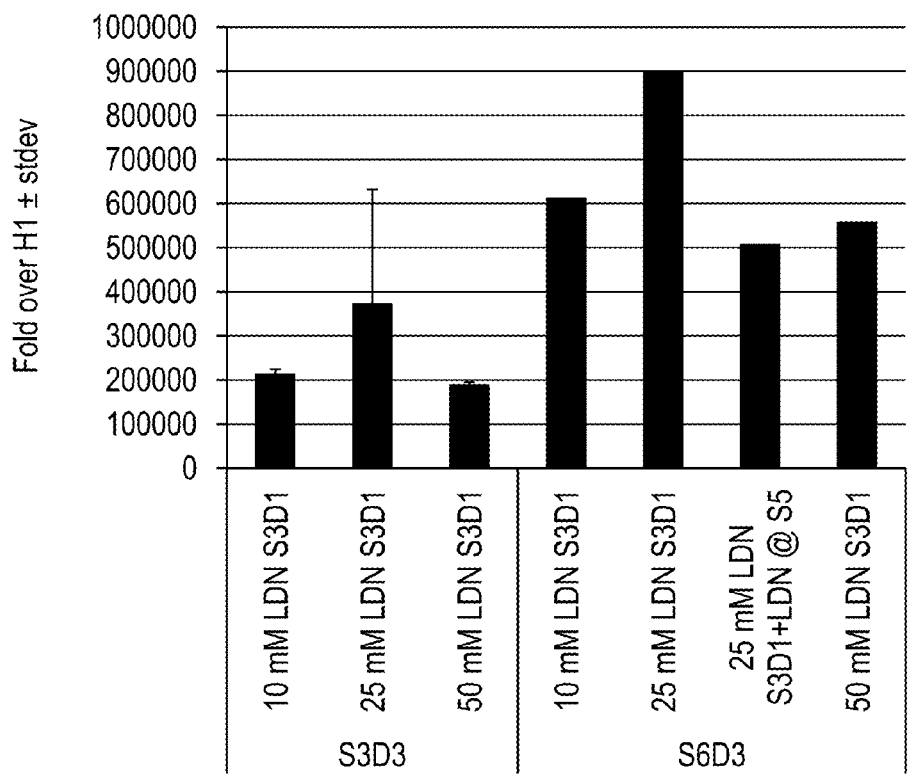
Figure 11C:
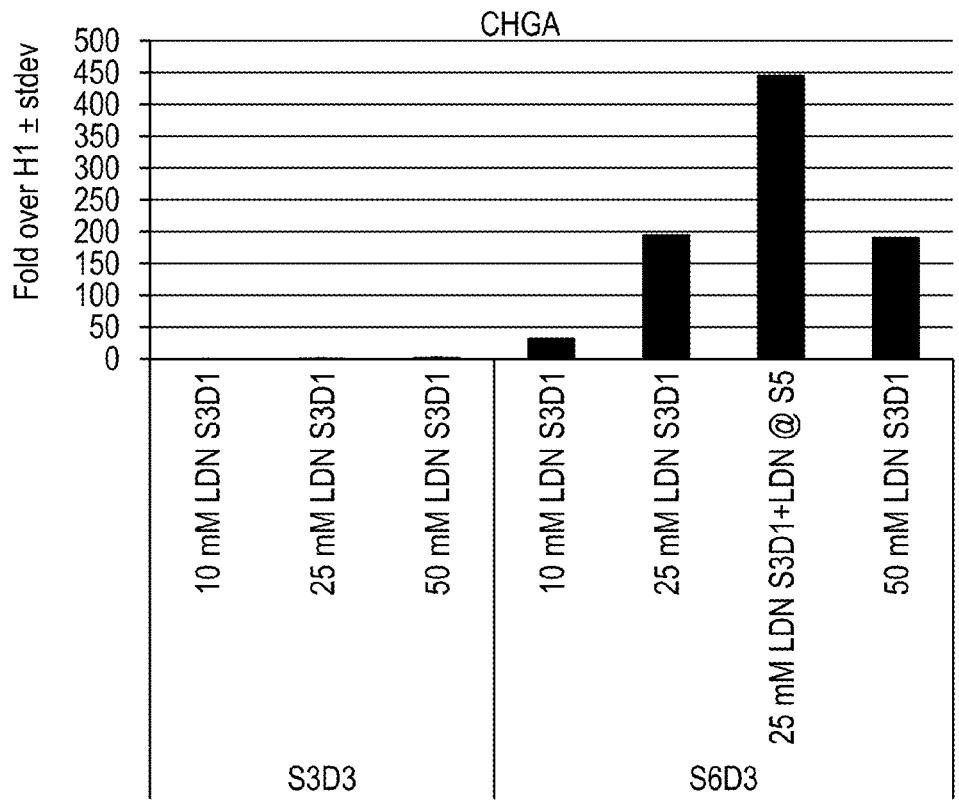
Figure 11D:
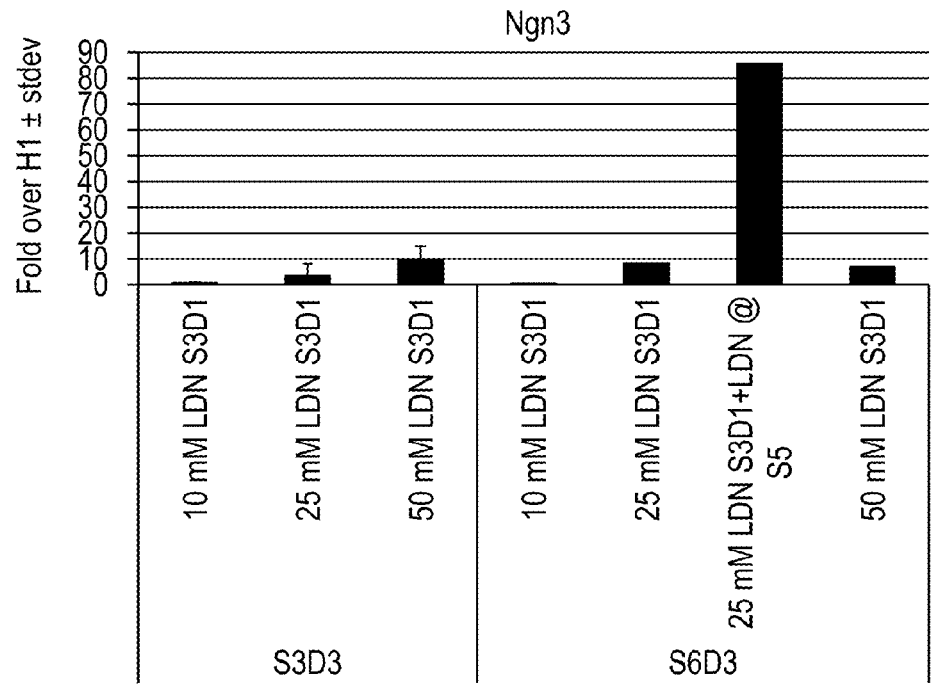
Figure 11E:
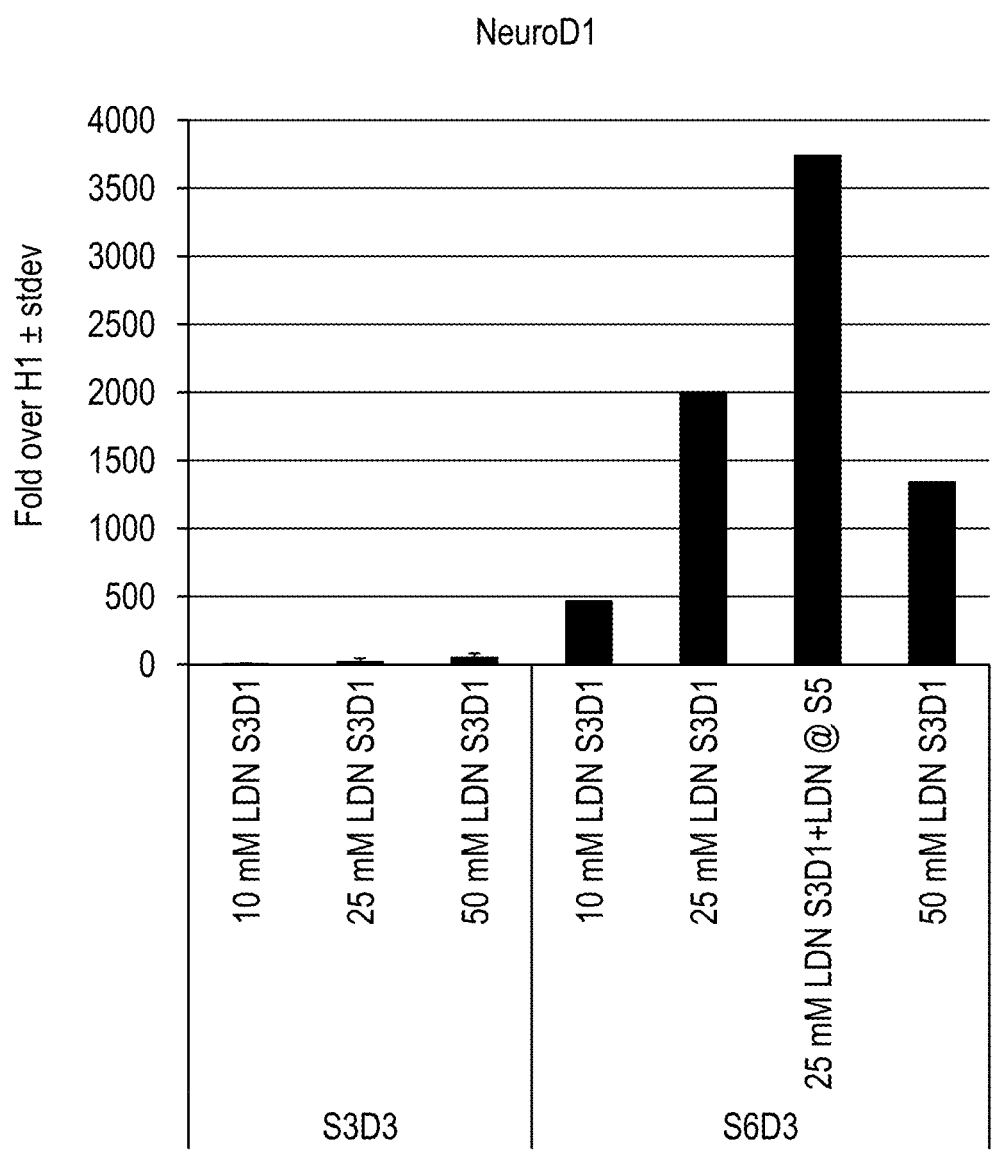
Figure 11F:
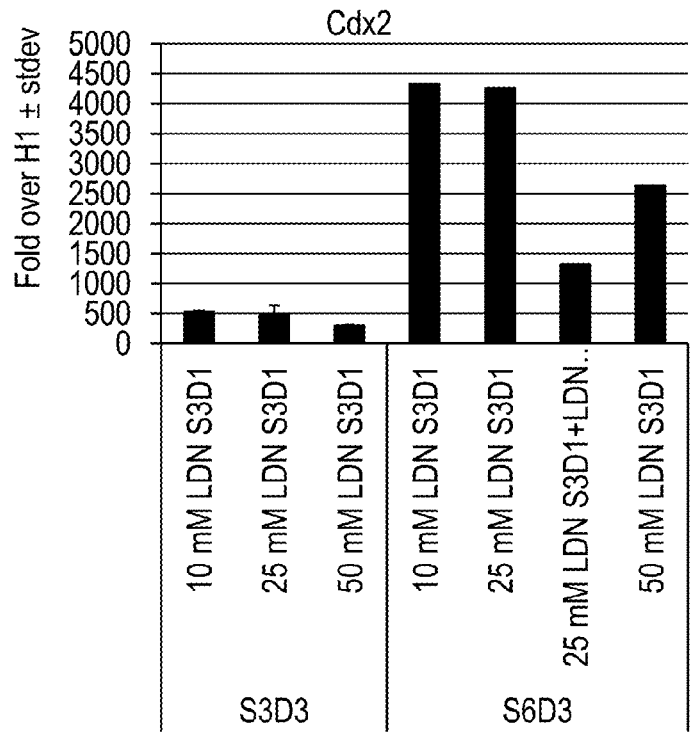
Figure 11G:
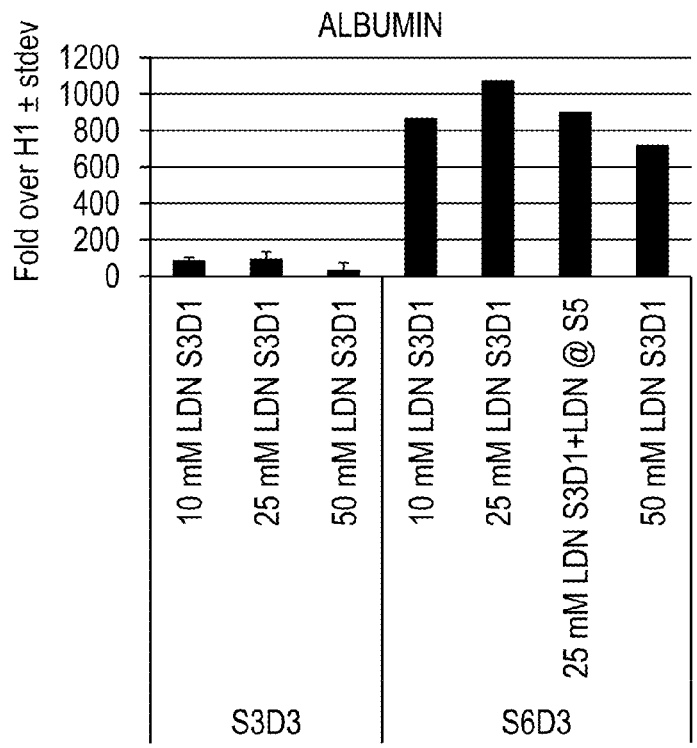

FIG. 9A to FIG. 9H depict the gene expression profile of pancreatic endoderm, endocrine precursor, and foregut endoderm markers for the combinations of culture conditions listed above. Consistent with previous example, blocking of BMP pathway on the first day of stage 3 is critical for the subsequent induction of the endocrine program as measured by expression of the pan-endocrine marker, chromogranin. (See FIG. 9C.) However, addition of the BMP inhibitor at day one of stage 3 triggers expression of endocrine markers at subsequent stages. Furthermore, addition of the BMP inhibitor at day one of stage 3 also decreased expression of foregut marker, SOX2, at stages 3-4 (FIG. 9H). However, addition of BMP inhibitor only at last day of stage 3 shows significantly higher expression of SOX2 at end of stage 3 as compared to cells treated with the BMP inhibitor only on the first day of stage 3. The expression levels shown in FIG. 9A to FIG. 9H are relative to the expression levels in undifferentiated H1 cells which have a very high expression level of SOX2. Besides being a marker of anterior foregut, SOX2 is a well-known transcription factor important in maintenance of pluripotency of ES cells. This example further supports previous results highlighting the sensitivity of stage 3 cultures to the duration and kinetics of BMP signaling and subsequent impact on pancreatic endocrine induction and expression of SOX2.

Example 5

Optimal Dose of BMP Inhibition at Pancreatic Foregut Stage (Stage 4)

Previous examples described the optimal duration of BMP inhibition at stage 3. This example identifies the optimal dose of BMP inhibitor at S4 media.

Cells of the human embryonic stem cell line H1 at various passages (passage 40 to passage 52) were seeded as single cells at a density of 100,000 cells/cm² on MATRIGEL™ (1:30 dilution) coated dishes in mTesr™1 media and 10 µM of Y27632. Forty eight hours post seeding, cultures were differentiated into pancreatic endocrine lineage as follows:

a. Stage 1 (Definitive Endoderm (DE)—4 days): Prior to start of DE, the cultures were washed and incubated with incomplete PBS (no Mg or Ca) for 30 seconds followed by addition of the stage 1 media. Human embryonic stem cells cultured as single cells on MATRIGEL™-coated dishes were treated with MCDB-131 medium supplemented with 0.1% fatty acid-free BSA, 0.0012 g/ml sodium bicarbonate, 1× GlutaMax™, 2.5 mM D-Glucose, 100 ng/ml GDF8, and 1 µM MCX compound (GSK3B inhibitor) for one day. Cells were then treated with MCDB-131 medium supplemented with 0.1% fatty acid-free BSA, 0.0012 g/ml sodium bicarbonate, 1× GlutaMax™, 2.5 mM glucose, and 100 ng/ml GDF8 for days 2-4.

b. Stage 2 (Primitive gut tube—3 days): Stage 1 cells were treated with MCDB-131 medium supplemented with 0.1% fatty acid-free BSA, 0.0012 g/ml sodium bicarbonate, 1× GlutaMax™, 2.5 mM D-Glucose, and 50 ng/ml FGF7 for three days.

c. Stage 3 (Foregut—4 days): Stage 2 cells were treated with MCDB-131 medium supplemented with a 1:200 dilution of ITS-X, 2.5 mM, Glucose, 1× GlutaMax™, 0.0015 g/ml sodium bicarbonate, 2% fatty acid-free BSA, 0.25 µM SANT-1, 50 ng/ml FGF7, 2 µM RA, 20 ng/ml of Activin-A, 100 nM LDN-193189, and 100 nM TPB for one day. Cells were then cultured in MCDB-131 medium supplemented with a 1:200 dilution of ITS-X, 2.5 mM, Glucose, 1× GlutaMax™, 0.0015 g/ml sodium bicarbonate, 2% fatty acid-free BSA, 0.25 µM SANT-1, 50 ng/ml FGF7, 2 µM RA, 20 ng/ml of Activin-A, and 100 nM TPB for three days.

d. Stage 4 (Pancreatic foregut precursor—4 days): Stage 3 cells were treated with MCDB-131 medium supplemented with a 1:200 dilution of ITS-X, 2.5 mM Glucose, 1× GlutaMax™, 0.0015 g/ml sodium bicarbonate, 2% fatty acid-free BSA, 200 nM LDN-193189-193189, 2 µM ALk5 inhibitor, 100 nM CYP26A inhibitor, and the concentrations of LDN-193189 listed on Table IV (below) for days 1-4 of stage 4:

TABLE IV

Concentrations of LDN-193189 Used at S4

| | Condition A | Condition B | Condition C | Condition D | Condition E |
|---|---|---|---|---|---|
| S4D1 | 100 nM | 50 nM | 10 nM | 10 nM | 10 nM |
| S4D2 | 50 nM | 10 nM | 50 nM | 10 nM | 10 nM |
| S4D3 | 10 nM | 10 nM | 100 nM | 50 nM | 10 nM |
| S4D4 | 10 nM | 10 nM | 100 nM | 50 nM | 10 nM | d. Stage 5 (Pancreatic endoderm/endocrine precursor—3 days): Stage 4 cells were treated with MCDB-131 medium supplemented with a 1:200 dilution of ITS-X, 2.5 mM Glucose, 1× GlutaMax™, 0.0015 g/ml sodium bicarbonate, 2% fatty acid-free BSA, 50 nM LDN-193189, and 1 µM ALk5 inhibitor for three days.

The results of real-time PCR analyses of cells harvested after the treatments above are shown in FIG. 10A to FIG. 10H. This figure shows that addition of 50 nM or 100 nM of LDN-193189 at days 1, 2, 3, or 4 of S4 can prolong the expression of endocrine markers while maintaining a low expression of SOX2 at S4-S5. (See FIG. 10A to FIG. 10H.)

Example 6

Optimal Dose of BMP Inhibition at Foregut Stage (Stage 3)

This example identifies the optimal dose of BMP inhibition at stage 3 and subsequent effects on endocrine markers at stage 6.

Cells of the human embryonic stem cell line H1 at various passages (passage 40 to passage 52) were seeded as single cells at a density of 100,000 cells/cm² on MATRIGEL™ (1:30 dilution) coated dishes in mTesr™1™ media supplemented with 10 µM of Y27632. Forty eight hours post seeding, cultures were differentiated into cells of the pancreatic endocrine lineage as follows:

a. Stage 1 (Definitive Endoderm (DE)—4 days): Prior to start of DE, the cultures were washed and incubated with incomplete PBS (no Mg or Ca) for 30 seconds followed by addition of the stage 1 media. Human embryonic stem cells cultured as single cells on MATRIGEL™-coated dishes were treated with MCDB-131 medium supplemented with 0.1% fatty acid-free BSA, 0.0012 g/ml sodium bicarbonate, 1× GlutaMax™, 2.5 mM D-Glucose, 100 ng/ml GDF8, and 1.5 µM MCX compound (GSK3B inhibitor) for one day. Cells were then treated with MCDB-131 medium supplemented with 0.1% fatty acid-free BSA, 0.0012 g/ml sodium bicarbonate, 1× GlutaMax™, 2.5 mM glucose, and 100 ng/ml GDF8 for days 2-4.

b. Stage 2 (Primitive gut tube—3 days): Stage 1 cells were treated with MCDB-131 medium supplemented with 0.1% fatty acid-free BSA, 0.0012 g/ml sodium bicarbonate, 1× GlutaMax™, 2.5 mM D-Glucose, and 50 ng/ml FGF7 for three days.

c. Stage 3 (Foregut—3 days): Stage 3 cells were treated with MCDB-131 medium supplemented with a 1:200 dilution of ITS-X, 2.5 mM Glucose, 1× GlutaMax™, 0.0015 g/ml sodium bicarbonate, 2% fatty acid-free BSA, 0.25 µM SANT-1, 50 ng/ml FGF7, 2 µM RA, 20 ng/ml Activin-A, 100 nM TPB, and 10-50 nM LDN-193189 for one day. Cells were then treated with MCDB-131 medium supplemented with a 1:200 dilution of ITS-X, 2.5 mM Glucose, 1× GlutaMax™, 0.0015 g/ml sodium bicarbonate, 2% fatty acid-free BSA, 0.25

µM SANT-1, 50 ng/ml FGF7, 2 µM RA, 20 ng/ml Activin-A, and 100 nM TPB for two days.

d. Stage 4 (Pancreatic foregut precursor—3 days): Stage 3 cells were treated with MCDB-131 medium supplemented with a 1:200 dilution of ITS-X, 2.5 mM Glucose, 1× GlutaMax™, 0.0015 g/ml sodium bicarbonate, 2% fatty acid-free BSA, 20 nM LDN-193189; 2 µM ALk5 inhibitor; 100 nM CYP26 A inhibitor, and 100 nM TPB for three days.

e. Stage 5 (Pancreatic endoderm/endocrine precursor—3 days): Stage 4 cells were treated with MCDB-131 medium supplemented with a 1:200 dilution of ITS-X; 2.5 mM Glucose; 1× GlutaMax™; 0.0015 g/ml sodium bicarbonate; 2% fatty acid-free BSA; +/−25 nM LDN-193189 and/or 2 µM ALk5 inhibitor for three days.

f. Stage 6 (Pancreatic endocrine hormone producing—3 days): Stage 5 cells were treated with MCDB-131 medium supplemented with a 1:200 dilution of ITS-X; 2.5 mM Glucose; 1× GlutaMax™; 0.0015 g/ml sodium bicarbonate; and 2% fatty acid-free BSA for three days.

FIG. 11A to FIG. 11H show that a low to moderate inhibition of BMP on the first day of stage 3 is required to trigger expression of endocrine markers while maintaining a low expression of SOX2. Furthermore, BMP inhibition at stage 5 while enhancing endocrine markers also led to upregulation of SOX2 expression.

The data in this Example further confirms the results presented in the previous examples. The data confirms that a precise modulation of the BMP pathway at stages 3-5 is required to trigger induction of pancreatic endocrine markers while suppressing SOX2 expression.

Example 7

Optimal Window for BMP Inhibition at S3 (Foregut Stage)

This example identifies the optimal window of time at stage 3 for inhibition of BMP signaling while preserving endocrine induction at later stages and lowering expression fo SOX2.

Cells of the human embryonic stem cells line H1 at various passages (Passage 40 to passage 52) were seeded as single cells at a density of 100,000 cells/cm² on MATRIGEL™ (1:30 dilution) coated dishes in mTesr™1 media and 10 µM Y27632. Forty eight hours post seeding, cultures were differentiated into pancreatic endocrine lineage as follows:

a. Stage 1 (Definitive Endoderm (DE)—4 days): Prior to start of DE, the cultures were washed and incubated with incomplete PBS (no Mg or Ca) for 30 seconds followed by addition of the stage 1 media. Human embryonic stem cells cultured as single cells on MATRIGEL™-coated dishes were treated with MCDB-131 medium supplemented with 0.1% fatty acid-free BSA, 0.0012 g/ml sodium bicarbonate, 1× GlutaMax™, 2.5 mM D-Glucose, 100 ng/ml GDF8 and 1.5 µM MCX compound for one day. Cells were then treated with MCDB-131 medium supplemented with 0.1% fatty acid-free BSA, 0.0012 g/ml sodium bicarbonate, 1× GlutaMax™, 2.5 mM glucose, and 100 ng/ml GDF8 for days 2-4.

b. Stage 2 (Primitive gut tube—3 days): Stage 1 cells were treated with MCDB-131 medium supplemented with 0.1% fatty acid-free BSA, 0.0012 g/ml sodium bicarbonate, 1× GlutaMax™, 2.5 mM D-Glucose, and 50 ng/ml FGF7 for three days.

c. Stage 3 (Foregut—3 days): Stage 2 cells were treated with MCDB-131 medium supplemented with a 1:200 dilution of ITS-X, 2.5 mM Glucose, 1× GlutaMax™, 0.0015 g/ml sodium bicarbonate, 2% fatty acid-free BSA, 0.25 µM SANT-1, 50 ng/ml FGF7, 2 µM RA, 20 ng/ml Activin-A, and 100 nM TPB, containing 100 nM LDN-193189 for only the first 2 hours, 6 hours, or 24 hours of stage 3.

d. Stage 4 (Pancreatic foregut precursor—3 days): Stage 3 cells were treated with MCDB-131 medium supplemented with a 1:200 dilution of ITS-X, 2.5 mM Glucose, 1× GlutaMax™, 0.0015 g/ml sodium bicarbonate, 2% fatty acid-free BSA, 25 nM LDN-193189, 2 µM ALk5 inhibitor, 100 nM CYP26 A inhibitor, and 100 nM TPB for three days.

e. Stage 5 (Pancreatic endoderm/endocrine precursor—3 days): Stage 4 cells were treated with MCDB-131 medium supplemented with a 1:200 dilution of ITS-X, 2.5 mM Glucose, 1× GlutaMax™, 0.0015 g/ml sodium bicarbonate, 2% fatty acid-free BSA, and 2 µM ALk5 inhibitor for three days.

Figure 12A:
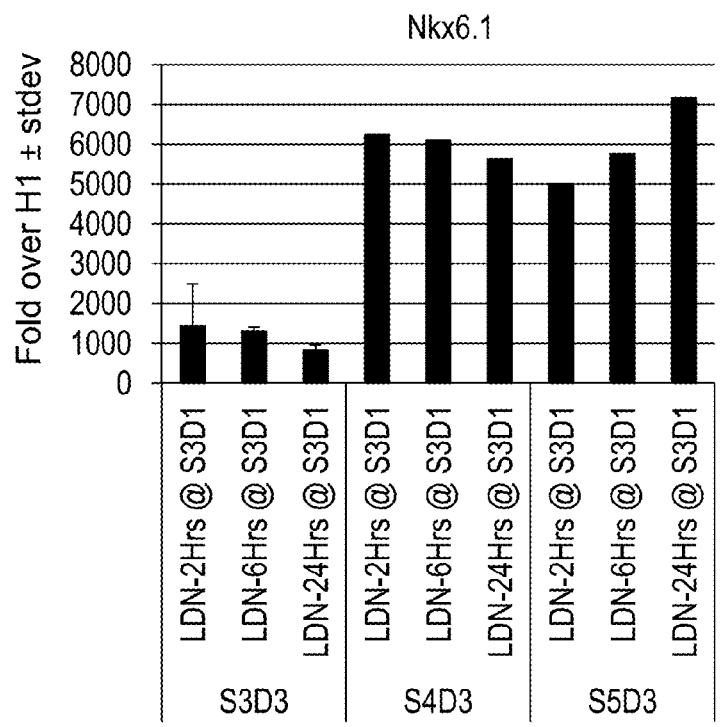
Figure 12B:
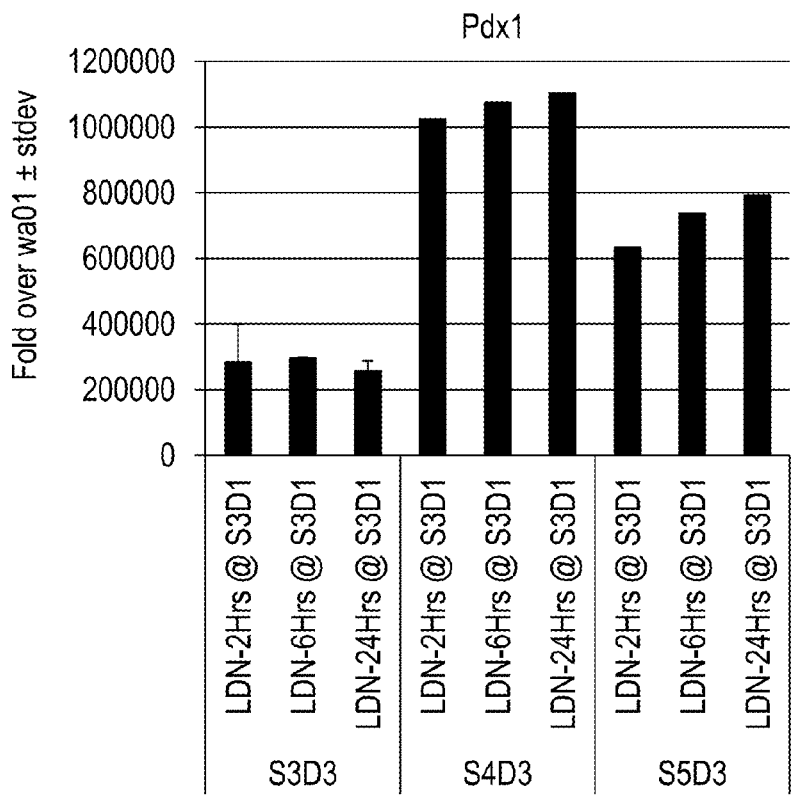
Figure 12E:
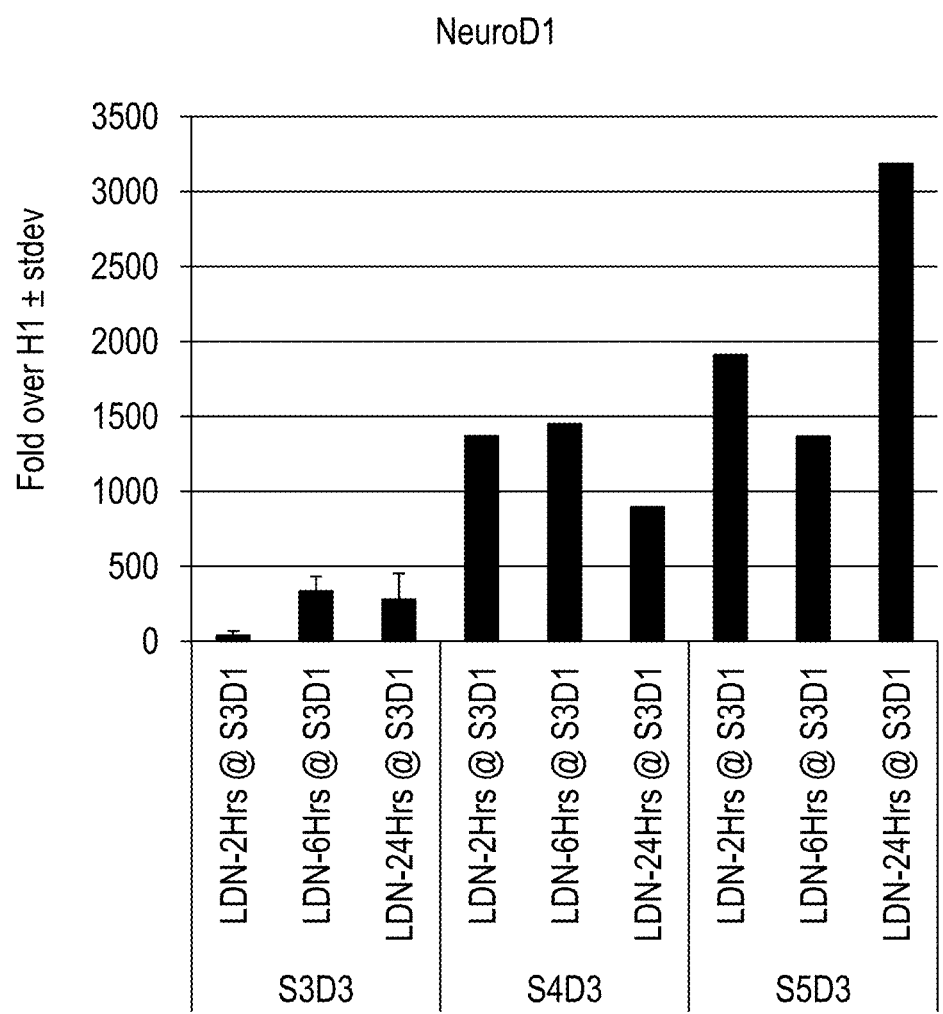
Figure 12F:
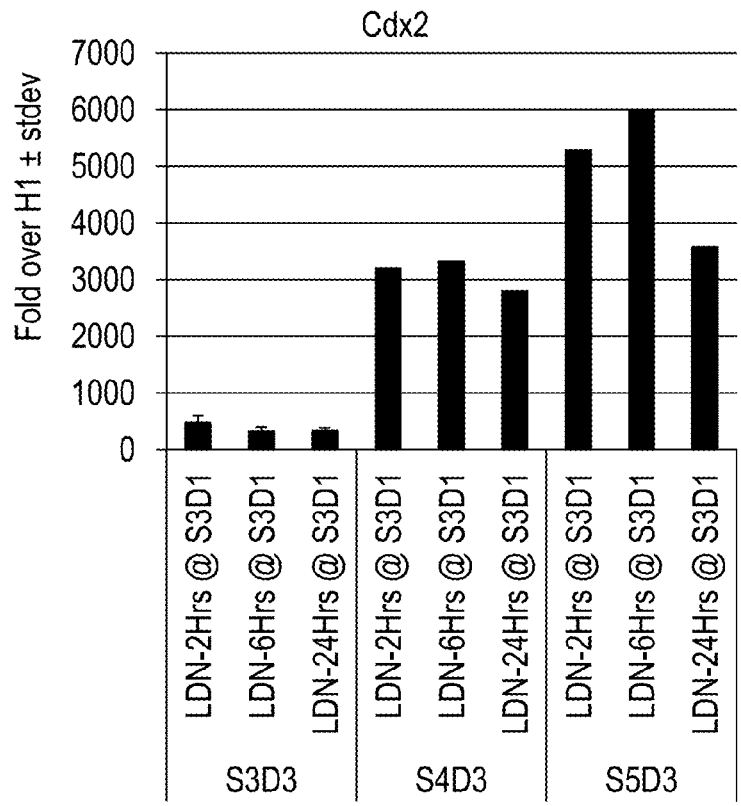
Figure 12G:
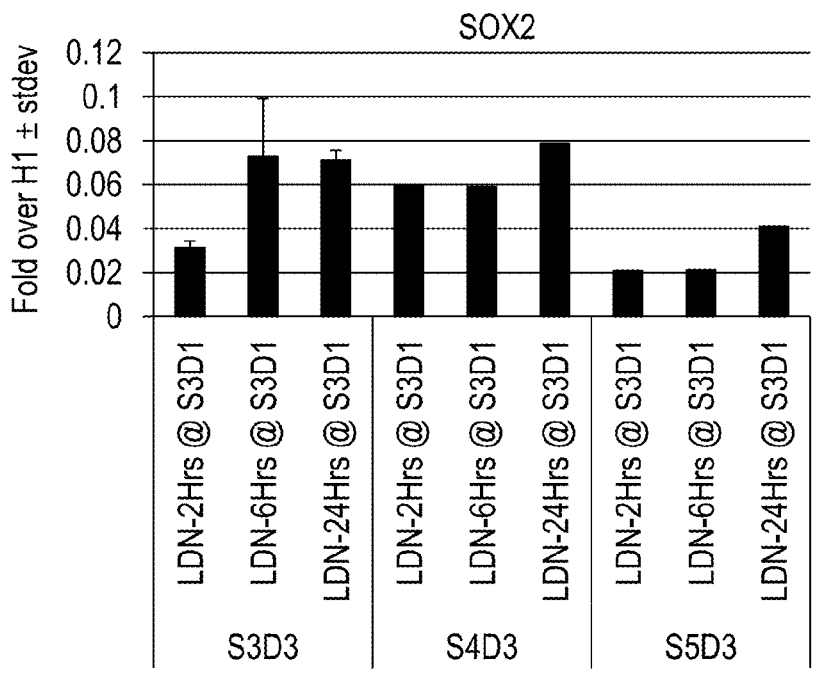

FIG. 12A to FIG. 12G show the real time PCR analyses for data gathered in this example. Treatment at stage 3 for at least 2 hours with a BMP inhibitor can trigger expression of pro-endocrine transcription factors such as Ngn3 (FIG. 12D) and NeuroD (FIG. 12E) while maintaining a very low expression of SOX2 (FIG. 12G) and significantly increases expression of NKX6.1 (FIG. 12A) and PDX-1 (FIG. 12B) at S4-S5. However, at stage 5 day3 CDX2 expression was higher in cells treated for 2 or 6 hours with BMP inhibitor than in cells treated for 24 hours with the inhibitor (FIG. 12F).

The data from this Example suggests that a 24 hour inhibition of the BMP pathway is optimal for maintaining a low level of CDX2 expression and SOX2 expression, and to initiate endocrine differentiation while maintaining a high expression of pancreatic endoderm markers.

Example 8

Optimal Duration of Stages 3 (Foregut Stage) and Stage 4 (Pancreatic Foregut Precursor Stage)

This example was carried out to determine the optimal duration of S3 and S4 in the stepwise differentiation of pluripotent cells to a population of cells of pancreatic endocrine lineage.

Cells of the human embryonic stem cells line H1 at various passages (passage 40 to passage 52) were seeded as single cells at a density of 100,000 cells/cm² on MATRIGEL™ (1:30 dilution)-coated dishes in mTesr™1 media supplemented with 10 µM Y27632. Forty eight hours post seeding, cultures were differentiated into pancreatic endocrine lineage as follows:

a. Stage 1 (Definitive Endoderm (DE)—4 days): Prior to start of DE, the cultures were washed and incubated with incomplete PBS (no Mg or Ca) for 30 seconds followed by addition of the stage 1 media. Human embryonic stem cells cultured as single cells on MATRIGEL™-coated dishes were treated with MCDB-131 medium supplemented with 0.1% fatty acid-free BSA, 0.0012 g/ml sodium bicarbonate, 1× GlutaMax™; 2.5 mM D-Glucose; 100 ng/ml GDF8 and 1.5 µM MCX compound (GSK3B inhibitor) for one day. Cells were then treated with MCDB-131 medium supplemented with 0.1% fatty acid-free BSA; 0.0012 g/ml sodium bicarbonate; 1× GlutaMax™; 2.5 mM glucose, and 100 ng/ml GDF8 for days 2-4; then b. Stage 2 (Primitive gut tube—2 days): Stage 1 cells were treated with MCDB-131 medium supplemented with 0.1% fatty acid-free BSA, 0.0012 g/ml sodium bicarbonate, 1× GlutaMax™, 2.5 mM D-Glucose, and 50 ng/ml FGF7 for two days.

c. Stage 3 (Foregut—2-3 days): Stage 2 cells were treated with MCDB-131 medium supplemented with a 1:200 dilution of ITS-X, 2.5 mM Glucose, 1× GlutaMax™, 0.0015 g/ml sodium bicarbonate, 2% fatty acid-free BSA, 0.25 µM SANT-1, 50 ng/ml FGF7, 2 µM RA, 20 ng/ml Activin-A, and 100 nM TPB, containing 100 nM LDN-193189 for one day. Cells were then treated with MCDB-131 medium supplemented with a 1:200 dilution of ITS-X, 2.5 mM Glucose, 1× GlutaMax™, 0.0015 g/ml sodium bicarbonate, 2% fatty acid-free BSA, 0.25 µM SANT-1, 50 ng/ml FGF7, 2 µM RA, 20 ng/ml Activin-A, and 100 nM TPB.

d. Stage 4 (Pancreatic foregut precursor—2-3 days): Stage 3 cells were treated with MCDB-131 medium supplemented with a 1:200 dilution of ITS-X, 2.5 mM Glucose, 1× GlutaMax™, 0.0015 g/ml sodium bicarbonate, 2% fatty acid-free BSA, 25 nM LDN-193189, 100 nM CYP26 A inhibitor, and 100 nM TPB for two or three days.

e. Stage 5 (Pancreatic endoderm/endocrine precursor—2 days): Stage 4 cells were treated with MCDB-131 medium supplemented with a 1:200 dilution of ITS-X, 2.5 mM Glucose, 1× GlutaMax™, 0.0015 g/ml sodium bicarbonate, 2% fatty acid-free BSA, and 1 µM ALk5 inhibitor for two days.

f. Stage 6 (Pancreatic endocrine precursor/hormone-2 days): Stage 5 cells were treated with MCDB-131 medium supplemented with a 1:200 dilution of ITS-X, 2.5 mM Glucose, 1× GlutaMax™, 0.0015 g/ml sodium bicarbonate, and 2% fatty acid-free BSA for two days.

Figure 13A:
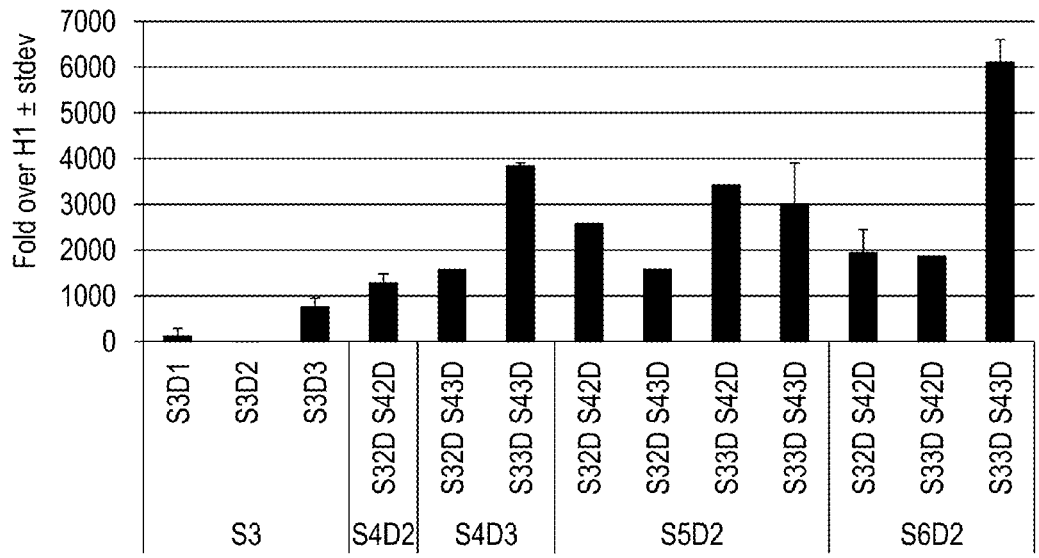
Figure 13B:
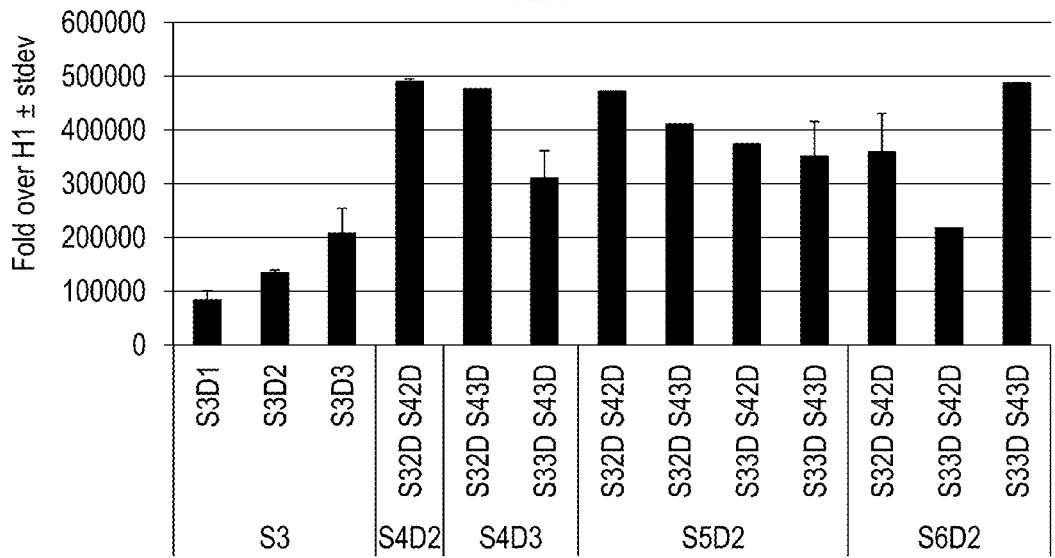
Figure 13C:
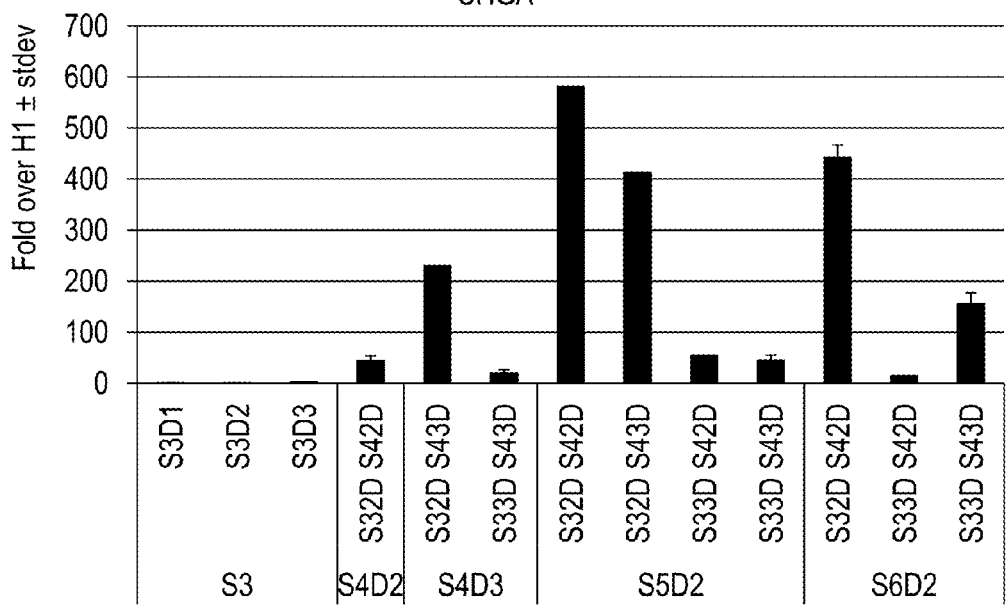
Figure 13D:
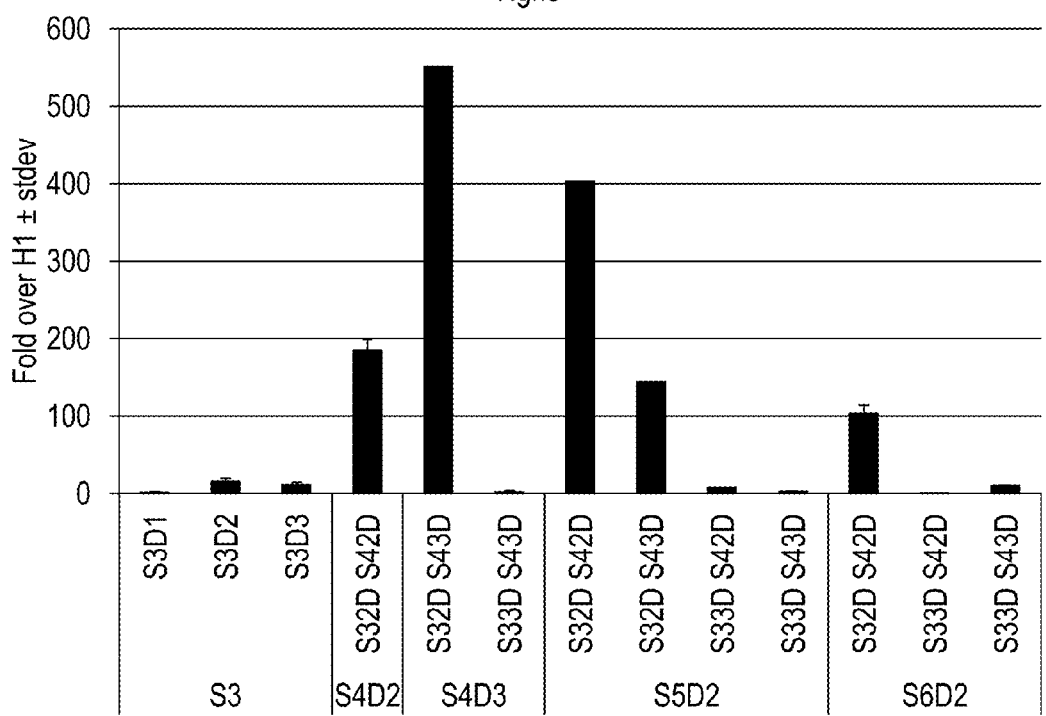
Figure 13F:
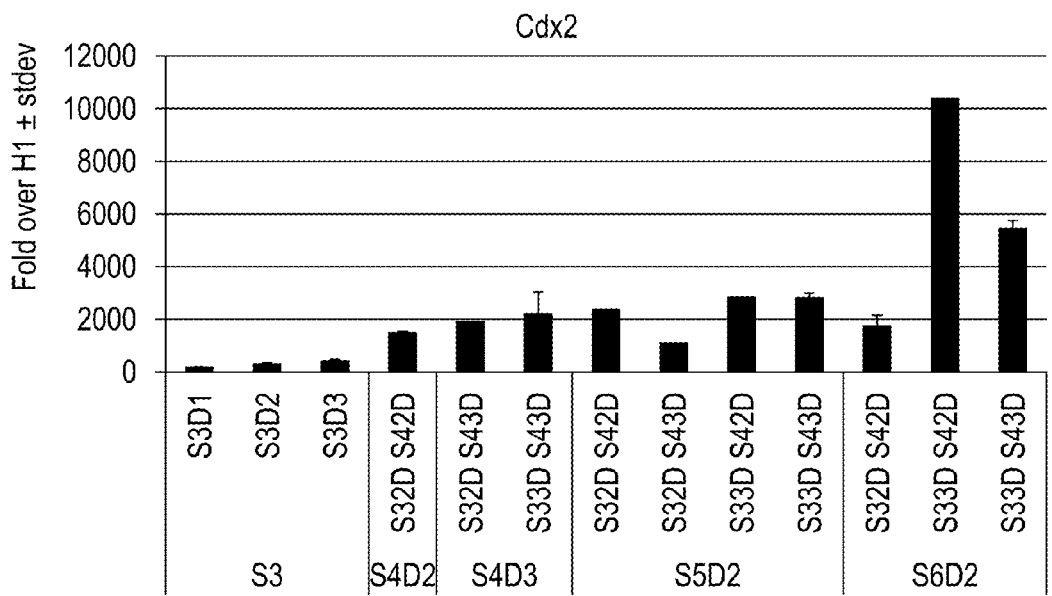
Figure 13G:
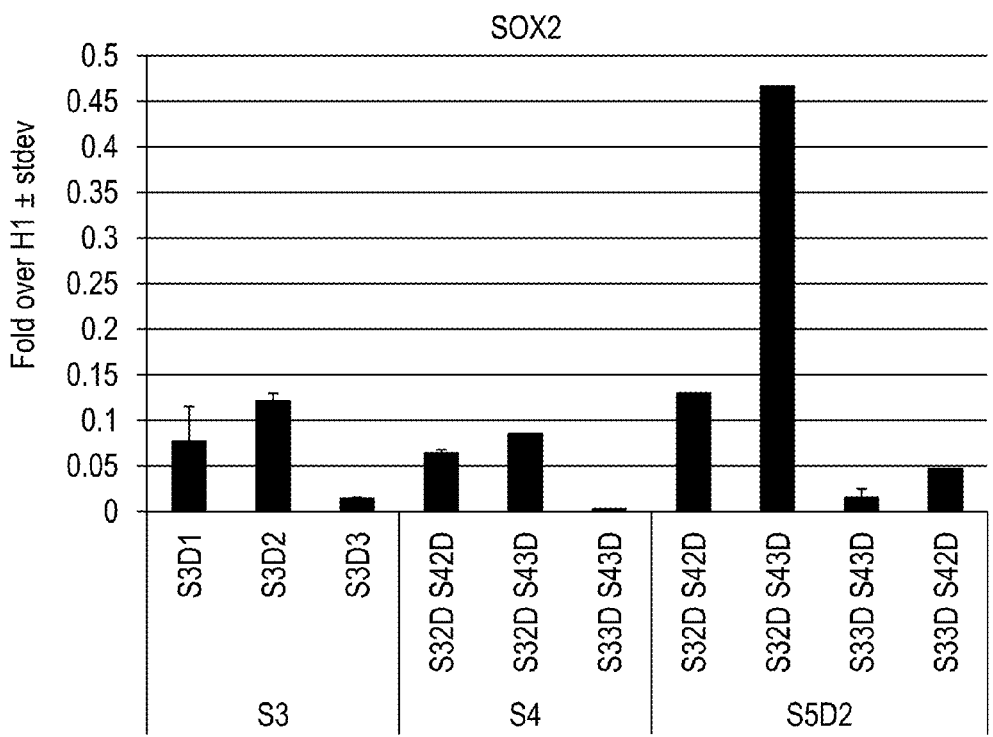

Data from real time PCR analyses of samples harvested at stage 3, stage 4, stage 5, or stage 6 is shown in FIG. 13A to FIG. 13G. This data shows that extending S3 and S4 to three days enhances expression of NKX6.1, when compared with cultures having a two day S3 and S4 (FIG. 13A). Cells treated for three days at stage 3 show down-regulation of the expression of pro-endocrine markers when compared to cultures where duration of S3 and S4 were only two days (FIG. 13D and FIG. 13E). Furthermore, prolonging stage 4 to three days did significantly enhance expression of SOX2 (FIG. 13G).

The data obtained in this Example is consistent with data generated in the previous examples in showing that prolonged BMP inhibition biases the foregut towards a population high in SOX2. Based on the data from this example and the previous examples, one may conclude that the optimal duration of stage 3 and stage 4 is two days. The ideal protocol will result in differentiated cells with high levels of expression of pro-endocrine markers, high NKX6.1, low CDX2 and low SOX2 expression.

Example 9

Prolonged Exposure to BMP Inhibition in the Presence of High Glucose and B27 Supplement Significantly Increases SOX2 Expression at S3 and S4

This protocol was performed to determine the factors that affect SOX2 expression at S3 and S4 during the stepwise differentiation of pluripotent cells into hormone producing cells.

Cells of the human embryonic stem cells line H1 were cultured on MATRIGEL™ (1:30 dilution)-coated dishes and cultured in mTesr™1 media until ~70% confluence and differentiated as follows:

a. Undifferentiated cells were cultured in RPMI medium (Invitrogen) supplemented with 0.2% FBS; 100 ng/ml activin A; 20 ng/ml WNT-3a for one day. Cells were then treated with RPMI medium supplemented with 0.5% FBS; 100 ng/ml activin A for an additional two days (Stage 1).

b. Stage 1 cells were treated with DMEM/F12 medium supplemented with 2% FBS; 50 ng/ml FGF7 for three days (Stage 2).

c. Stage 2 cells were cultured in DMEM-High glucose medium supplemented with 1% B27; 0.25 µM SANT-1; 2 µM RA; 100 ng/ml Noggin (R & D systems, MN, USA) for four days (Stage 3).

d. Stage 3 cells were treated with DMEM-High glucose medium supplemented with 1% B27; 100 ng/ml Noggin; 1 µM ALK5 inhibitor II (Axxora, Calif., USA); and 50 nM TPB for four days (Stage 4).

Figure 14A:
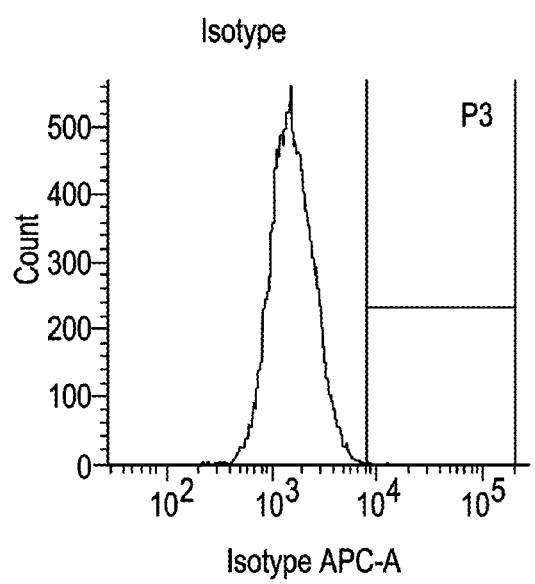
FIG. 14A to FIG. 14H show FACS histogram expression profiles of the following markers at S3 day 4 of cells differentiated according to Example 9.
Figure 14B:
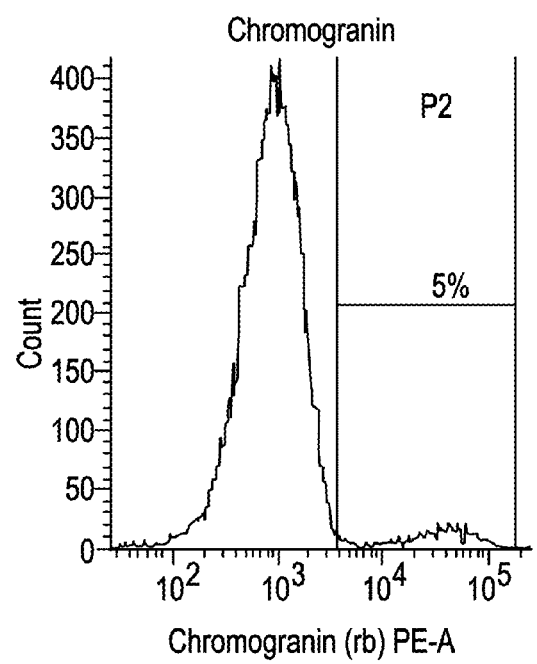
Figure 14C:
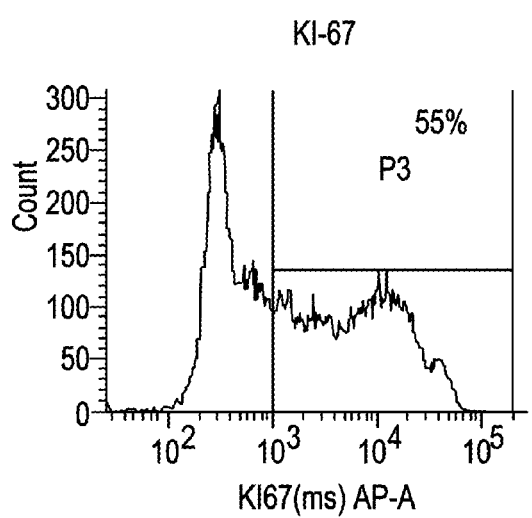
Figure 14D:
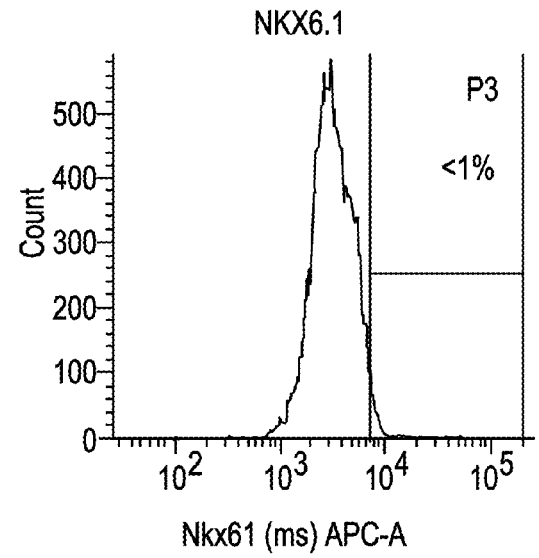
Figure 14E:
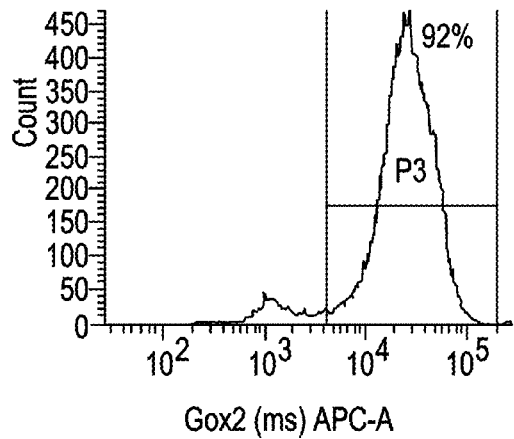
Figure 14F:
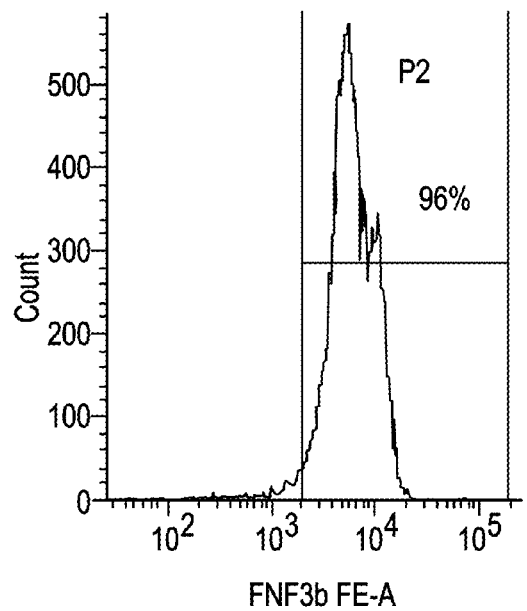
Figure 14G:
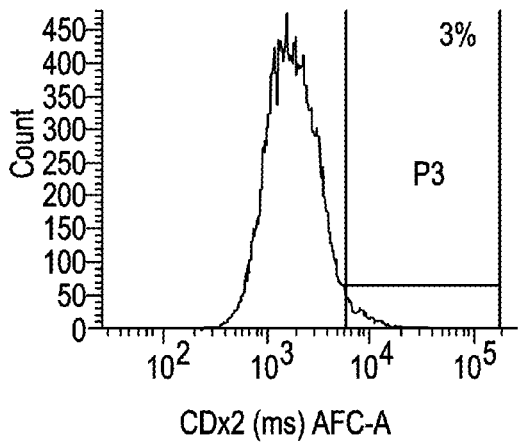
Figure 14H:
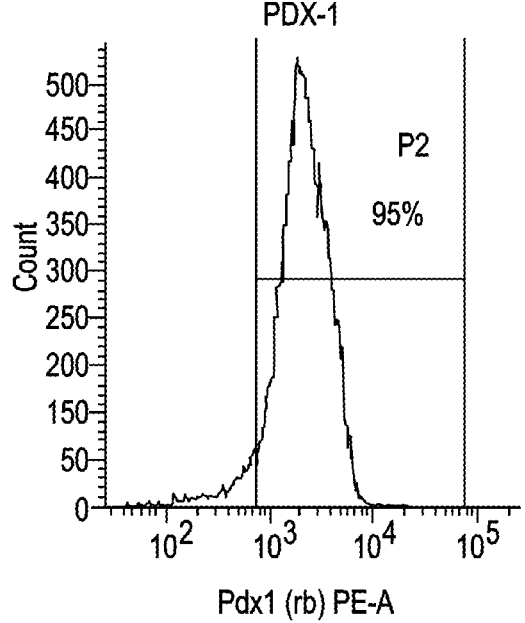

FIG. 14A to FIG. 14H depict FACS histograms for cells harvested at stage 3 day 4 obtained for the following markers: Isotype control (FIG. 14A), chromogranin (FIG. 14B), KI-67 (FIG. 14C), NKX6.1 (FIG. 14D), SOX2 (FIG. 14E), HNF3B (FIG. 14F), CDX2 (FIG. 14G), PDX-1 (FIG. 14H). Percentage expression for each marker is shown on each histogram. The majority of the cells at stage 3 were positive for expression of PDX-1 (FIG. 14H), and HNF3B (FIG. 14F), negative for expression of NKX6.1 (FIG. 14D), and showed low expression of chromogranin (FIG. 14B), and CDX2 (FIG. 14G). However, over 90% of the cells were also strongly positive for SOX2 (FIG. 14E). This indicates that at stage 3, the majority of cells were positive for PDX-1 and SOX2 and negative for NKX6.1 suggesting establishment of an endoderm population consistent with a foregut population anterior to the PDX-1 domain of pancreas.

Furthermore, the percentage of cells which were SOX2+ at stage 3, in the population of cells generated using the protocol outlined in this example, was significantly higher than the percentage of cells that were SOX2+ in the population of cells generated using the protocol outlined in Example 1. This difference can be attributed to the prolonged exposure to the BMP antagonist Noggin, lack of FGF7 and PKC activator in the culture medium at stage 3 of this example.

Figure 15A:
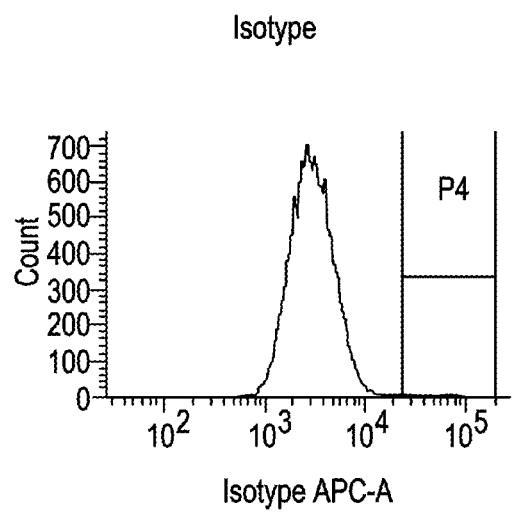
FIG. 15A to FIG. 15G show FACS histogram expression profiles of the following markers at S4 day 2 of cells differentiated according to Example 9.
Figure 15B:
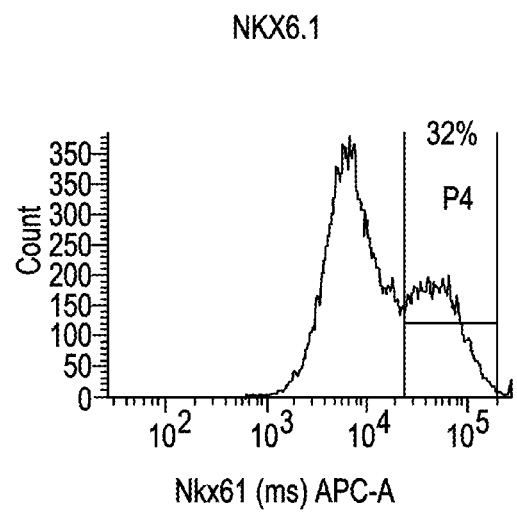
Figure 15C:
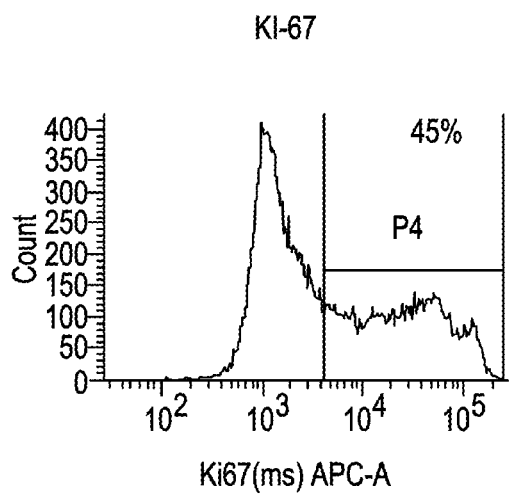
Figure 15D:
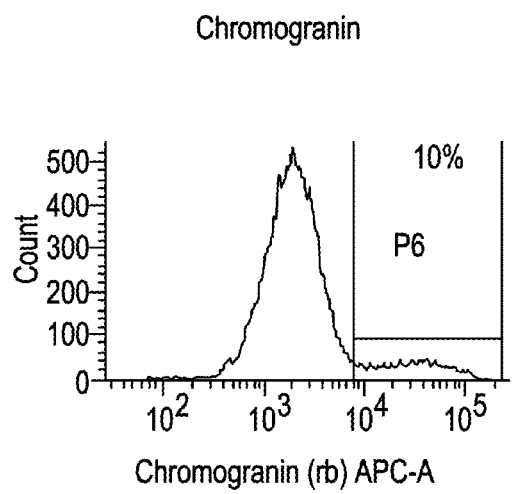
Figure 15E:
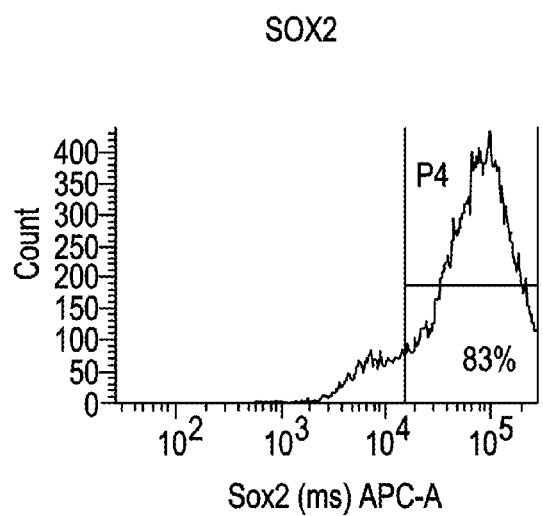
Figure 15F:
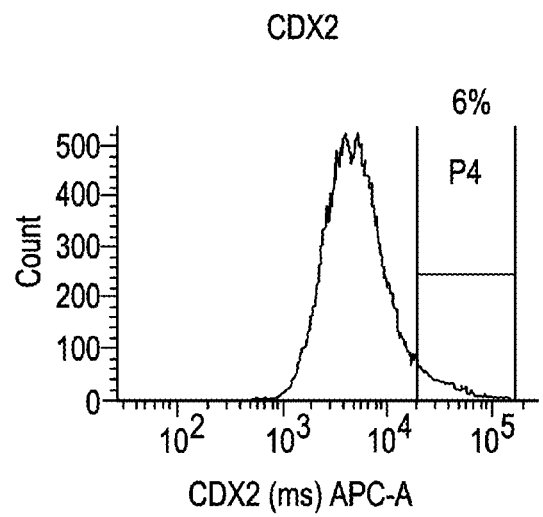
Figure 15G:
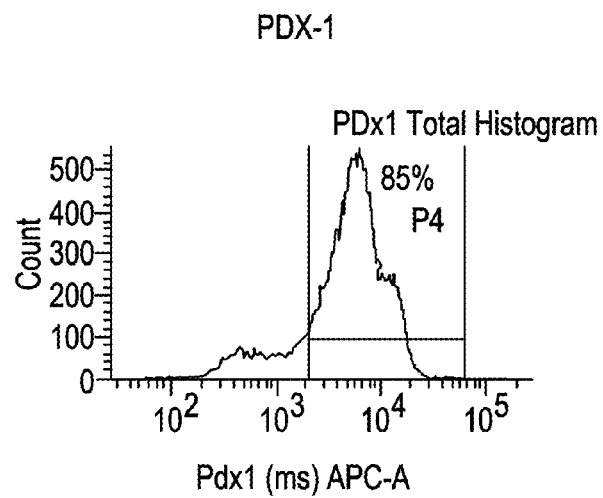

FIG. 15A through FIG. 15G show FACS histogram expression profiles of the following markers at S4 day 2 of cells differentiated according to Example 9: FIG. 15A: Isotype control, FIG. 15B: NKX6.1, FIG. 15C: KI-67, FIG. 15D: chromogranin, FIG. 15E: SOX2, FIG. 15F: CDX2, FIG. 15G: PDX-1. Percentage expression for each marker is shown on each histogram.

Figure 16A:
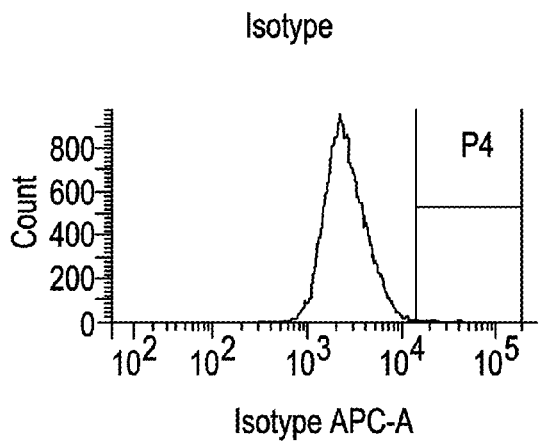
FIG. 16A to FIG. 16F show FACS histogram expression profiles of the following markers at S4 day 4 of cells differentiated according to Example 9.
Figure 16B:
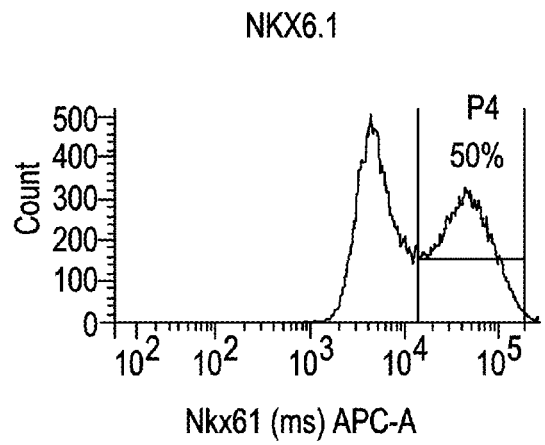
Figure 16C:
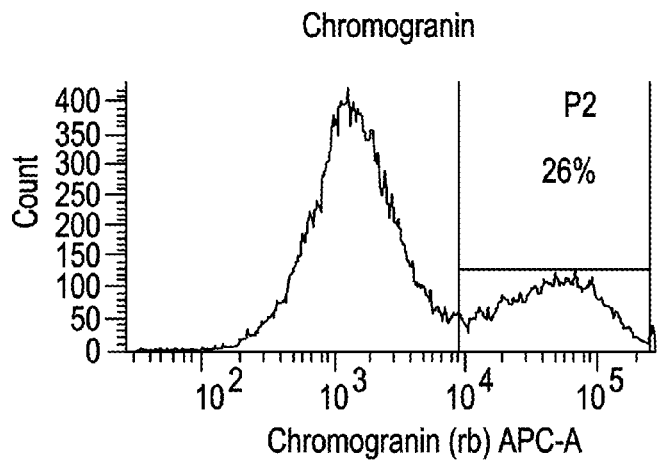
Figure 16D:
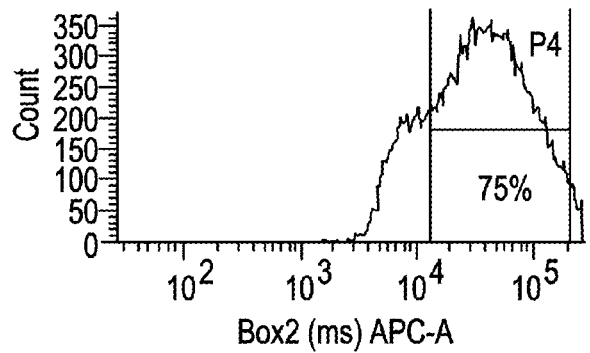
Figure 16E:
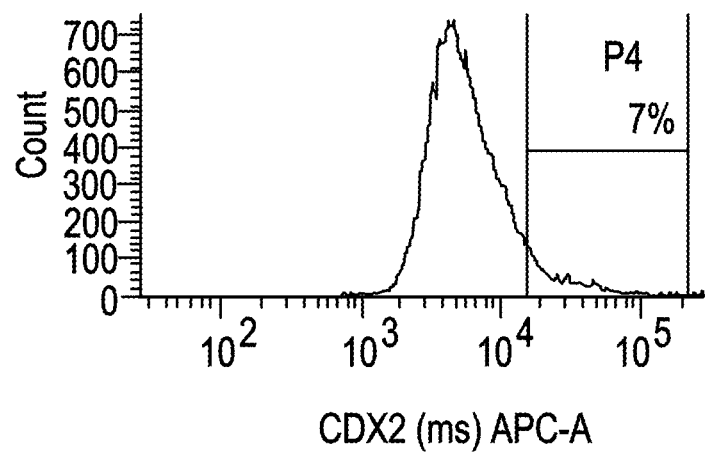
Figure 16F:
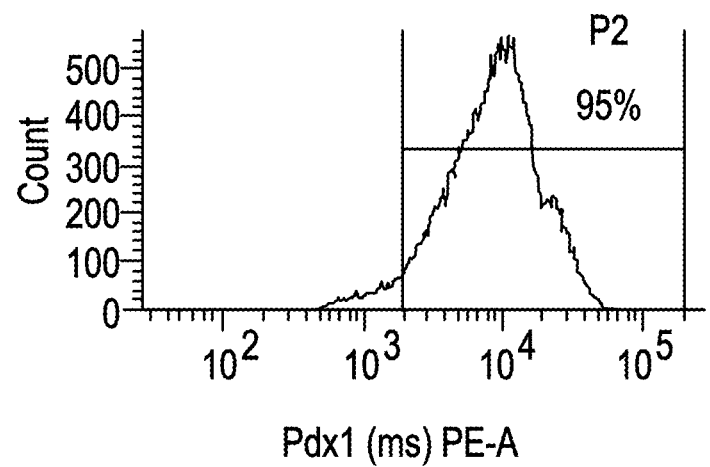

FIG. 16A to FIG. 16F show FACS histogram expression profiles of the following markers at S4 day 4 of cells differentiated according to Example 9. FIG. 16A: Isotype control, FIG. 16B: NKX6.1, FIG. 16C: chromogranin, FIG. 16D: SOX2, FIG. 16E: CDX2, FIG. 16F: PDX-1. Percentage expression for each marker is shown on each histogram.

Table V, below, summarizes the data obtained for the % expression of endoderm markers at S3 and S4 for cells differentiated according to the protocol outlined in this example.

TABLE V

% Expression of Endoderm Markers at S3-S4

| Stage (Days) | Total number of days since start of differentiation | % PDX-1+ | % PDX-1+ SOX2+ | % PDX-1+ NKX6.1+ SOX2- | % PDX-1+ CDX2+ | % PDX-1+ NKX6.1+ SOX2+ |
|---|---|---|---|---|---|---|
| Stage 3 4 days | 10 days | 95 | 92 | <1 | <5 | <1 |
| Stage 4 2 days | 12 days | 85 | 83 | <1 | ~6 | ~30 |
| Stage 4 4 days | 14 days | 95 | 75 | <5 | ~7 | ~50 |

Figure 17A:
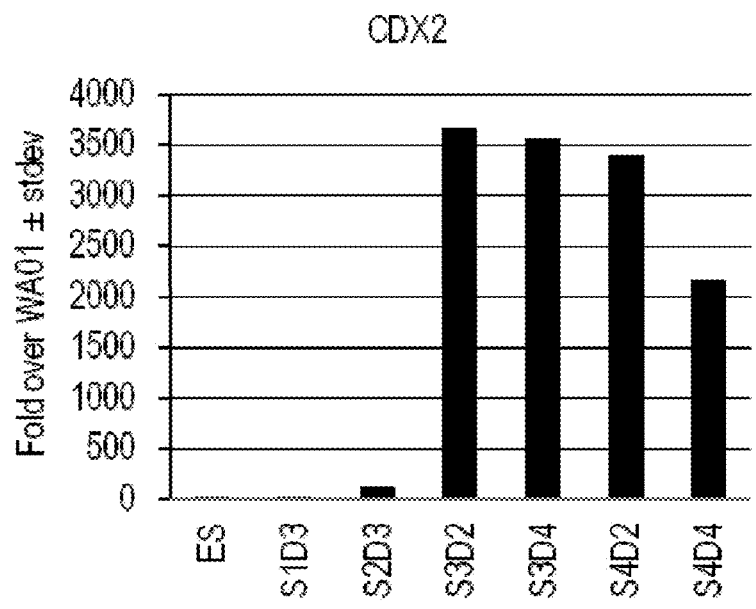
FIG. 17A to FIG. 17J show data from real-time PCR analysis of the expression of the following genes in cells of the human embryonic stem cell line H1 differentiated according to the Example 9 and harvested at S1D3, S2D3, S3D4, S4D2, and S4D4.
Figure 17B:
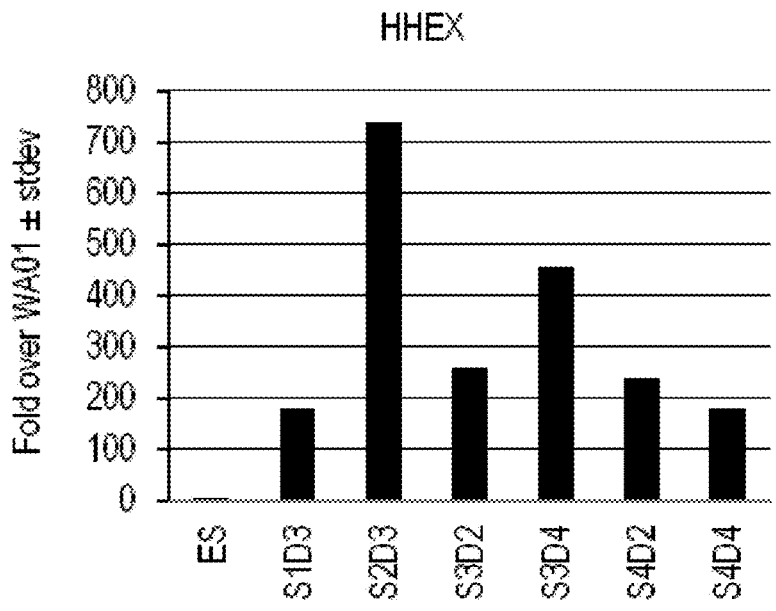
Figure 17C:
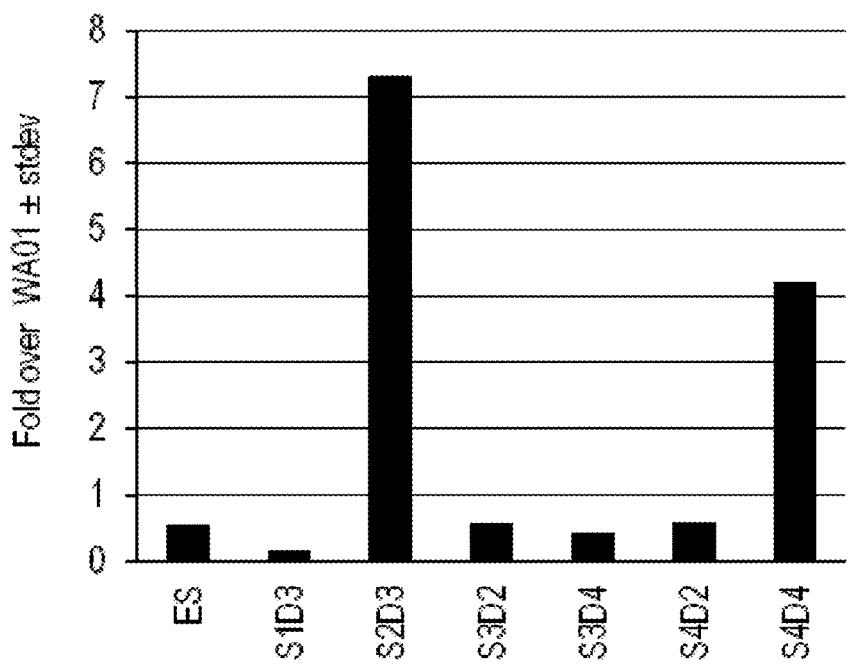
Figure 17D:
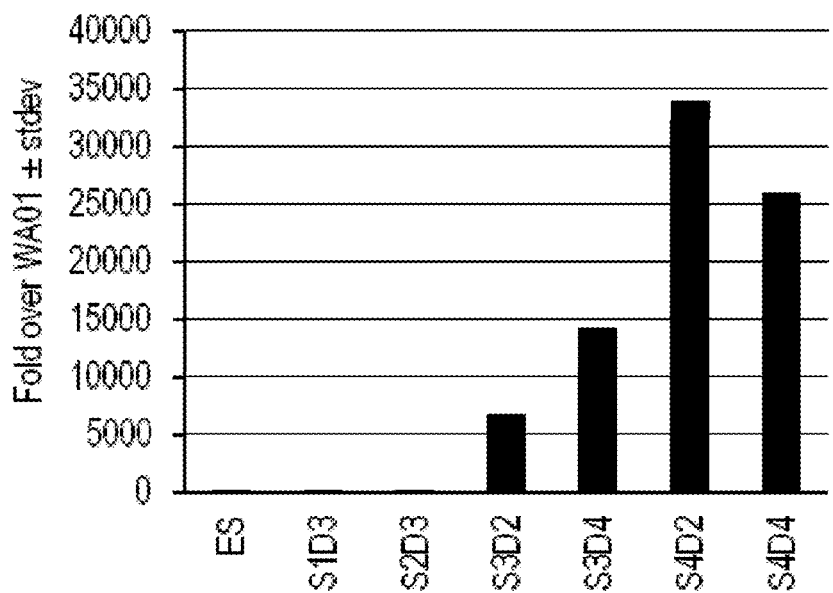
Figure 17E:
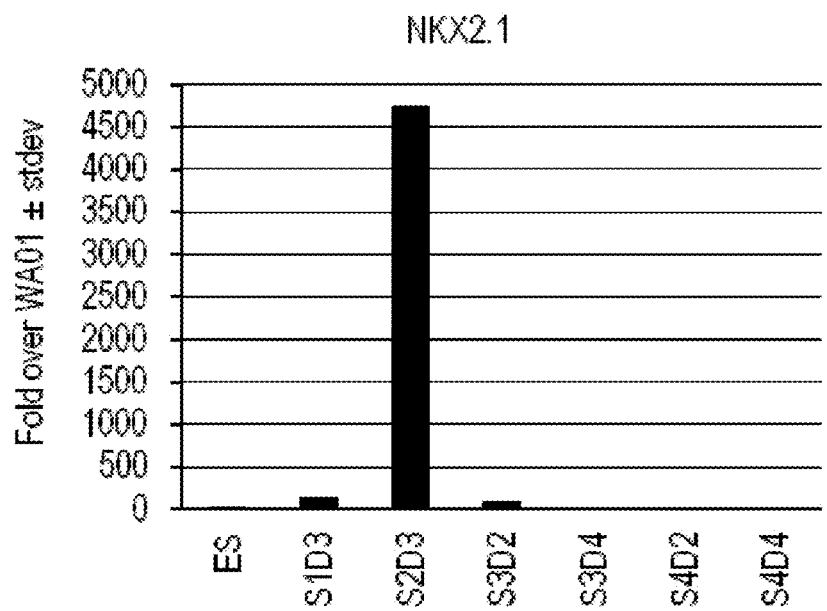
Figure 17F:
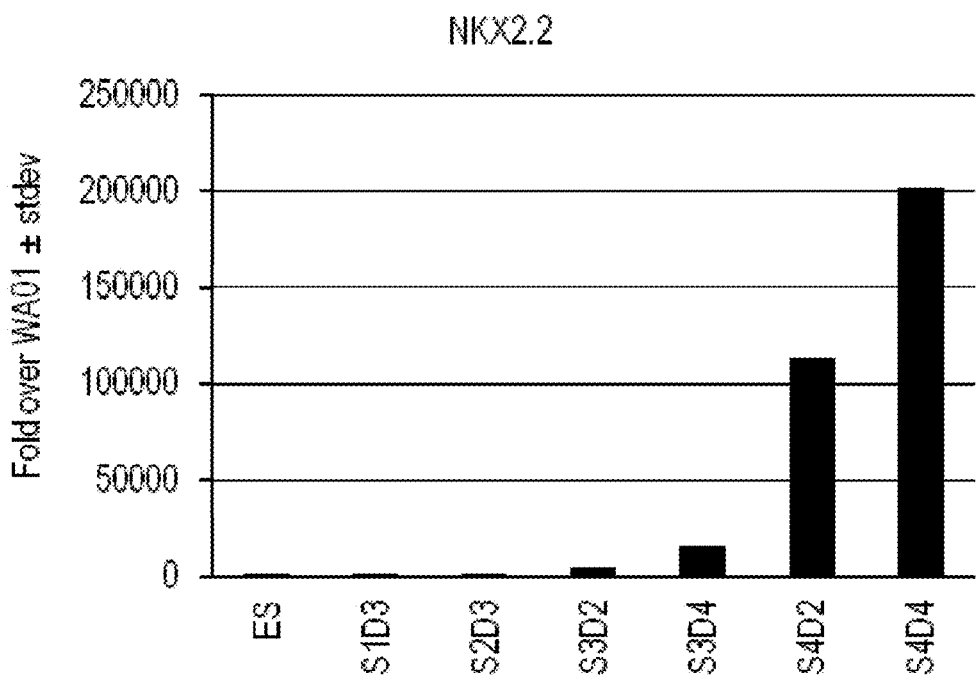
Figure 17G:
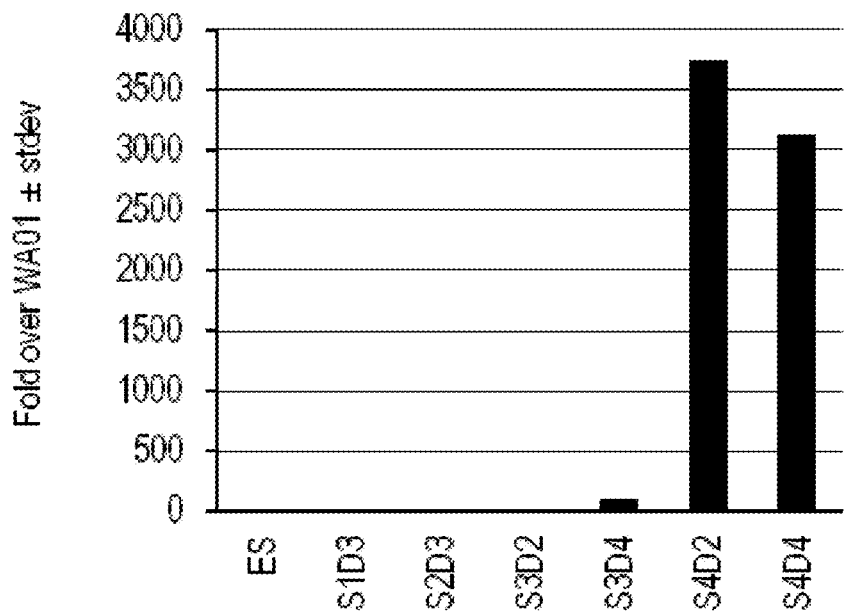
Figure 17H:
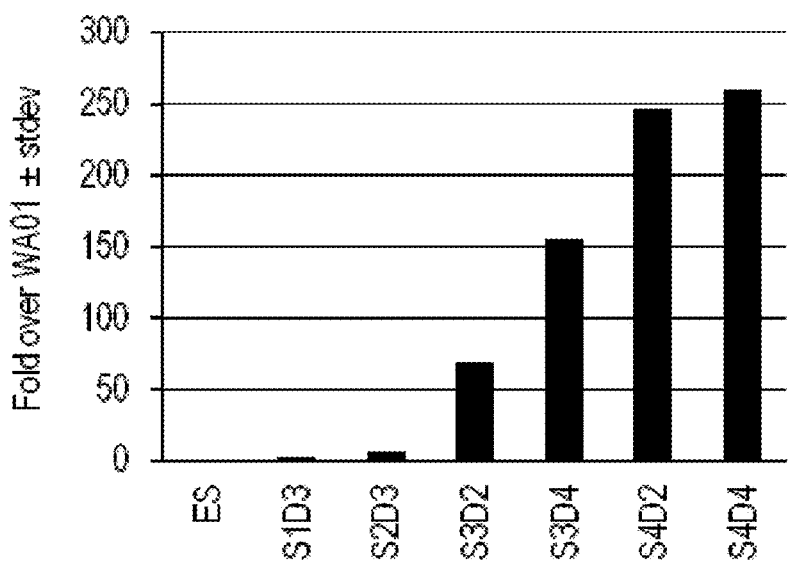
Figure 17I:
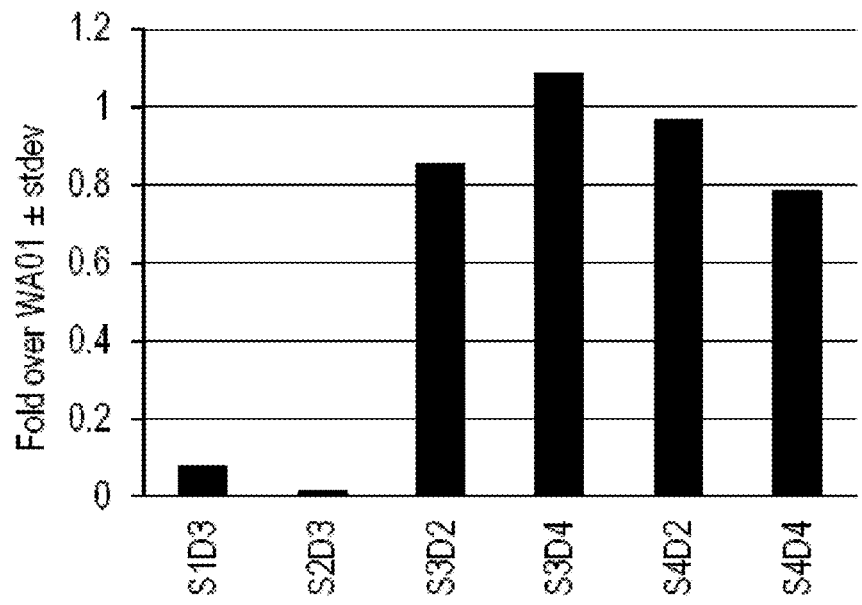
Figure 17J:
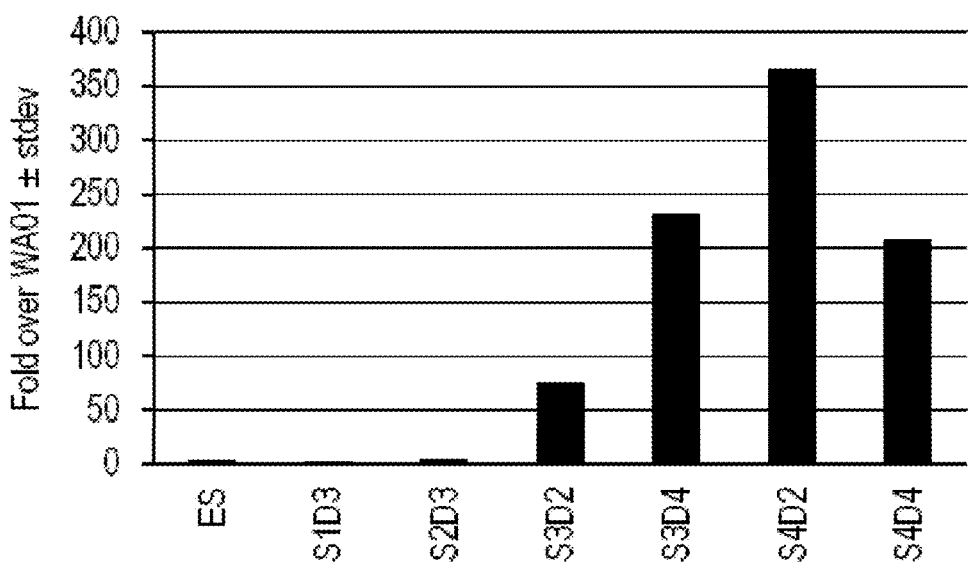

FIG. 17A to FIG. 17J depict the results of real-time PCR analyses of the expression of the following genes in cells of the human embryonic stem cell line H1 differentiated according to the Example 9. FIG. 17A: CDX2, FIG. 17B: HHex, FIG. 17C: FOXE1, FIG. 17D: IPF1 (PDX-1), FIG. 17E: NKX2.1, FIG. 17F: NKX2.2, FIG. 17G: NKX6.1, FIG. 17H: PROX1, FIG. 17I: SOX2, FIG. 17J: SOX9.

As seen in FIGS. 14 to 17 and in Table V, at days 2-4 of stage 4, there was a significant increase in expression of NKX6.1 while maintaining a high expression of PDX-1. Although, expression of SOX2 dropped from stage 3 to stage 4, ~75% of cells were still SOX2+. Same as in FIG. 5, CDX2+ cells, SOX2+ cells, and NKX6.1+ cells were mutually exclusive from chromogranin population. This implies that the population of stage 4 day 4 cells generated using the protocol outlined in Example 9 has ~50% NKX6.1+SOX2+PDX-1+ CDX2-chromogranin negative fraction. This is in contrast to the cell population generated in Example 1 which had 40-70% PDX-1+NKX6.1+SOX2-, CDX2-, chromogranin negative fraction and 2-25% PDX-1+NKX6.1+SOX2+ at S4-S5. Clearly, cells generated using the protocol in Example 1 had far higher percentage of pancreatic endoderm, as defined as a population that is PDX-1+ and NXK6.1+ while being low or negative for SOX2 and CDX2, as compared to cells generated in Example 9.

The data obtained in this Example provides support that prolonged exposure to BMP inhibition in the presence of high glucose and B27 supplement significantly increases expression of SOX2 at stages 3 and 4 of differentiation.

Example 10

Previously Published Protocol Results in Formation of Significant Number of SOX2+ Population at the Stages 3-4

Kroon et al. have published a protocol for preparing cells of the pancreatic endoderm lineage from human embryonic stem cells (Nature Biotech 2008, 26: 443-452; hereinafter "Kroon"). In the Example provided here, human embryonic stem cells were differentiated following the Kroon protocol and assayed for expression of markers characteristic of the different stages of differentiation.

Cells of the human embryonic stem cells line H1 were plated on MATRIGEL™ (1:30 dilution)-coated dishes and cultured in mTesr™1 media until ~70% confluence and differentiated using the protocol previously published by Kroon as follows:

a) Undifferentiated cells were exposed to RPMI medium supplemented with 0.2% FBS, 100 ng/ml activin A, 20 ng/ml WNT-3a for one day followed by treatment with RPMI medium supplemented with 0.5% FBS, 100 ng/ml activin A for an additional two days (Stage 1).

b) Stage 1 cells were exposed to RPMI medium supplemented with 2% FBS, 50 ng/ml FGF7 for three days (Stage 2).

c) Stage 2 cells were treated with DMEM-High glucose medium supplemented with 1% B27, 0.25 µM SANT-1, 2 µM RA, 50 ng/ml of Noggin (R & D systems, MN) for three days (Stage 3).

d) Stage 3 cells were cultured in DMEM-High glucose medium supplemented with 1% B27 for three days (Stage 4).

e) Stage 4 cells were scraped from the wells and resuspended as clusters in DMEM-High glucose medium supplemented with 1% B27 for two days.

Figure 18A:
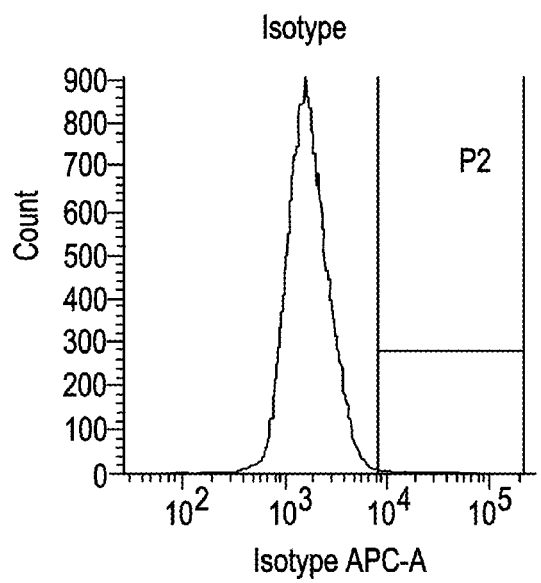
FIG. 18A to FIG. 18G show FACS histogram expression profiles of the following markers at S3 day 3 of cells differentiated according to Example 10.
Figure 18B:
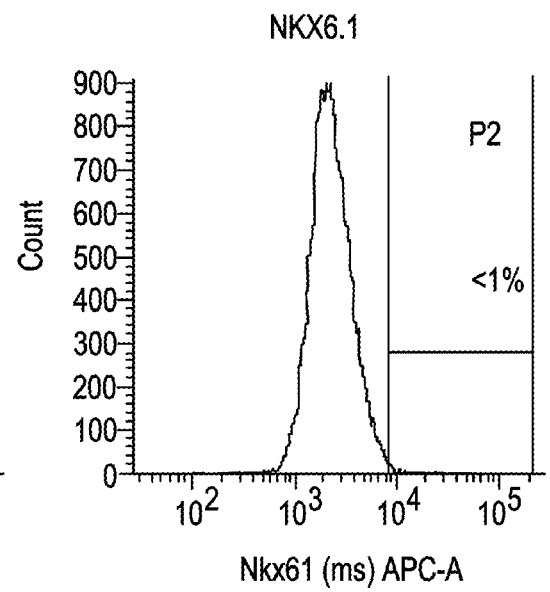
Figure 18C:
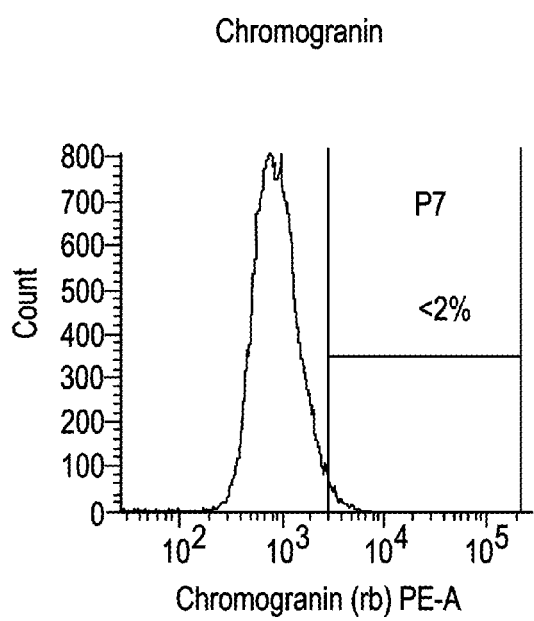
Figure 18D:
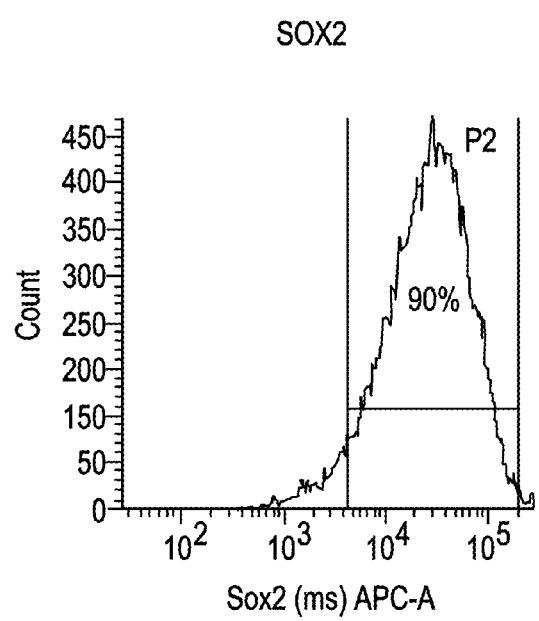
Figure 18E:
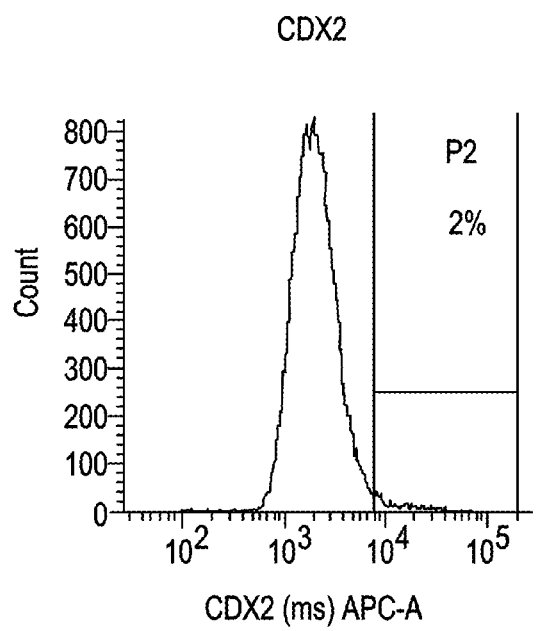
Figure 18F:
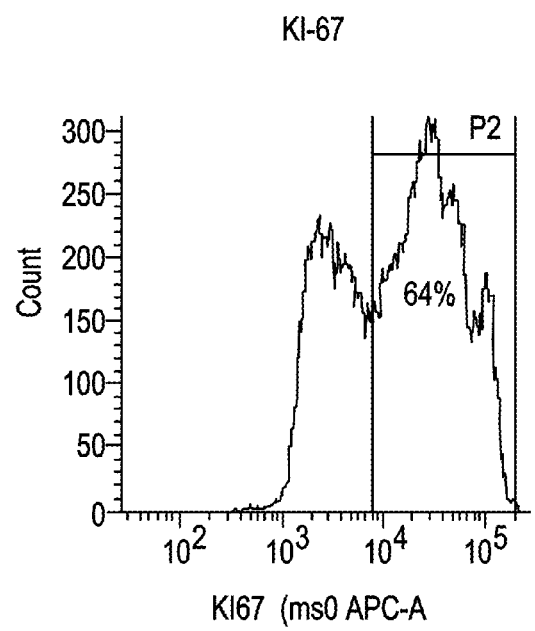
Figure 18G:
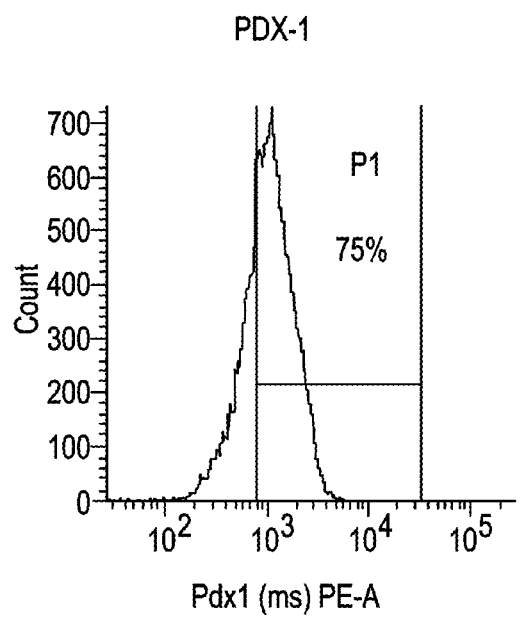

FIG. 18A to FIG. 18G show FACS histogram expression profiles of the following markers at S3 day 3 of cells differentiated according to Example 10: Isotype control (FIG. 18A), NKX6.1 (FIG. 18B), chromogranin (FIG. 18C), SOX2 (FIG. 18D), CDX2 (FIG. 18E), KI-67 (FIG. 18F), PDX-1 (FIG. 18G). Percentage expression for each marker is shown on each histogram.

Figure 19A:
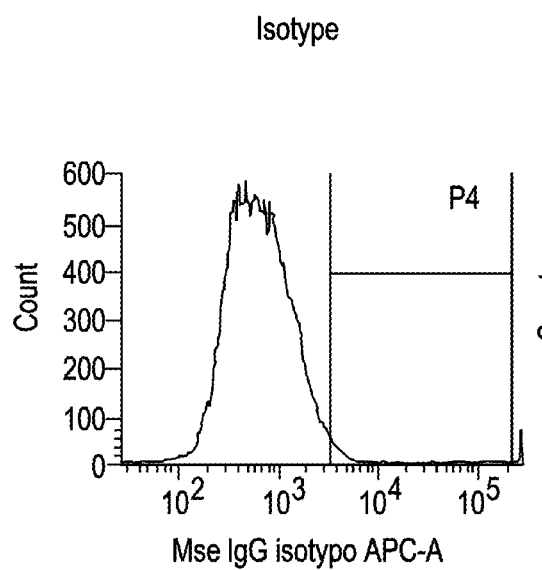
FIG. 19A to FIG. 19G show FACS histogram expression profiles of the following markers at S4 day 5 of cells differentiated according to Example 10.
Figure 19B:
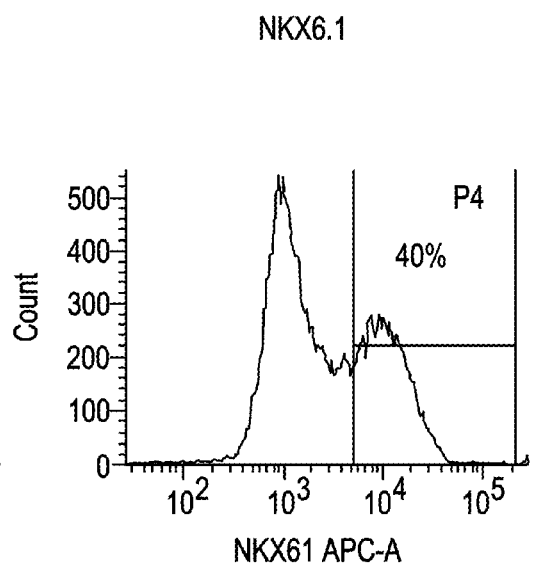
Figure 19C:
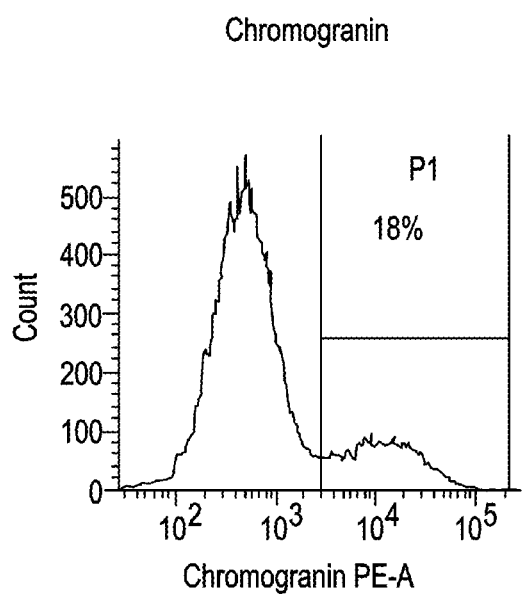
Figure 19D:
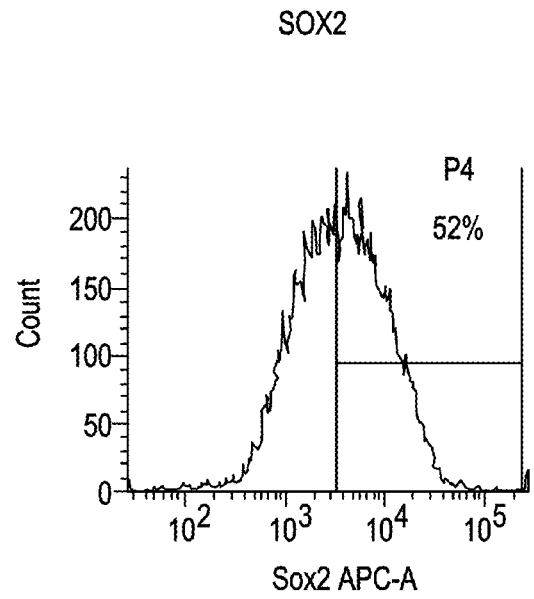
Figure 19E:
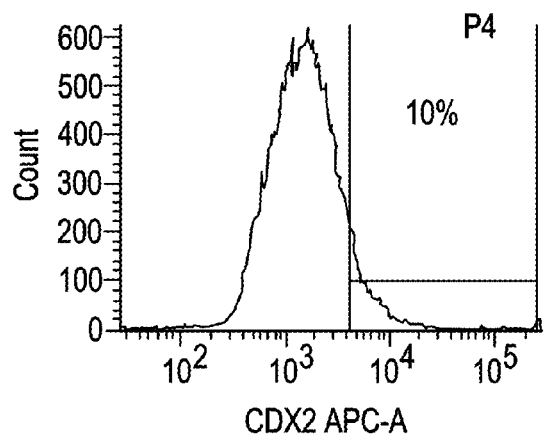
Figure 19F:
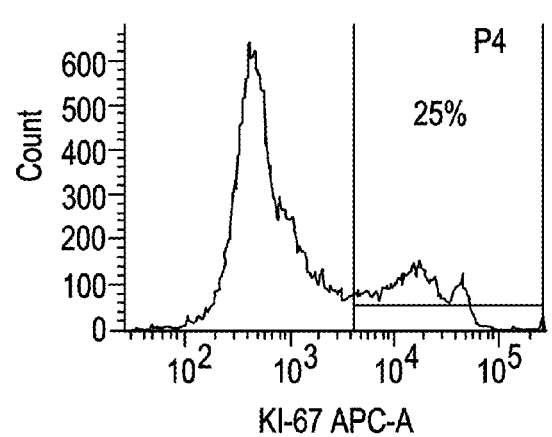
Figure 19G:
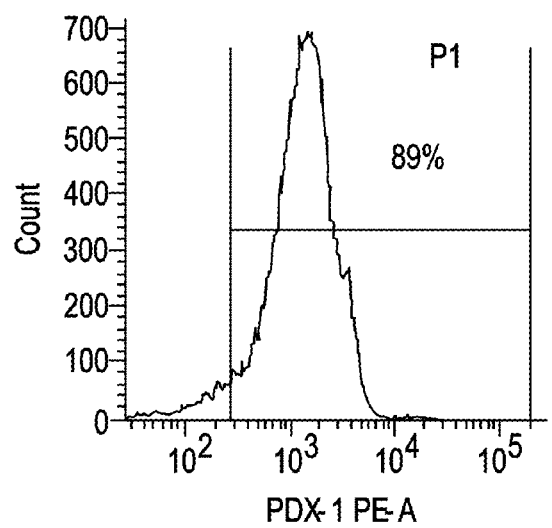

FIG. 19A to FIG. 19G show FACS histogram expression profiles of the following markers at S4 day 5 of cells differentiated according to Example 10. Isotype control (FIG. 19A), NKX6.1 (FIG. 19B), chromogranin (FIG. 19C), SOX2 (FIG. 19D), CDX2 (FIG. 19E), KI-67 (FIG. 19F), PDX-1 (FIG. 19G). Percentage expression for each marker is shown on each histogram As shown in FIGS. 18 and 19, by the end of stage 4 (day 5) the clusters of cells in suspension were ~20% NKX6.1+PDX-1+SOX2- and ~20% PDX-1+NKX6.1+SOX2+. These results indicate that a significant fraction of the population of cells at stage 4 generated according to Example 10 that were NKX6.1+ were also SOX2+.

Table VI, shown below, summarizes the percentages of endoderm markers at S3-S4 of cells generated in this example.

TABLE VI

Expression of Endoderm Markers at S3-S4 in Cells Differentiated According to Kroon

| Stage (days) | Total number of days since start of differentiation | % PDX-1+ | % PDX-1+ SOX2+ | % PDX-1+ NKX6.1+ SOX2− | % PDX-1+ CDX2+ | % PDX-1+ NKX6.1+ SOX2+ |
|---|---|---|---|---|---|---|
| Stage 3 3 days | 9 days | 75 | 75 | <1 | <2 | <1 |
| Stage 4 5 days* | 14 days | 89 | 52 | ~20 | ~10 | ~20 |

*Last two days in suspension culture.

Example 11

Addition of Ascorbic Acid Results in Significant Decrease in the Number of Polyhormonal Cells and a Concomitant Increase in the Number of Single Hormonal Insulin Positive Cells The effect of ascorbic acid on the expression of markers during differentiation of pluripotent cells to hormone producing cells was tested. Cells were cultured in medium supplemented with glucose at every step of differentiation and supplemented with ascorbic acid at the formation of stages 3, 4, and 5 as follows:

Cells of the human embryonic stem cell line H1 at various passages (passage 40 to passage 52) were seeded as single cells at a density of 100,000 cells/cm$^2$ on MATRIGEL™ (1:30 dilution) coated dishes in mTesr™1 media and 10 μM of Y27632. Forty eight hours post seeding, cultures were differentiated into pancreatic endocrine lineage as follows:

a. Stage 1 (Definitive Endoderm (DE)—3 days): Prior to start of DE, the cultures were washed and incubated with incomplete PBS (no Mg or Ca) for 30 seconds followed by addition of the stage 1 media. Human embryonic stem cells cultured as single cells on MATRIGEL™-coated dishes were treated with MCDB-131 medium supplemented with 0.1% fatty acid-free BSA, 0.0012 g/ml sodium bicarbonate, 1× GlutaMax™, 5 mM D-Glucose, 100 ng/ml GDF8, and 1 μM MCX compound (GSK3B inhibitor) for one day. Cells were then treated with MCDB-131 medium supplemented with 0.1% fatty acid-free BSA, 0.0012 g/ml sodium bicarbonate, 1× GlutaMax™, 5 mM glucose, 100 ng/ml GDF8, and 100 nM MCX compound for day two, followed by an additional day in MCDB-131 medium supplemented with 0.1% fatty acid-free BSA, 0.0012 g/ml sodium bicarbonate, 1× GlutaMax™, 5 mM Glucose, and 100 ng/ml GDF8.

b. Stage 2 (Primitive gut tube—2 days): Stage 1 cells were treated with MCDB-131 medium supplemented with 0.1% fatty acid-free BSA, 0.0012 g/ml sodium bicarbonate, 1× GlutaMax™, 5 mM D-Glucose, and 25 ng/ml FGF7 for two days.

c. Stage 3 (Foregut—2 days): Stage 2 cells were treated with MCDB-131 medium supplemented with 1:200 dilution of ITS-X, 2.5 mM Glucose, 1× GlutaMax™, 0.0015 g/ml sodium bicarbonate, 2% fatty acid-free BSA, 10 ng/ml Activin A, 25 ng/ml FGF7, 0.25 μM SANT-1, 1 μM RA, 200 nM TPB (PKC activator), 100 nM LDN-193189 (BMP receptor inhibitor) for one day. Cells were then treated with MCDB-131 medium supplemented with 1:200 dilution of ITS-X, 2.5 mM Glucose, 1× GlutaMax™, 0.0015 g/ml sodium bicarbonate, 2% fatty acid-free BSA, 10 ng/ml Activin A, 25 ng/ml FGF7, 0.25 μM SANT-1, 1 μM RA, 200 nM TPB (PKC activator), 10 nM LDN-193189 for an additional day. Some cultures were treated with 0.25 mM ascorbic acid (Catalog# A4544, Sigma, Mo., USA) for the duration of stage 3.

d. Stage 4 (Pancreatic foregut precursor—2 days): Stage 3 cells were treated with MCDB-131 medium supplemented with 1:200 dilution of ITS-X, 2.5 mM Glucose, 1× GlutaMax™, 0.0015 g/ml sodium bicarbonate, 2% fatty acid-free BSA, 0.25 μM SANT-1, 50 nM RA, 200 nM TPB, 50 nM LDN-193189, with or without 0.25 mM ascorbic acid for two days.

e. Stage 5 (Pancreatic endoderm, 2-7 days): Stage 4 cells were treated with MCDB-131 medium supplemented with a 1:200 dilution of ITS-X, 2.5 mM Glucose, 1× GlutaMax™, 0.0015 g/ml sodium bicarbonate, 2% fatty acid-free BSA, 0.25 μM SANT-1, 50 nM RA, with or without 0.25 mM ascorbic acid for 2-7 days.

Figure 20A:
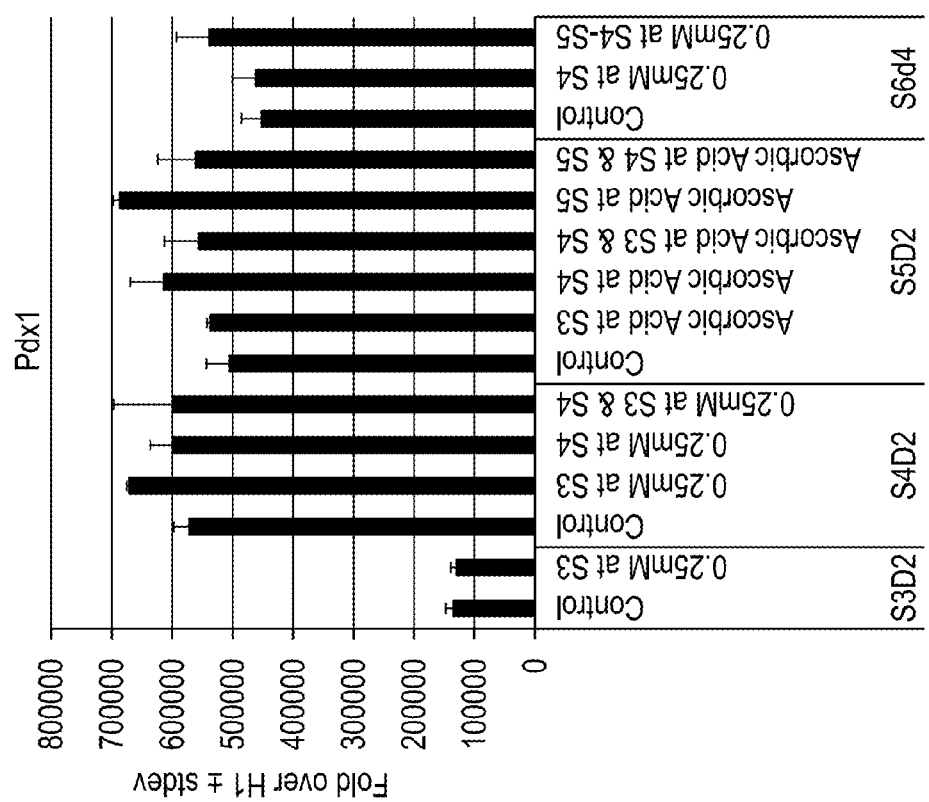
Figure 20B:
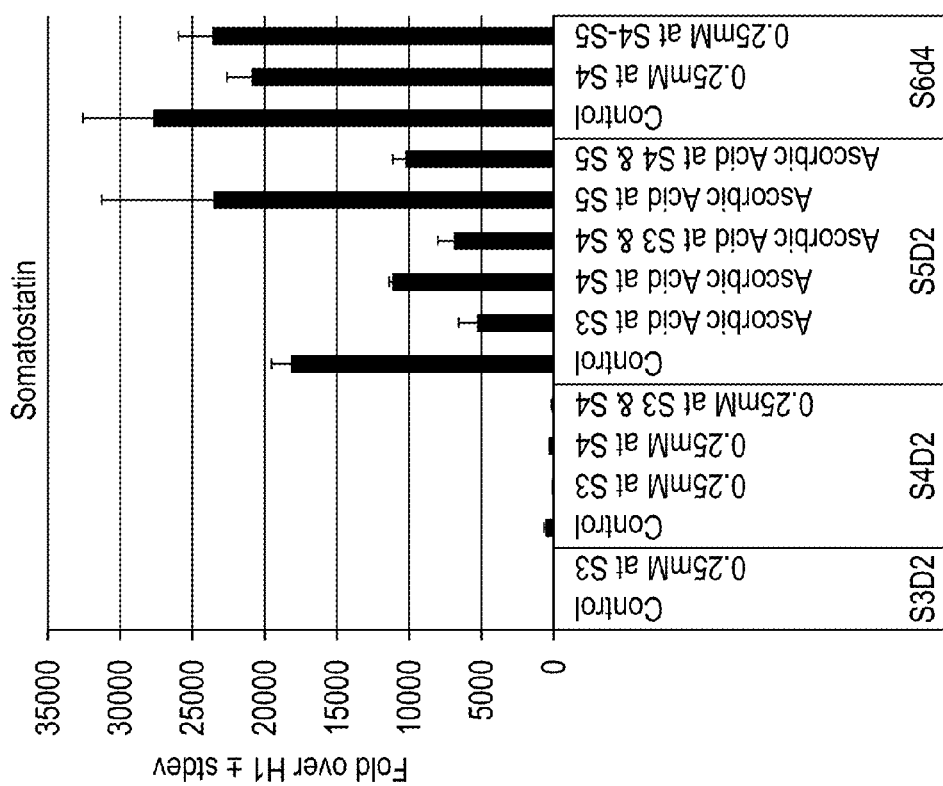
Figure 20C:
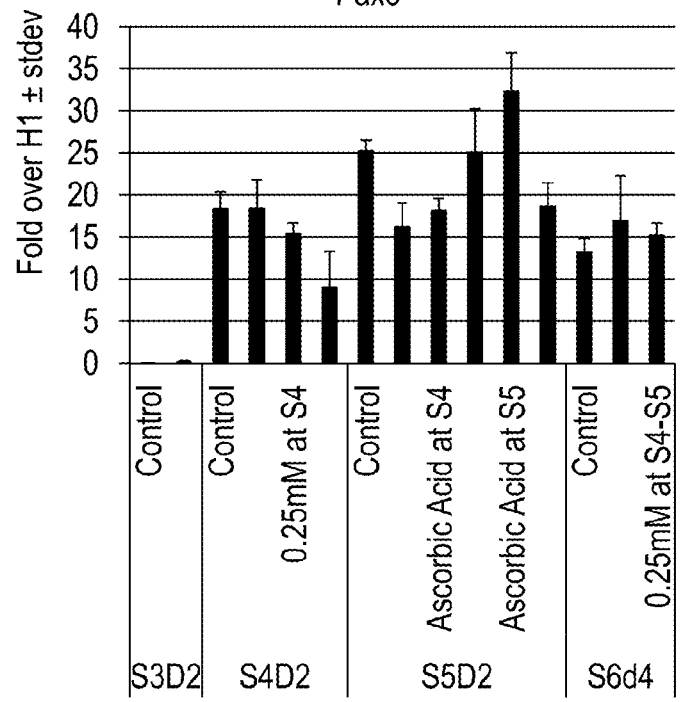
Figure 20D:
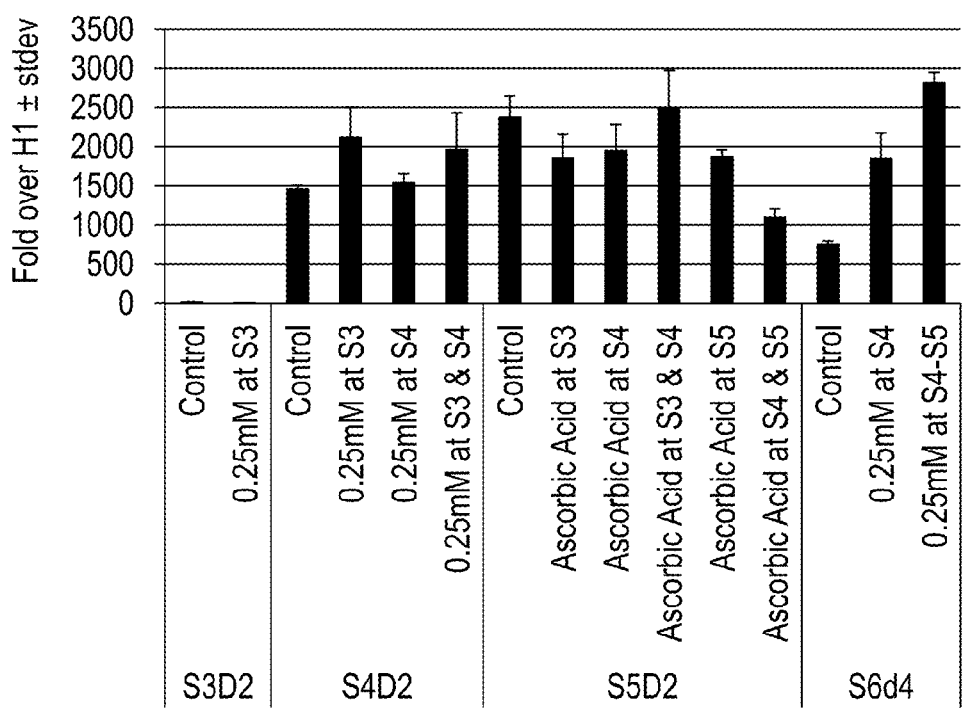
Figure 20H:
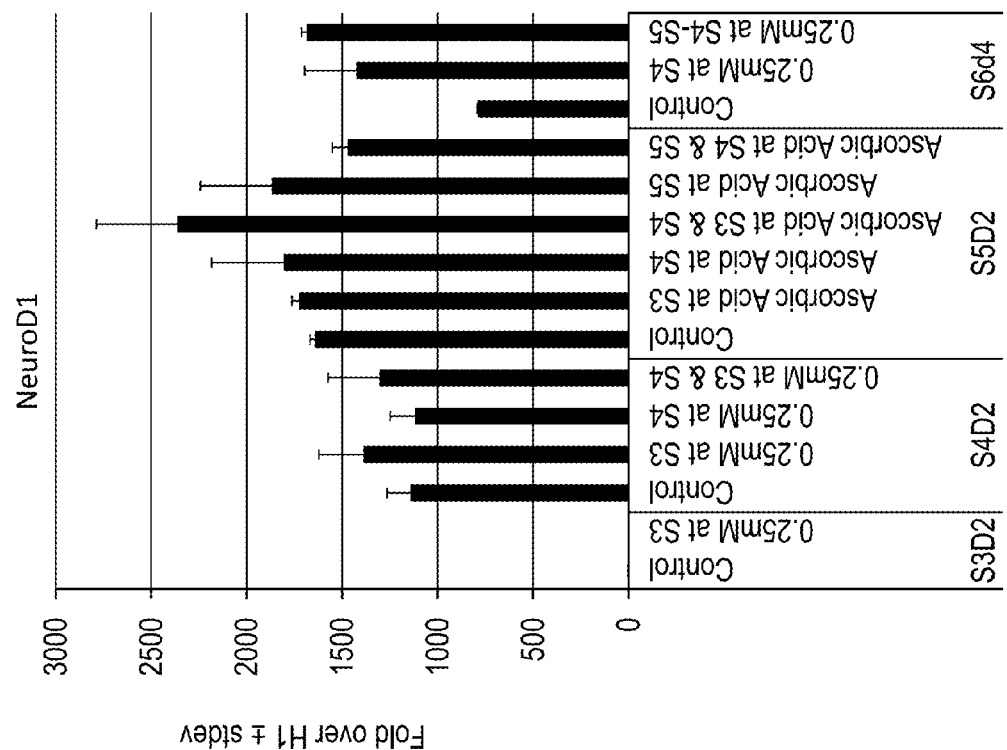
Figure 20G:
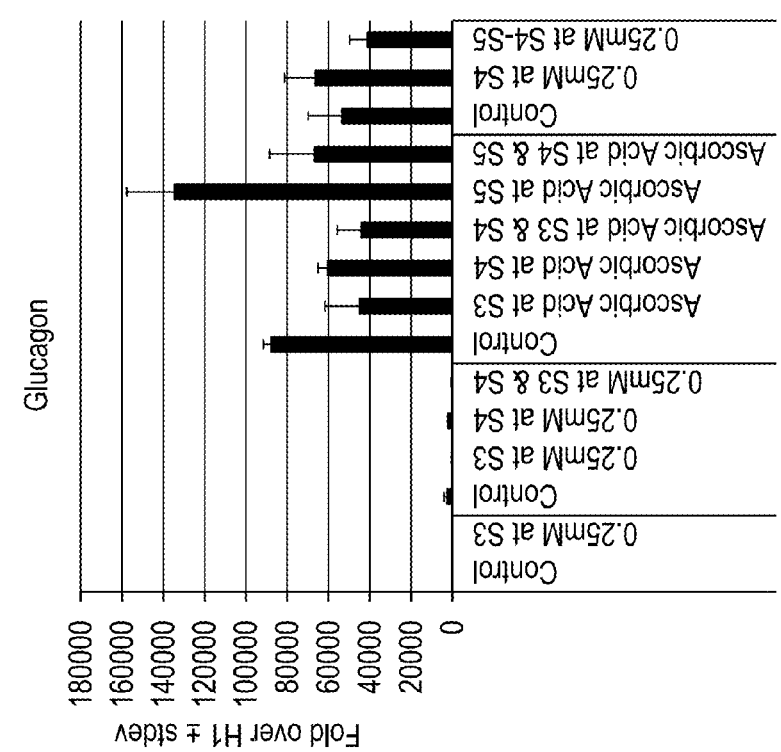
Figures 20I, 20J:
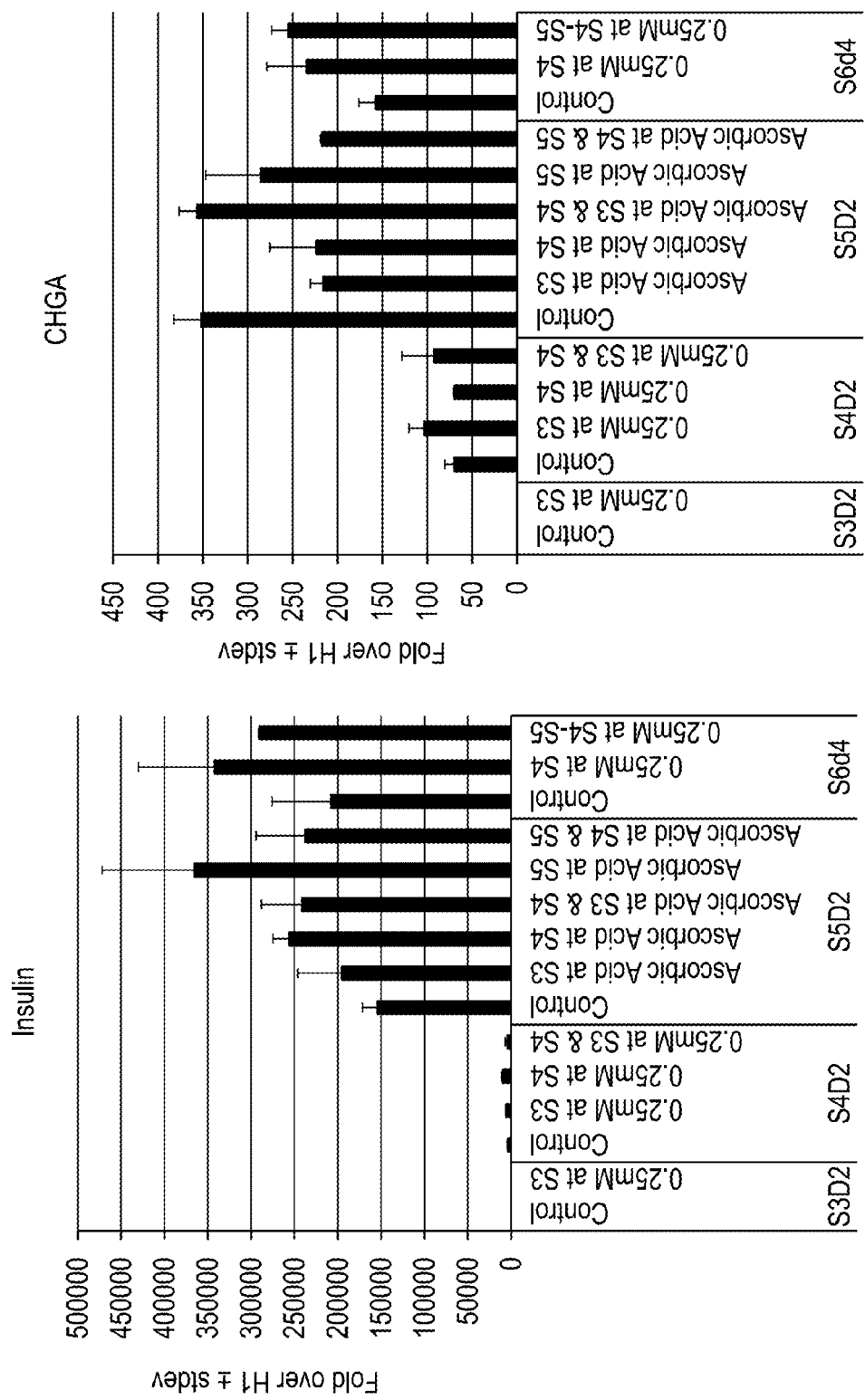

FIG. 20A to FIG. 20J depict real-time PCR analyses of the expression of the following genes in cells of the human embryonic stem cell line H1 differentiated according to the Example 11. FIG. 20A: somatostatin, FIG. 20B: PDX1, FIG. 20C: Pax6, FIG. 20D: Pax4, FIG. 20E: NKX6.1, FIG. 20F: NGN3, FIG. 20G: glucagon, FIG. 20H: NeuroD, FIG. 20I: insulin, FIG. 20J: chromogranin. This Figure shows that addition of ascorbic acid at stage 3 or at stages 3 and 4 significantly decreased expression of somatostatin and glucagon at stages 4-5 while increasing expression of insulin (see FIG. 20A, FIG. 20G, and FIG. 20I). Furthermore, at stages 4-5 expression of pancreatic endoderm markers, such as PDX-1 and NKX6.1 was not significantly altered by addition of 0.25 mM ascorbic acid (see FIG. 20B and FIG. 20D). At stages 4-5, Pax6 expression was down regulated and Pax4 expression was maintained (see FIG. 20C and FIG. 20D). At end of stage 5, cultures treated +/−ascorbic acid at S3-S5 were immune stained for insulin, glucagon, and somatostatin hormones. Table VII summarizes average percentage of insulin positive cells, glucagon and somatostatin positive cells, and polyhormonal cells (two more hormone expression in one cell).

TABLE VII

Expression of hormones as a percentage of the entire hormone count

| Treatment | % single hormonal Insulin+ | % glucagon + plus % somatostatin+ | % Polyhormonal |
|---|---|---|---|
| Control | 16 | 83 | 50 |
| +ascorbic acid at S3-S4 | 55 | 44 | 36 |

Example 12

Optimal Dose of Ascorbic Acid at Stage 3

This Example was carried out to determine the optimal dose of ascorbic acid to be used to generate insulin positive cells that are single hormonal, PDX-1 positive, and NKX6.1 positive.

Cells of the human embryonic stem cell line H1 at various passages (passage 40 to passage 52) were seeded as single cells at a density of 100,000 cells/cm$^2$ on MATRIGEL™ (1:30 dilution) coated dishes in mTesr™1 media and 10 μM of Y27632. Forty eight hours post seeding, cultures were differentiated into pancreatic endocrine lineage as follows:

a. Stage 1 (Definitive Endoderm (DE)—3 days): Prior to start of DE, the cultures were washed and incubated with incomplete PBS (no Mg or Ca) for 30 seconds followed by addition of the stage 1 media. Human embryonic stem cells cultured as single cells on MATRIGEL™-coated dishes were treated with MCDB-131 medium supplemented with 0.1% fatty acid-free BSA, 0.0012 g/ml sodium bicarbonate, 1× GlutaMax™, 5 mM D-Glucose, and 100 ng/ml GDF8 plus 1 μM MCX compound (GSK3B inhibitor) for one day. Cells were then treated with MCDB-131 medium supplemented with 0.1% fatty acid-free BSA, 0.0012 g/ml sodium bicarbonate, 1× GlutaMax™, 5 mM glucose, and 100 ng/ml GDF8 plus 100 nM MCX compound for day two, followed by an additional day in MCDB-131 medium supplemented with 0.1% fatty acid-free BSA, 0.0012 g/ml sodium bicarbonate, 1× GlutaMax™, 5 mM Glucose, and 100 ng/ml GDF8.

b. Stage 2 (Primitive gut tube—2 days): Stage 1 cells were treated with MCDB-131 medium supplemented with 0.1% fatty acid-free BSA, 0.0012 g/ml sodium bicarbonate, 1× GlutaMax™, 5 mM D-Glucose, with or without the addition of 0.25 mM ascorbic acid and 25 ng/ml FGF7 for two days.

c. Stage 3 (Foregut—2 days): Stage 2 cells were treated with MCDB131 medium supplemented with 1:200 dilution of ITS-X, 2.5 mM Glucose, 1× GlutaMax™, 0.0015 g/ml sodium bicarbonate, 2% fatty acid-free BSA, 10 ng/ml Activin A, 25 ng/ml FGF7, 0.25 μM SANT-1, +/−0.25 mM ascorbic acid, 1 μM RA, 200 nM TPB, 100 nM LDN-193189 for day 1, followed by treatment with MCDB131 medium supplemented with 1:200 dilution of ITS-X, 2.5 mM Glucose, 1× GlutaMax™, 0.0015 g/ml sodium bicarbonate, 2% fatty acid-free BSA, 10 ng/ml Activin A, 25 ng/ml FGF7, 0.25 μM SANT-1, +/−0.25 mM ascorbic acid, 1 μM RA, 200 nM TPB, 10 nM LDN-193189 for an additional day.

d. Stage 4 (Pancreatic foregut precursor—2 days): Stage 3 cells were treated with MCDB131 medium supplemented with 1:200 dilution of ITS-X, 2.5 mM Glucose, 1× GlutaMax™, 0.0015 g/ml sodium bicarbonate, 2% fatty acid-free BSA, 0.25 μM SANT-1, 50 nM RA, 200 nM TPB, 50 nM LDN-193189, with or without the addition of 0.25 mM to 1 mM ascorbic acid for two days.

e. Stage 5 (Pancreatic endoderm, 2-9 days): Stage 4 cells were treated with MCDB131 medium supplemented with a 1:200 dilution of ITS-X, 2.5 mM Glucose, 1× GlutaMax™, 0.0015 g/ml sodium bicarbonate, 2% fatty acid-free BSA, 0.25 μM SANT-1, 50 nM RA, with or without the addition of 0.25 mM ascorbic acid for 2-9 days.

Figure 21B:
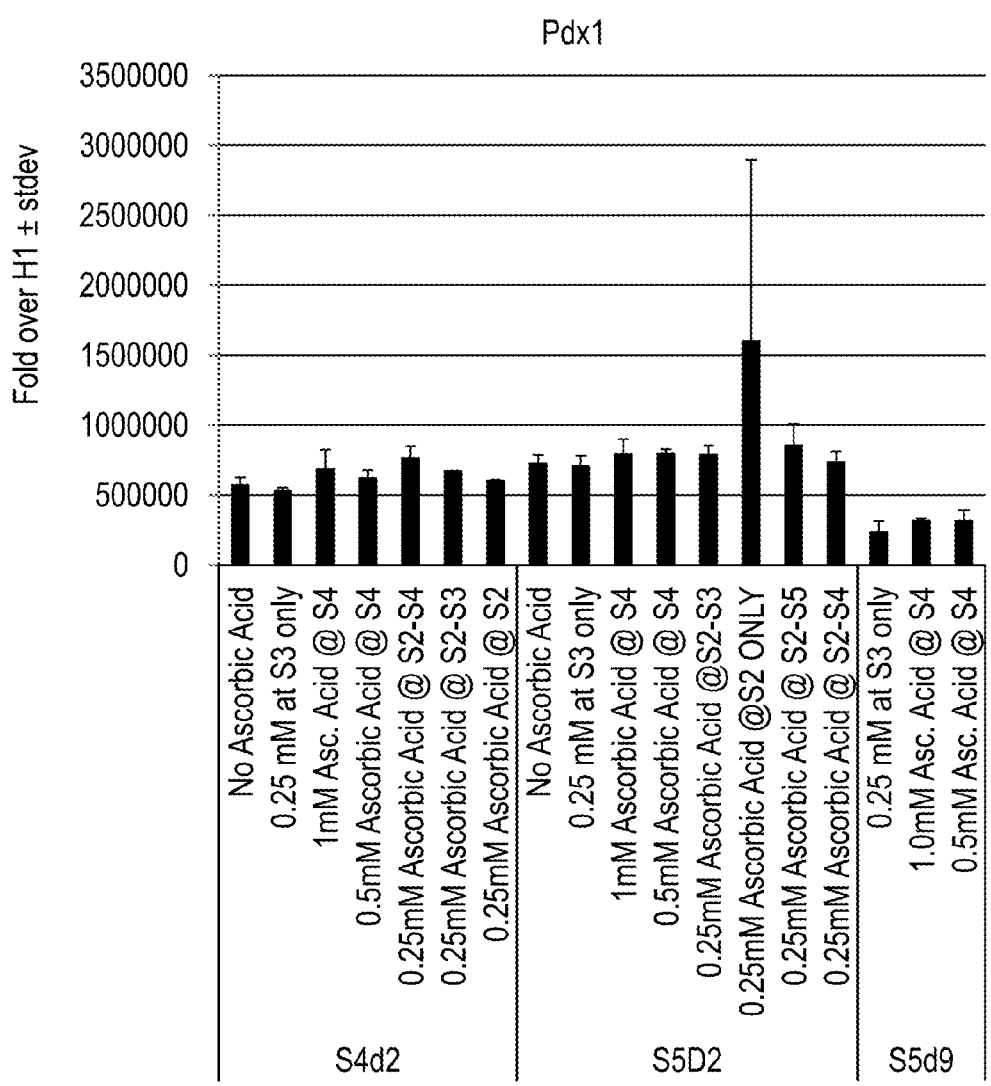
Figure 21D:
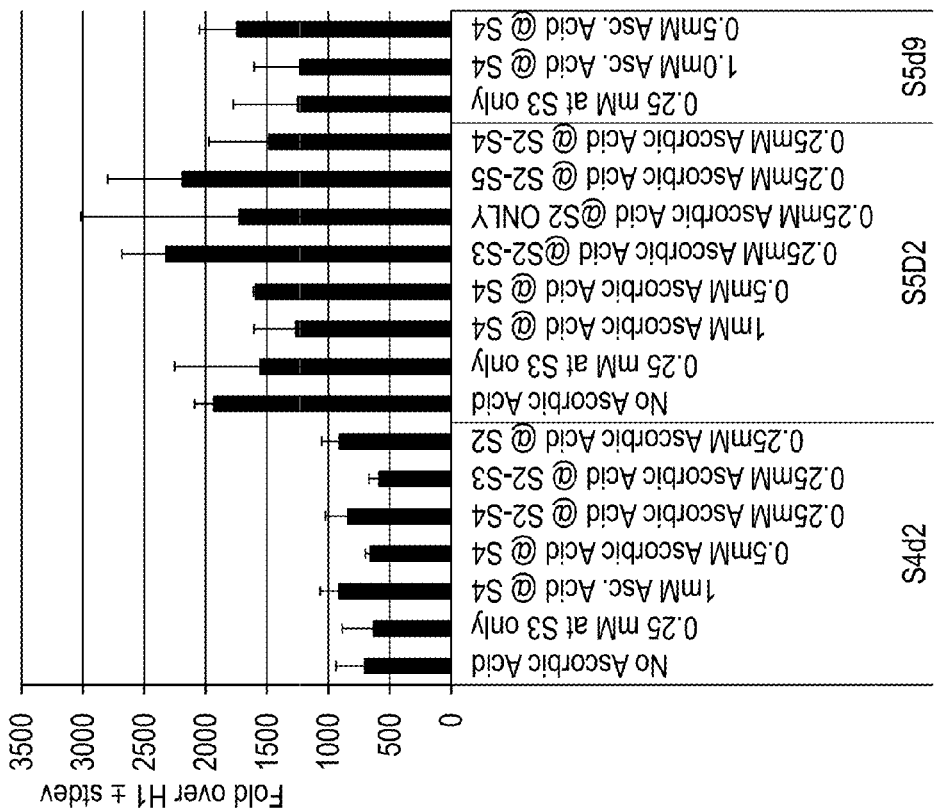
Figure 21C:
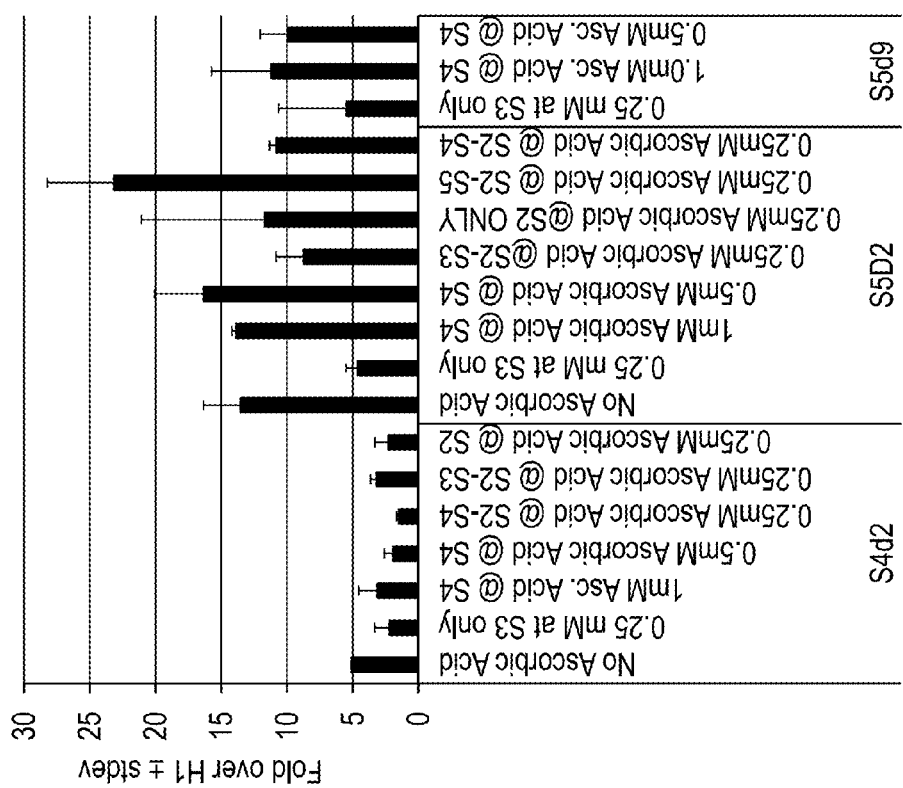
Figure 21E:
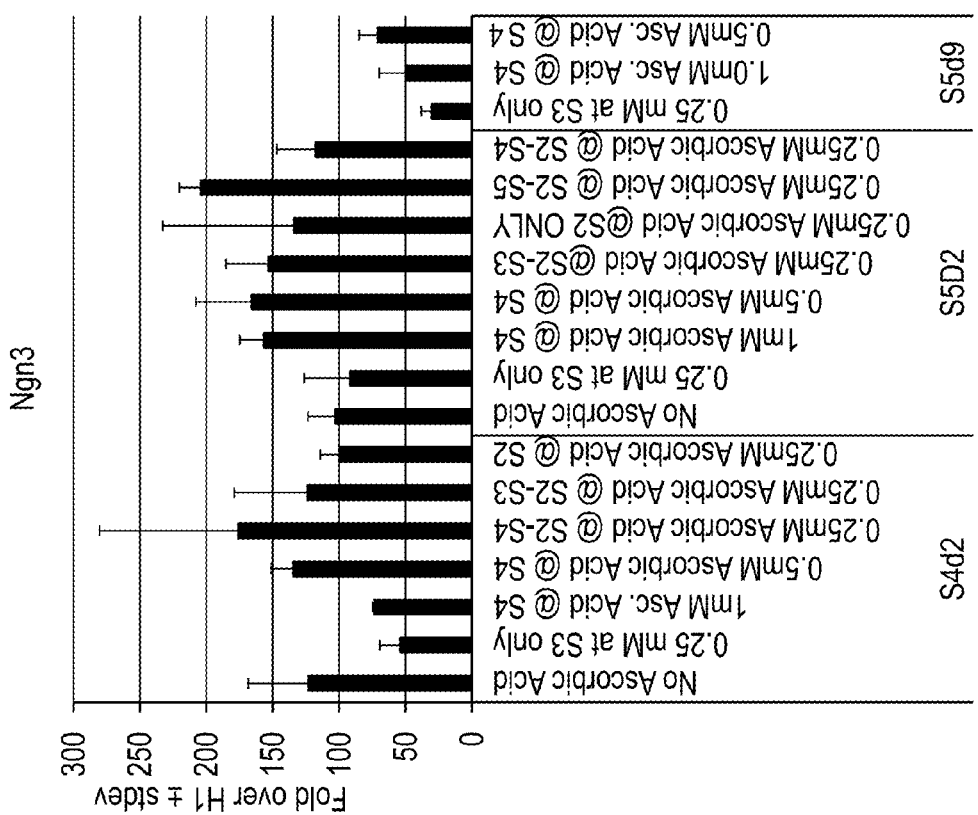
Figure 21F:
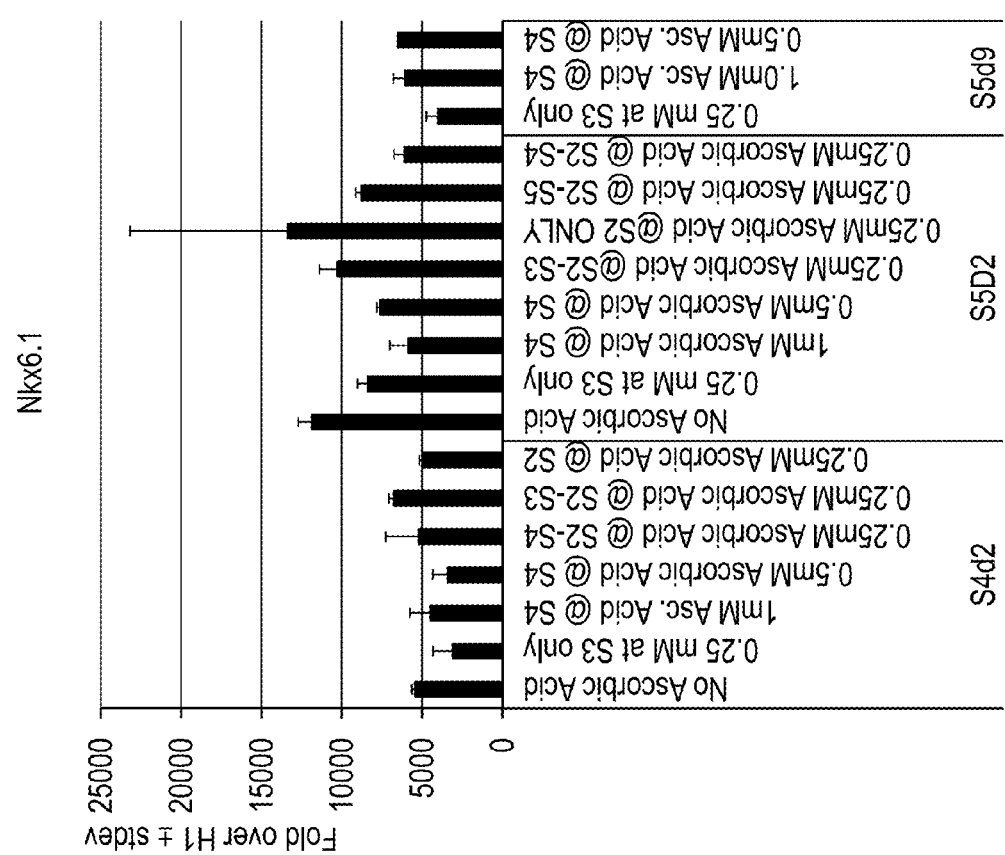
Figure 21H:
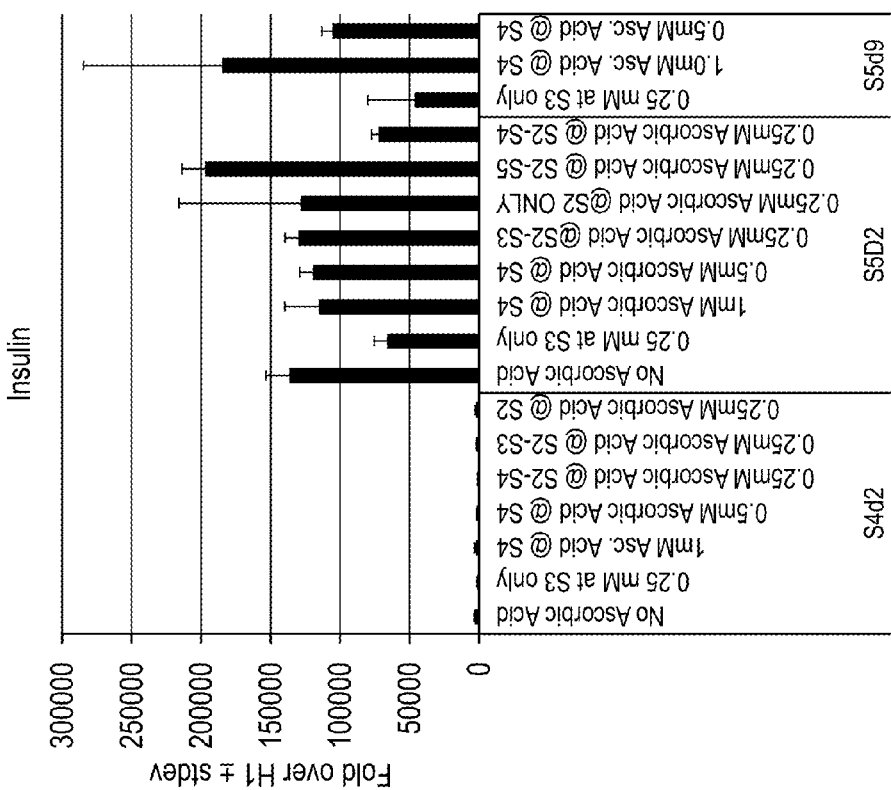
Figure 21G:
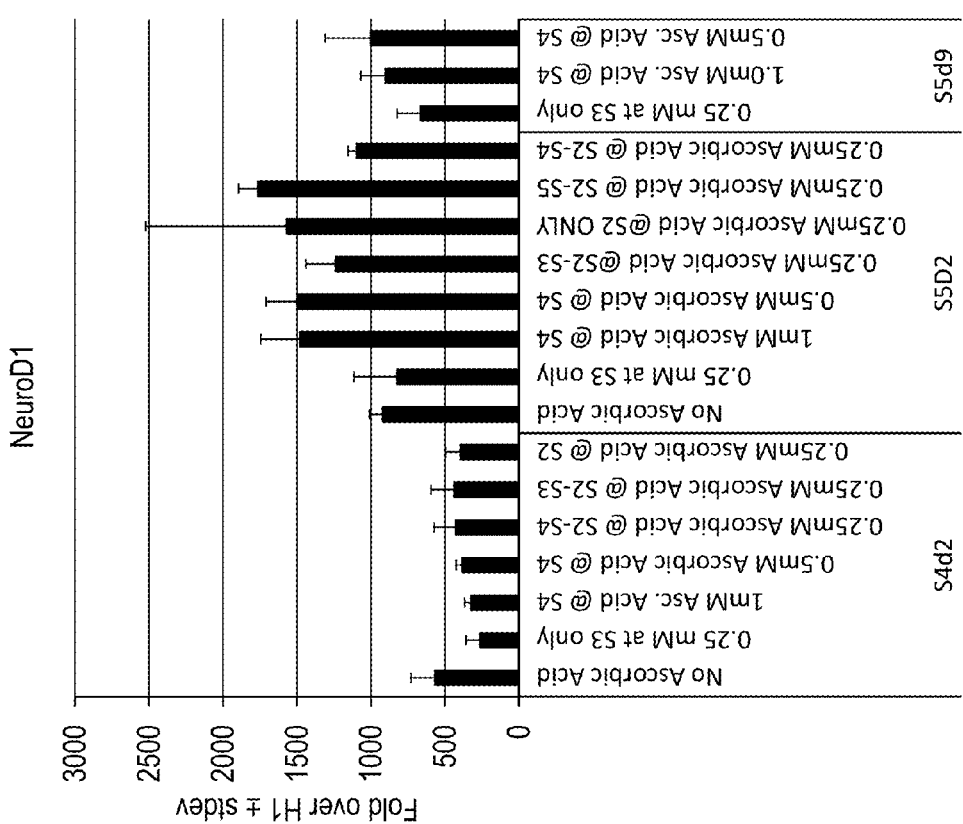

FIG. 21A to FIG. 21J depict data from real-time PCR analyses of the expression of the following genes in cells of the human embryonic stem cell line H1 differentiated according to the Example 12. FIG. 21A: somatostatin, FIG. 21B: PDX1, FIG. 21C: Pax6, FIG. 21D: Pax4, FIG. 21E: NKX6.1, FIG. 21F: NGN3, gFIG. 21G: NeuroD, FIG. 21H: insulin, FIG. 21I: glucagon, FIG. 21J: chromogranin. Consistent with the data from Example 10, addition of ascorbic acid at stages 2-4 significantly reduced expression of somatostatin, glucagon, and Pax6 while maintaining expression of insulin and Pax4 at stage 5. Furthermore, there was no significant benefit in using, at S4, 0.5-1 mM ascorbic acid as compared to 0.25 mM ascorbic acid. Lastly, addition of ascorbic acid at stage 2 also proved effective in lowering expression of glucagon and somatostatin at stage S3-5 while maintaining expression of insulin. Thus, ascorbic acid acts in a stage-specific fashion to regulate expression of single hormonal cells. Addition of ascorbic acid is important in early stages of the differentiation protocol, whereas at later stages it did not prove as effective in reducing numbers of polyhormonal cells.

Example 13

Combination of Retinoic Acid and Ascorbic Acid is Required to Generate Single Hormonal Insulin Positive Cells This Example was carried out to shed light on requirements to generate single hormonal insulin positive cells during differentiation of pluripotent cells.

Cells of the human embryonic stem cell line H1 at various passages (passage 40 to passage 52) were seeded as single cells at a density of 100,000 cells/cm$^2$ on MATRIGEL™ (1:30 dilution) coated dishes in mTesr™1 media and 10 μM of Y27632. Forty eight hours post seeding, cultures were differentiated into pancreatic endocrine lineage as follows:

a. Stage 1 (Definitive Endoderm (DE)—3 days): Prior to start of DE, the cultures were washed and incubated with incomplete PBS (no Mg or Ca) for 30 seconds followed by addition of the stage 1 media. Human embryonic stem cells cultured as single cells on MATRIGEL™-coated dishes were treated with MCDB-131 medium supplemented with 0.1% fatty acid-free BSA, 0.0012 g/ml sodium bicarbonate, 1× GlutaMax™, 5 mM D-Glucose, 100 ng/ml GDF8, 1 μM MCX compound (GSK3B inhibitor) for one day. Cells were then treated with MCDB-131 medium supplemented with 0.1% fatty acid-free BSA, sodium bicarbonate, GlutaMax™, extra 5 mM glucose, 100 ng/ml GDF8, and 100 nM MCX compound for day two followed by an additional day in MCDB-131 medium supplemented with 0.1% fatty acid-free BSA, 0.0012 g/ml sodium bicarbonate, 1× GlutaMax™, 5 mM Glucose, and 100 ng/ml GDF8.

b. Stage 2 (Primitive gut tube—2 days): Cells were treated with MCDB-131 medium supplemented with 0.1% fatty acid-free BSA, 0.0012 g/ml sodium bicarbonate, 1× GlutaMax™, 5 mM D-Glucose, 0.25 mM ascorbic acid, and 25 ng/ml FGF7 and for two days, then c. Stage 3 (Foregut—2 days): Cells were treated with MCDB131 supplemented with 1:200 dilution of ITS-X, 2.5 mM Glucose, 1× GlutaMax™, 0.0015 g/ml sodium bicarbonate, 2% fatty acid-free BSA, 10 ng/ml Activin A, 25 ng/ml FGF7, 0.25 mM ascorbic acid, 0.25 μM SANT-1, 1 μM RA, 200 nM TPB, 100 nM LDN-193189 for day 1, followed by treatment with tMCDB131 supplemented with 1:200 dilution of ITS-X, 2.5 mM Glucose, 1× GlutaMax™, 0.0015 g/ml sodium bicarbonate, 2% fatty acid-free BSA, 10 ng/ml Activin A, 25 ng/ml FGF7, 0.25 mM ascorbic acid, 0.25 μM SANT-1, 1 μM RA, 200 nM TPB, 10 nM LDN-193189 for an additional day.

d. Stage 4 (Pancreatic foregut precursor—2 days): Cells were treated with MCDB-131 medium supplemented with 1:200 dilution of ITS-X, 2.5 mM Glucose, 1× GlutaMax™, 0.0015 g/ml sodium bicarbonate, 2% fatty acid-free BSA, 0.25 μM SANT-1, 50 nM RA, 200 nM TPB, 50 nM LDN-193189, 0.1 mM ascorbic acid for two days, then e. Stage 5 (Pancreatic endoderm, 3 days): Cells were treated with MCDB-131 medium supplemented with 1:200 dilution of ITS-X, 2.5 mM Glucose, 1× GlutaMax™, 0.0015 g/ml sodium bicarbonate, 2% fatty acid-free BSA and the following culture conditions for 3 days:
+0.1 mM ascorbic acid
0.1 mM ascorbic acid+50 nM RA
0.1 mM ascorbic acid+50 nM RA+0.25 μM SANT-1
0.1 mM ascorbic acid+50 nM RA+0.25 μM SANT-1+50 nM LDN-193189
0.1 mM ascorbic acid+50 nM RA+0.25 μM SANT-1+1 μM Alk5 inh
0.1 mM ascorbic acid+50 nM RA+0.25 μM SANT-1+1 μM Alk5 inh+50 nM LDN-193189.

Figure 22A:
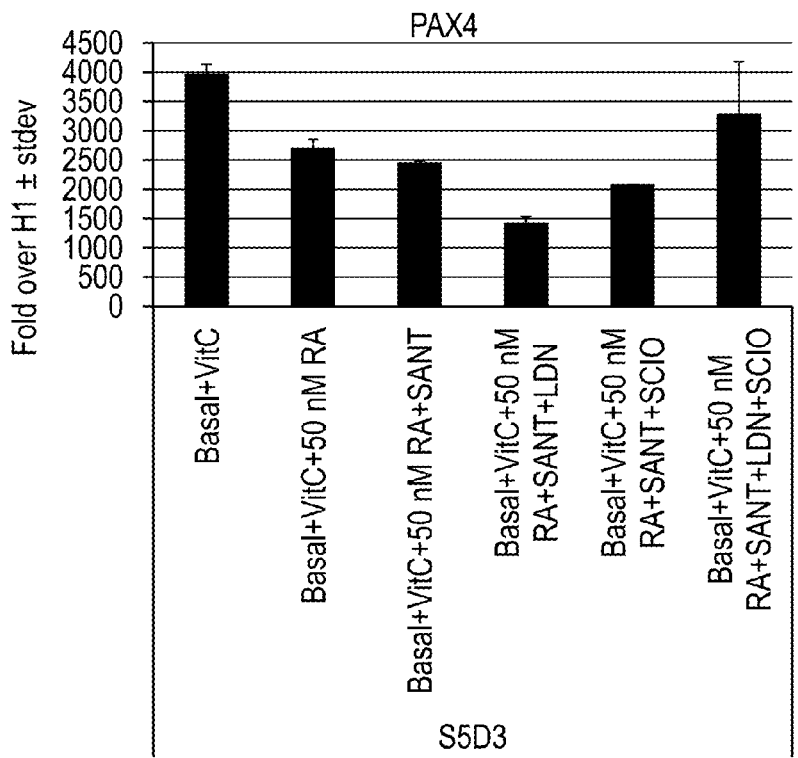
Figure 22B:
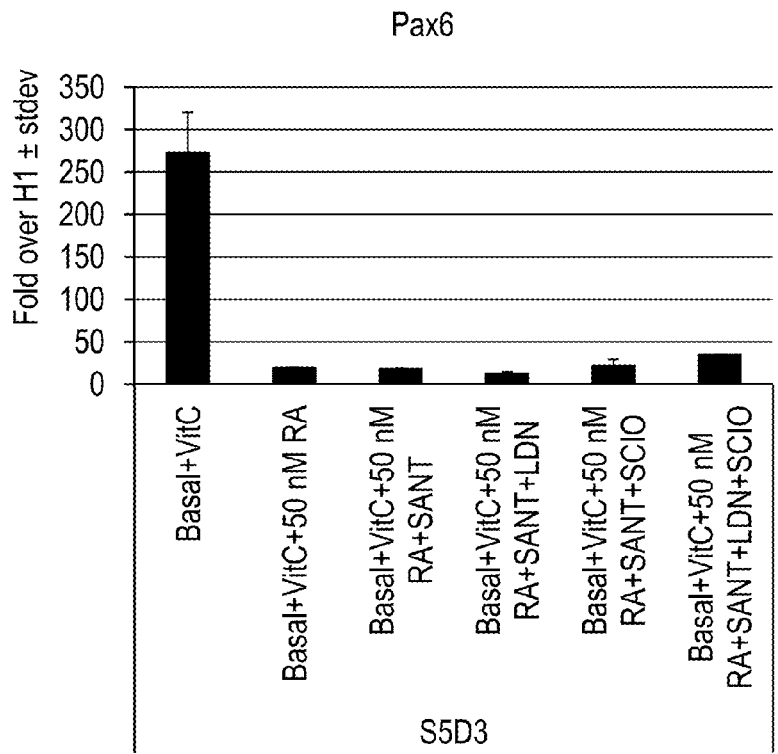
Figure 22C:
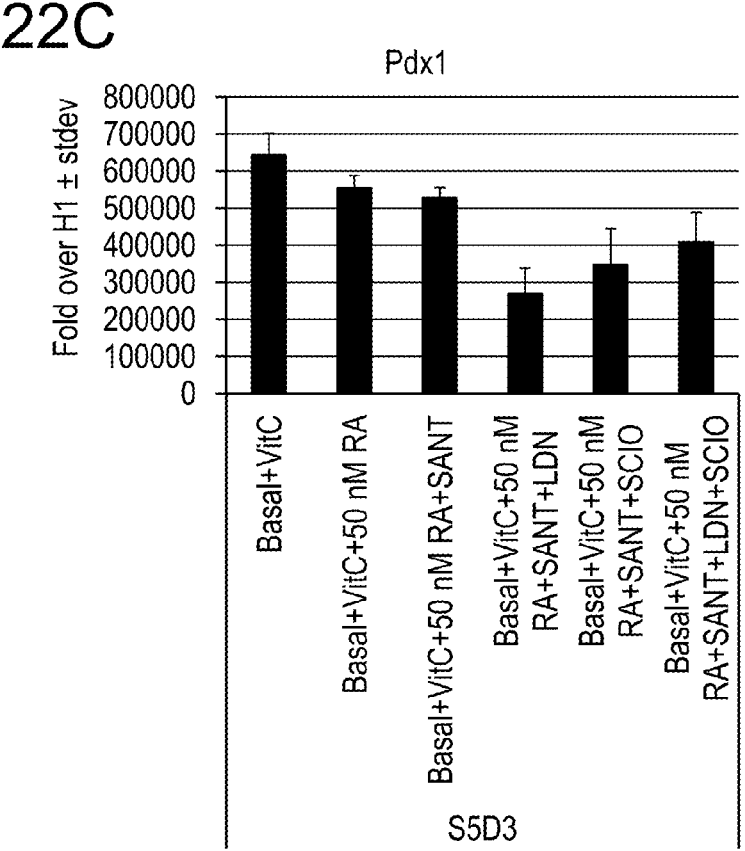
Figure 22D:
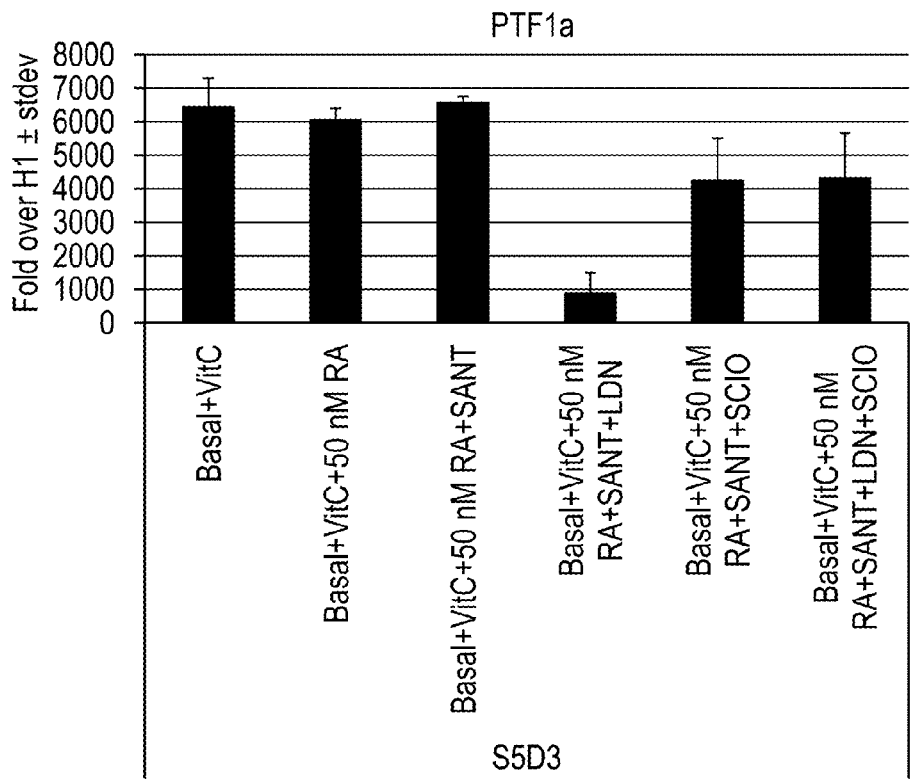
Figure 22H:
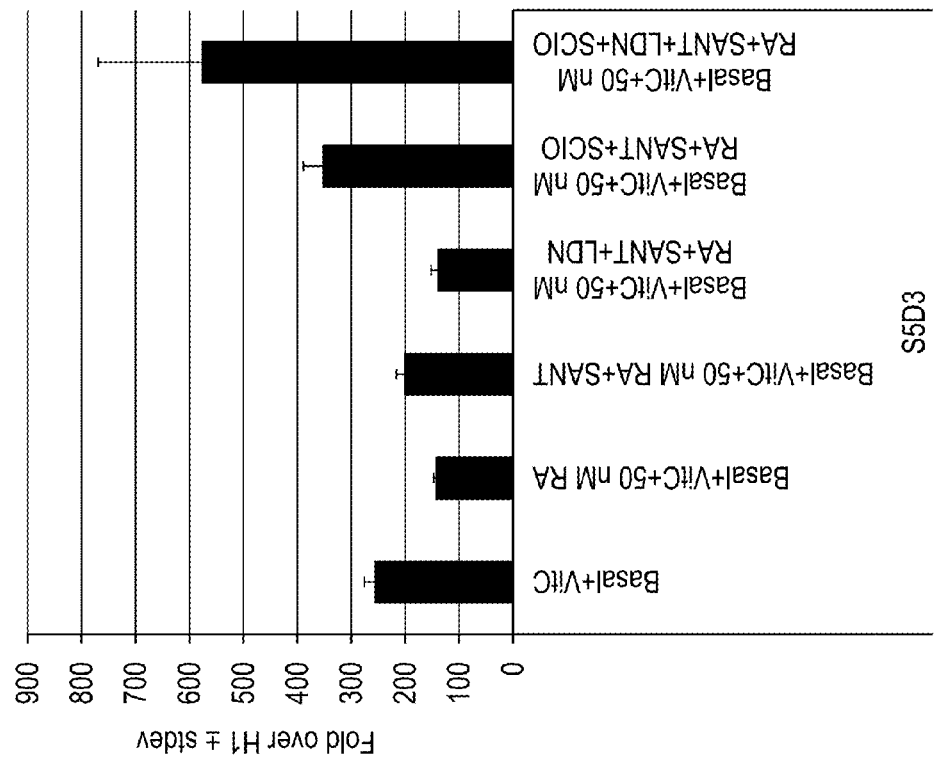
Figure 22G:
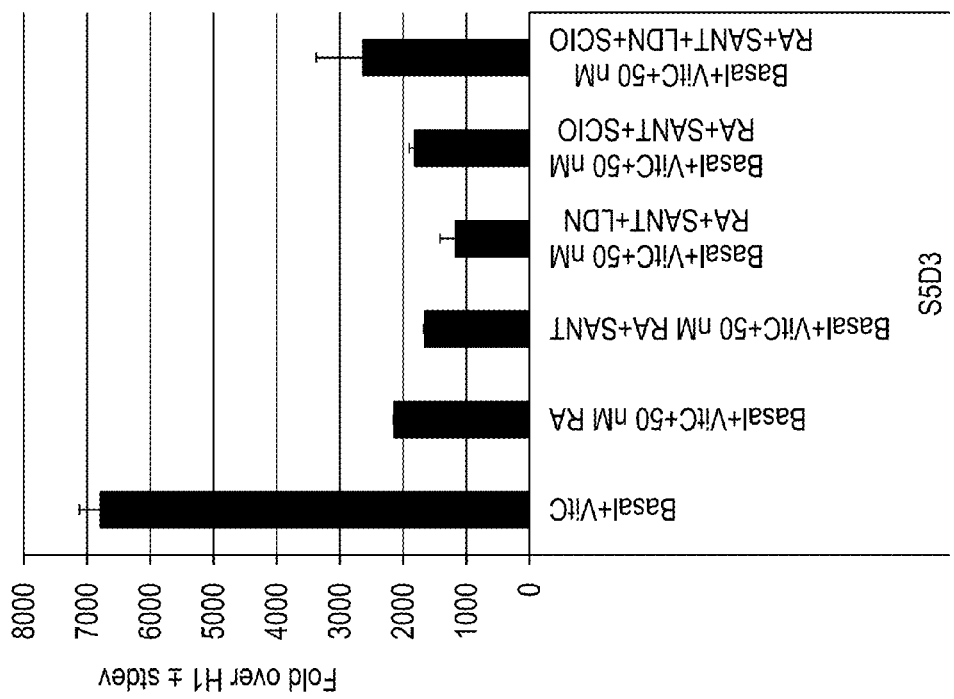
Figure 22J:
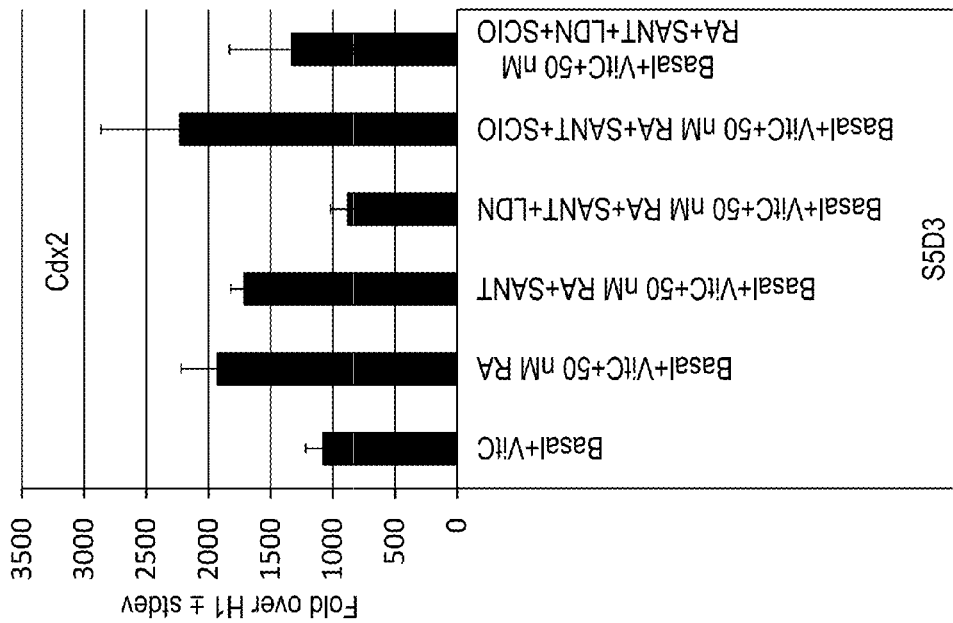
Figure 22I:
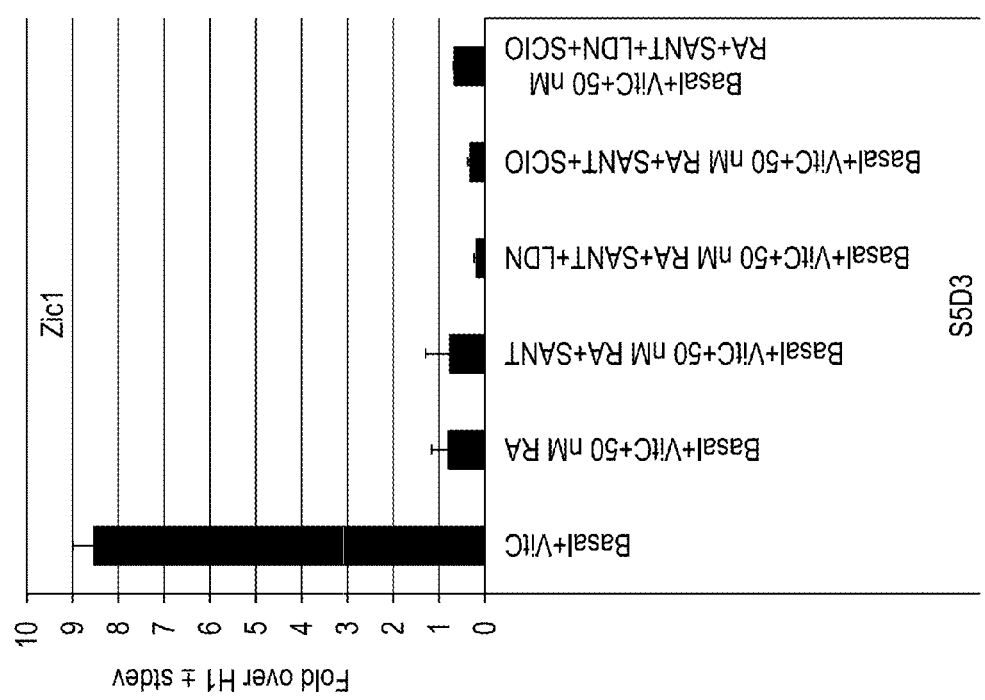
Figure 22L:
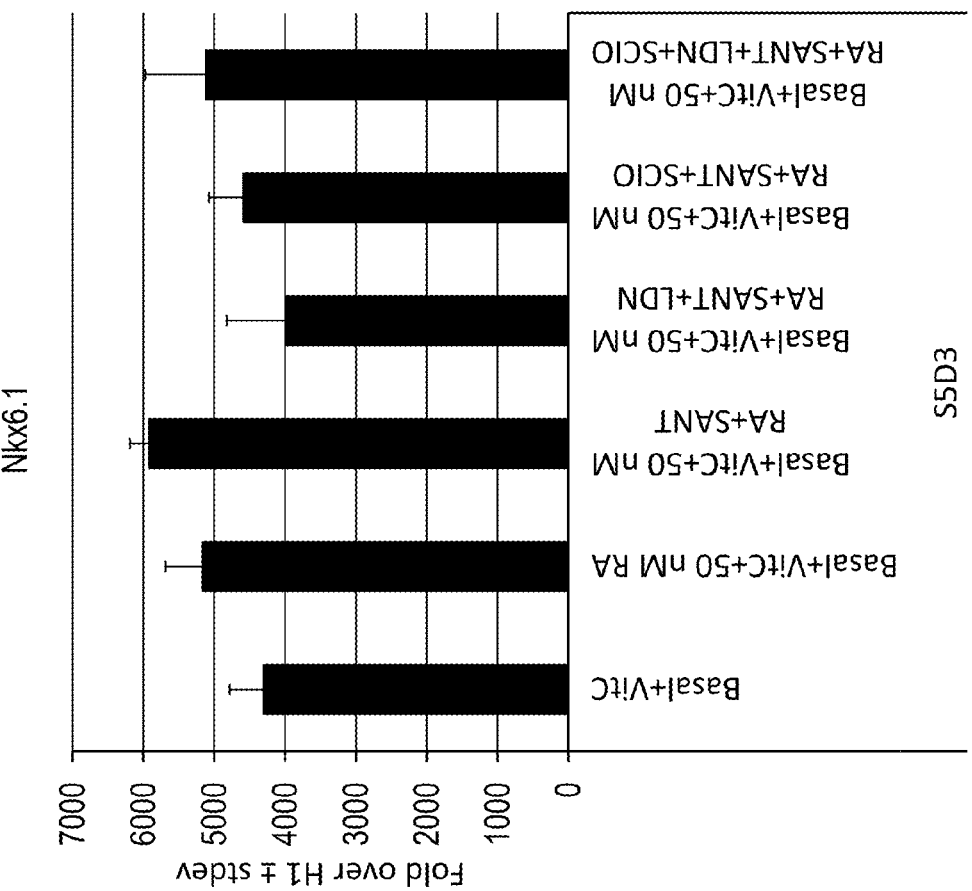
Figure 22K:
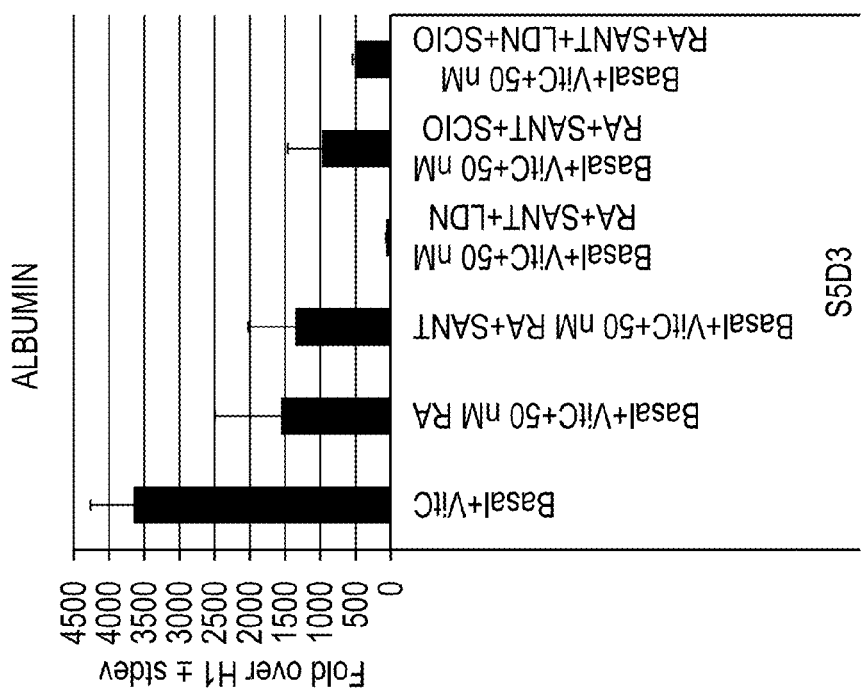

FIG. 22A through FIG. 22L show data from real-time PCR analyses of the expression of Pax4 (FIG. 22A); Pax6 (FIG. 22B); PDX1 (FIG. 22C); PTF1a (FIG. 22D); glucagon (FIG. 22E); insulin (FIG. 22F); NeuroD (FIG. 22G); ngn3 (FIG. 22H); Zic1 (FIG. 22I); CDX2 (FIG. 22J); albumin (FIG. 22K); NKX6.1 (FIG. 22L) in cells of the embryonic stem cell line H1 differentiated according to example 13 and harvested at S5 day 3.

At end of stage 5, cultures treated with combinations listed above were immune stained for insulin, glucagon, and somatostatin hormones. Table VIII summarizes average percentage of insulin positive cells, glucagon and somatostatin positive cells, and polyhormonal cells (two more hormone expression in one cell).

As sown in FIG. 22 and Table VIII, below, addition of low dose retinoic acid plus ascorbic acid at stage 5 significantly reduced overall number of hormone positive cells while increasing percentage of single hormonal insulin positive cells as compared to cultures treated only with vitamin C at S5. Furthermore, combination of retinoic acid, ascorbic acid, sonic hedgehog inhibitor, and ALK5 inhibitor further increased number of single hormonal insulin positive cells as compared to cultures treated only with ascorbic acid (Vitamin C). This data indicates that a unique combination of factors is needed to generate single hormonal insulin positive cells.

TABLE VIII

Expression of hormones as a percentage of the entire hormone count at S5 day 3.

| Treatment at S5 | % single hormonal Insulin+ | % glucagon + Plus % somatostatin+ | % Polyhormonal |
|---|---|---|---|
| +Vitamin C | 12 | 44 | 44 |
| +RA + Vitamin C | 27 | 26 | 43 |
| RA + Vitamin C + Alk5 inh + Shh Inh | 44 | 21 | 34 |

What is claimed is:

1. An in vitro method for producing a population of pancreatic cells comprising the steps of:

a) culturing undifferentiated human pluripotent stem cells in a medium supplemented with 5 mM to 20 mM glucose, a TGF-β ligand, and a WNT activator, to generate a population of definite endoderm (DE) cells;

b) culturing the DE cells in a medium supplemented with 5 mM to 20 mM glucose, and a FGF ligand to generate a population of gut tube cells;

c) culturing the gut tube cells in medium supplemented with 5 mM to 20 mM glucose, a shh inhibitor, a FGF ligand, a PKC activator, a TGF-β ligand, a retinoid, and a gradient of a BMP inhibitor to generate a population of posterior foregut endoderm cells expressing PDX-1 and SOX2;

d) culturing the posterior foregut cells in medium supplemented with 5 mM to 20 mM glucose, a PKC activator, a shh inhibitor, a retinoid, and a BMP inhibitor to generate a population of pancreatic foregut cells expressing PDX-1 and NKX6.1, and expressing lower level of SOX2 as compared to the posterior foregut cells;

e) culturing the pancreatic foregut cells in medium supplemented with 5 mM to 20 mM glucose, a shh inhibitor, a TGF-β inhibitor, ascorbic acid and a retinoid to obtain a population of cells, wherein said population comprises:
(i) greater than 30% of pancreatic endoderm cells that are PDX-1+, NKX6.1+, SOX2− and CDX2−, and
(ii) greater than 10% of single hormonal insulin positive cells.

2. An in vitro method for differentiating human pluripotent stem cells comprising the steps of:

a) culturing human pluripotent stem cells in a medium supplemented with 5 mM to 20 mM glucose, a TGF-β ligand, and a WNT activator, to generate a population of definite endoderm (DE) cells;

b) culturing the DE cells in a medium supplemented with 5 mM to 20 mM glucose, and a FGF ligand to generate a population of gut tube cells;

c) culturing the gut tube cells in medium supplemented with 5 mM to 20 mM glucose, a shh inhibitor, a FGF ligand, a PKC activator, a TGF-β ligand, a retinoid, and a gradient of a BMP inhibitor to generate a population of posterior foregut endoderm cells expressing PDX-1 and SOX2;

d) culturing the posterior foregut cells in medium supplemented with 5 mM to 20 mM glucose, a PKC activator, a shh inhibitor, a retinoid, and a BMP inhibitor to generate a population of pancreatic foregut cells expressing PDX-1 and NKX6.1, and expressing lower level of SOX2 as compared to the posterior foregut cells;

e) culturing the pancreatic foregut cells in medium supplemented with 5 mM to 20 mM glucose, a shh inhibitor, a TGF-β inhibitor, and a retinoid to obtain a population of pancreatic endoderm cells expressing PDX-1, a higher level of NKX6.1, and a lower level of SOX2 as compared to pancreatic foregut cells; and f) differentiating the pancreatic endoderm cells into a pancreatic β-cell population.

3. An in vitro method for differentiating human pluripotent stem cells comprising the steps of:

a) culturing human pluripotent stem cells in a medium supplemented with 5 mM to 20 mM glucose, a TGF-β ligand, and a WNT activator, to generate a population of definite endoderm (DE) cells;

b) culturing the DE cells in a medium supplemented with 5 mM to 20 mM glucose, and a FGF ligand to generate a population of gut tube cells;

c) culturing the gut tube cells in medium supplemented with 5 mM to 20 mM glucose, a shh inhibitor, a FGF ligand, a PKC activator, a TGF-β ligand, a retinoid, and a gradient of a BMP inhibitor to generate a population of posterior foregut endoderm cells expressing PDX-1 and SOX2;

d) culturing the posterior foregut cells in medium supplemented with 5 mM to 20 mM glucose, a PKC activator, a shh inhibitor, a retinoid, and a BMP inhibitor to generate a population of pancreatic foregut cells expressing PDX-1 and NKX6.1, and expressing lower level of SOX2 as compared to the posterior foregut cells;

e) culturing the pancreatic foregut cells in medium supplemented with 5 mM to 20 mM glucose, a shh inhibitor, a TGF-β inhibitor, and a retinoid to obtain a population of pancreatic endoderm cells expressing PDX-1, a higher level of NKX6.1, and a lower level of SOX2 as compared to pancreatic foregut cells; and f) differentiating the pancreatic endoderm cells into a pancreatic β-cell population.

4. The method of claim 2, wherein in at least one step the medium is further supplemented with ascorbic acid.

5. The method of claim 4, wherein the pancreatic β cells are single hormonal insulin-producing cells which are also NKX6.1+ and PDX-1+.

6. The method of claim 3, wherein the pancreatic β-cell population is PDX-1+, NKX6.1+, SOX2-, and CDX2-.

* * * * *